US007358349B2

(12) United States Patent
Nakagawara

(10) Patent No.: US 7,358,349 B2
(45) Date of Patent: Apr. 15, 2008

(54) NUCLEIC ACIDS HAVING EXPRESSION DIFFERENTIALS BETWEEN HEPATOBLASTOMA AND NORMAL LIVER

(75) Inventor: Akira Nakagawara, Chiba (JP)

(73) Assignees: Hisamitsu Pharmaceutical Co., Inc., Tosu-shi (JP); Chiba-Prefecture, Chiba-shi (JP)

( * ) Notice: Subject to any disclaimer, the term of this patent is extended or adjusted under 35 U.S.C. 154(b) by 277 days.

(21) Appl. No.: 10/487,422

(22) PCT Filed: Aug. 26, 2002

(86) PCT No.: PCT/JP02/08580

§ 371 (c)(1), (2), (4) Date: Feb. 23, 2004

(87) PCT Pub. No.: WO03/018807

PCT Pub. Date: Mar. 6, 2003

(65) Prior Publication Data

US 2005/0042613 A1 Feb. 24, 2005

(30) Foreign Application Priority Data

Aug. 24, 2001 (JP) ............................ 2001-255225

(51) Int. Cl.

*C07H 21/04* (2006.01)
*C12P 19/34* (2006.01)
*C12Q 1/68* (2006.01)

(52) U.S. Cl. ................. 536/23.1; 536/24.3; 536/24.31; 435/6; 435/91.1

(58) Field of Classification Search ..................... None
See application file for complete search history.

(56) References Cited

U.S. PATENT DOCUMENTS 5,474,796 A * 12/1995 Brennan .................... 427/2.13
6,312,695 B1 11/2001 Reed et al.
2003/0109690 A1 6/2003 Ruben et al.

FOREIGN PATENT DOCUMENTS

WO WO9928462 A2 * 6/1999
WO WO 99/47674 A2 9/1999
WO WO 00/55173 A1 9/2000
WO WO 00/61612 A2 10/2000
WO WO 01/00806 A2 1/2001
WO WO 01/2290 A 4/2001
WO WO 01/31015 A2 5/2001

(Continued)

OTHER PUBLICATIONS

Sequence alignment pp. 1-2.*

(Continued)

*Primary Examiner*—Sarae Bausch
(74) *Attorney, Agent, or Firm*—Fitch, Even, Tabin & Flannery

(57) ABSTRACT

A nucleic acid comprising any one of base sequences set forth in SEQ ID NO:1 to NO:104 in the Sequence Listing and a protein encoded by the nucleic acid, particularly a nucleic acid displaying differential expression levels in hepatoblastoma and normal liver based on comparison therebetween and a protein encoded by the nucleic acid as well as tumor detection utilizing the foregoing.

1 Claim, 6 Drawing Sheets

β-catenin wild type
β-catenin mutant
case14 case67 case78 case81 case10 case58 case77 case85
N T N T N T N T N T N T N T N T
HMFN1045
HMFT0128
HYST0281
HMFT1163
GAPDH

FOREIGN PATENT DOCUMENTS

| | | |
|---|---|---|
| WO | WO 01/60860 A2 | 8/2001 |
| WO | WO 01/75067 A | 10/2001 |
| WO | WO 01/75067 A2 | 10/2001 |

OTHER PUBLICATIONS

Definition of "represent", American Hertige Dictionary, of the English Language: Fourth Edition. 2000. (p. 1).*

Ross et al., H19 and IGF-2 allele-specific expression in hepatoblastoma, British Journal of Cancer, 82(4):753-756 (2000).

EBI Accession No. AAS64360, EMBL (Feb. 13, 2002).

EBI Accession No. AAH33613, EMBL Database (Sep. 3, 2001).

EMI Accession No. BG059740, EMBL Database (Jan. 29, 2001).

EBI, Accession No. AC000065, EMBL Database (Modification date: Feb. 26, 2004).

EBI Accession No. AK055922, EMBL Database (Modification date: Jan. 31, 2004).

Rijsewijk, et al. "The Drosphila Homolog of the Mouse Mammary Oncogene *int*-1 Is Identical to the Segment Polarity Gene *wingless*" Cell, vol. 50, pp. 649-657, (Aug. 14, 1987).

Nusse, et al. "Many Tumors Induced by the Mouse Mammary Tumor Virus Contain a Provirus Integrated in the Same Region of the Host Genome" Cell, vol. 31, pp. 99-109 (Nov. 1982).

"Hepatoblastoma is a Simplified Model of Wnt Signal Abnormality" Experimental Medicine, vol. 19, No. 6, pp. 804-809 (2001).

Clay, et al. "Identification and cloning of a protein kinase-encoding mouse gene, *Plk*, related to the *polo* gene of *Drosophila*" Proc.Natl. Acad. Sci. USA, vol. 90, pp. 4882-4886, (Jun. 1993).

Yamada, et al. "Analysis of Gene Expression Profile in Hepatoblastoma and Search of Gene Related to New Hepatoblastoma," Chiba Cancer Center Research Institute, vol. 38, No. 3, p. 362, Abstract S-1-3 (2001).

Yamada, et al. "Analysis of Gene Expression Profile in Hepatoblastoma and Search of Gene Related to New Hepatoblastoma," Chiba Cancer Center Research Institute, vol. 60, p. 537, Abstract 1833 (2001).

Takayasu, et al. "Frequent Deletions and Mutation of the β-*Catenin* Gene Are Associated with Overexpression of *Cyclin D1* and *Fibronectin* and Poorly Differentiated Histology in Childhood Hepatoblastoma[1]," Clinical Cancer Research, vol. 7, pp. 901-908, (Apr. 2001).

Japanese Office Action dated Sep. 20, 2007.

Yamada Shin-Ichi et al.; "Expression profiling and differential screening between hepatoblastomas and the corresponding normal livers: identification of high expression of the PLK 1 oncogene as a poor-prognostic indicator of heptoblastomas" ONCOGENE, vol. 23, No. 35, Aug. 5, 2004, pp. 5901-1911.

Ross J A et al: "H19 and IGF-2 allele-specific expression in hepatoblastoma"; British Journal of Cancer, London, GB, vol. 82, No. 4, Feb. 2000, pp. 753-756.

Takayasu H et al: "Frequent deletions and mutations of the beta-catenin gene are associated with overexpression of cyclin D1 and fibronectin and poorly differentiated histology in childhood hepatoblastoma" Clinical Cancer Research, The American Association for Cancer Research, US, vol. 7, No. 4, Apr. 2001, pp. 901-908.

NCBI Accession No. BG059740.

Sambrook et al., Molecular Cloning: A Laboratory Manual, Third Edition, 2001, pp. 10.47 and 10.48, vol. 2, Cold Spring Harbor Laboratory Press, Cold Spring Harbor, New York.

* cited by examiner

NUCLEIC ACIDS HAVING EXPRESSION DIFFERENTIALS BETWEEN HEPATOBLASTOMA AND NORMAL LIVER

CROSS-REFERENCED APPLICATIONS

This application is the National Stage of International Application PCT/JP02/08580, filed Aug. 26, 2002, the complete disclosure of which is incorporated herein by reference, which designated the U.S. and that International Application was not published under PCT Article 21(2) in English.

TECHNICAL FIELD

This invention relates to nucleic acids having differential expression levels in hepatoblastoma and normal liver based on comparison therebetween.

BACKGROUND ART

Individual tumors exhibit distinct characteristic natures, and their biological properties are not necessarily identical even though the basic principle of oncogenesis is the same. Rapid advances in the understanding of cancer from a molecular biological and molecular genetic perspective in recent years have opened the way to an explanation of oncogenesis and tumor cell biology on the genetic level.

Hepatoblastoma is a malignant hepatoma occurring in infants with the highest frequency and 70% of the infants develop it before they reach two years of age. The infants who have been afflicted with hepatoblastoma generally experience a systemic decline in health and exhibit a large mass in the right upper abdomen. In hepatoblastoma if its detection is at an early stage, there will be some hope of long-term survival through chemotherapy and surgical operation. When the detection is late, complete cure will be difficult; therefore, early detection is desired.

AFP (alpha-fetoprotein) in blood is the only hepatoblastoma marker in the diagnosis of hepatoblastoma that has been known to date. Hepatoblastoma has thus been diagnosed by detection or quantification of AFP. However, it is known that the blood concentration of AFP rises not only in hepatoblastoma but also in hepatoma. There is also a drawback that its specificity is low and its values have sometimes been elevated in diseases other than hepatoblastoma or hepatoma (such as liver cirrhosis). Accordingly, AFP is insufficient for the use as a tumor marker specific for hepatoblastoma. A problem has existed that there is no other way but the ultimate collection of part of the carcinoma tissue followed by its pathological and histological diagnosis.

DISCLOSURE OF THE INVENTION

This invention has been made in light of the problem inherent in the above-stated prior art, and its object is to identify the genes displaying differential expression levels between hepatoblastoma and normal liver, and to allow the provision of their genetic information as well as the diagnosis of the tumor.

As a result of conducting diligent research in order to accomplish the above-mentioned objects, the present inventors have succeeded in constructing cDNA libraries from both clinical tissues of human hepatoblastoma and normal liver. The genes of 6000 hepatoblastoma clones and 3000 normal liver clones from these two types of cDNA libraries were subjected to end sequencing and their expression profiles were analyzed.

Moreover, the present inventors found that some among the analyzed genes had differential expression levels between the hepatoblastoma clinical tissue and the normal liver clinical tissue and they made it possible to provide the base sequence information that would allow the detection and cloning of the genes.

Furthermore, based on the aforementioned base sequence information it has been made possible to design tumor markers which can be used for the diagnosis of hepatoblastoma, and this invention has thereupon been completed.

Specifically, the nucleic acid of this invention is a nucleic acid having differential expression levels in hepatoblastoma and normal liver based on comparison therebetween, the nucleic acid comprising any one of base sequences set forth in SEQ ID NO:1 to NO:79 in the Sequence Listing.

Here, the nucleic acid of the invention may be a nucleic acid comprising a portion of any one of base sequences set forth in SEQ ID NO:1 to NO:79 in the Sequence Listing.

Also, the nucleic acid of the invention may be an isolated nucleic acid characterized in that it hybridizes to the nucleic acid comprising any one of base sequences set forth in SEQ ID NO:1 to NO:79 in the Sequence Listing or its fragment, or its complementary nucleic acid under stringent conditions.

The probe for tumor detection of this invention is characterized in that it is a nucleic acid comprising any one of base sequences set forth in SEQ ID NO:1 to NO:104 in the Sequence Listing. Here, the probe for tumor detection may be a nucleic acid comprising a portion of said nucleic acid.

The probe for tumor detection of the invention may also be an isolated nucleic acid hybridizing to the nucleic acid comprising any one of base sequences set forth in SEQ ID NO:1 to NO:104 in the Sequence Listing or its fragment, or its complementary nucleic acid under stringent conditions.

Further, the PCR primer for tumor detection of this invention is characterized by being able to amplify a nucleic acid comprising any one of base sequences set forth in SEQ ID NO:1 to NO:104 in the Sequence Listing.

Also, the marker protein for tumor detection of this invention is characterized in that it is a protein which can be encoded by a nucleic acid comprising any one of base sequences set forth in SEQ ID NO:1 to NO:104 in the Sequence Listing.

By utilizing the probe for tumor detection, the PCR primer for tumor detection, or the marker protein for tumor detection, the diagnoses of various tumors will be feasible.

Still further, the diagnostic agent for tumor detection of this invention contains at least one nucleic acid comprising a portion or the whole of any one of the base sequences set forth in SEQ ID NO:1 to SEQ ID NO:104 in the Sequence Listing. Specifically, such tumor detection diagnostic agents include DNA chips and microarrays both of which are produced using the above-mentioned nucleic acids, for example.

As used herein, as a tumor that is targeted by the probe for tumor detection, the PCR primer for tumor detection, the marker protein for tumor detection and the diagnostic agent for tumor detection, there may be mentioned liver cancer, colorectal cancer, breast cancer, kidney cancer, gastric cancer, ovarian cancer, thyroid cancer and the like, but the tumor is preferably hepatoblastoma.

BEST MODE FOR CARRYING OUT THE INVENTION

Figure 1:
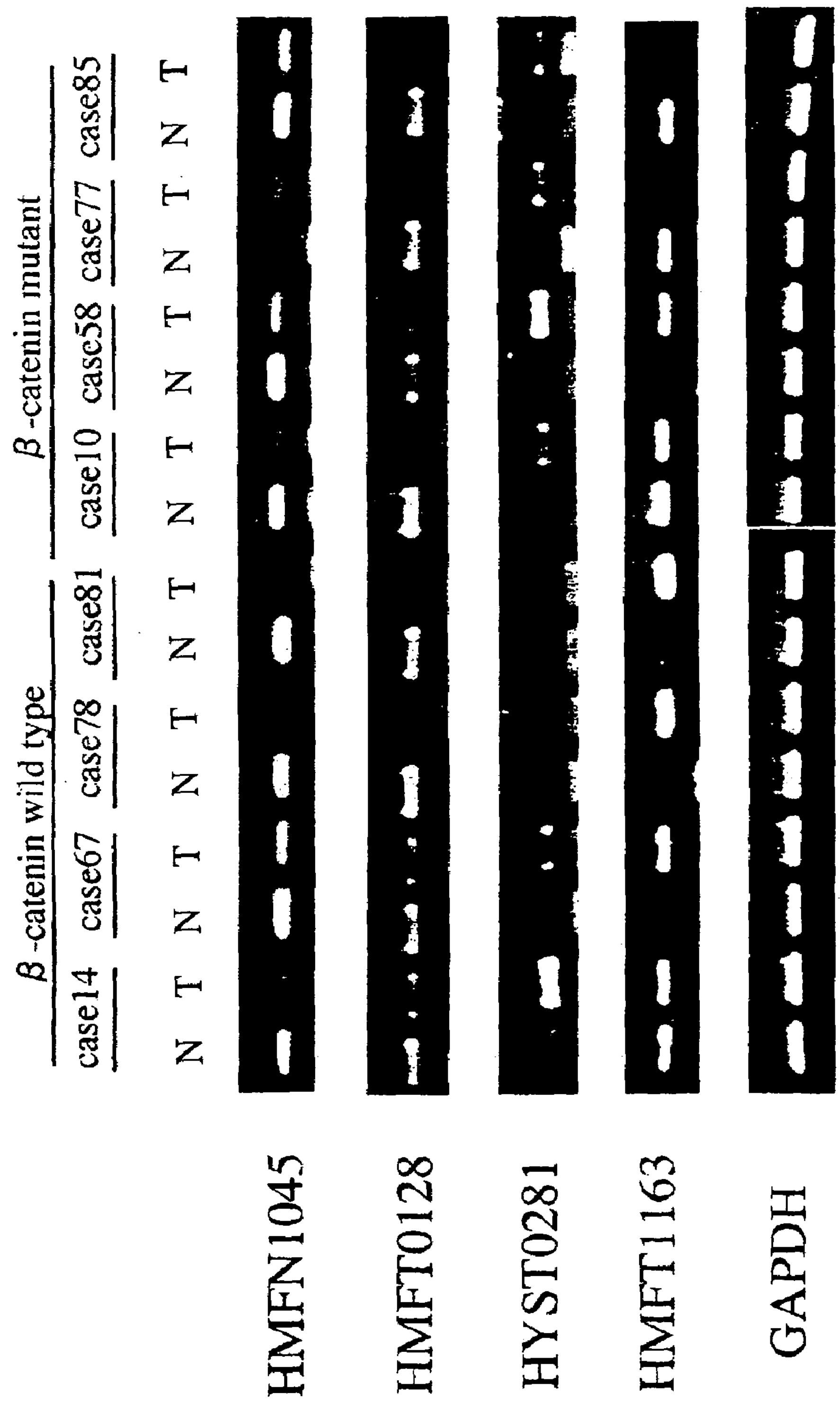
FIG. 1 is a figure corresponding to an electrophoregram showing an example of the results from differential screening by RT-PCR.

The term "nucleic acid(s)" as used in this invention refers to, for example, DNA or RNA, or polynucleotides derived therefrom which may be active as DNA or RNA, and preferably it refers to DNA and/or RNA.

The term "hybridize under stringent conditions" means that two nucleic acid fragments hybridize to each other under the hybridization conditions described by Sambrook, J. et al. in "Expression of cloned genes in *E. coli*," Molecular Cloning: A Laboratory Manual (1989), Cold Spring Harbor Laboratory Press, New York, USA, 9.47-9.62 and 11.45-11.61.

More specifically, the "stringent conditions" refers to hybridization at approximately 45° C. with 6.0× SSC, followed by washing at 50° C. with 2.0× SSC. The stringency may be selected by choosing a salt concentration in the washing step from approximately 2.0× SSC, 50° C. as low stringency to approximately 0.2× SSC, 50° C. as high stringency. Also, the temperature in the washing step may be increased from room temperature, or approximately 22° C. as low stringency conditions, to approximately 65° C. as high stringency conditions.

The term "isolated nucleic acid(s)" as used in the present specification refers to a nucleic acid or a polynucleotide containing substantially no cellular substances or culture medium, if prepared by recombinant DNA techniques, or containing substantially no precursor chemical substances or other chemical substances, if prepared by chemical synthesis.

The term, "marker protein for tumor detection" as used in this invention refers to a protein having an amino acid sequence that is endowed with the phenotype whose expression in a tumor cell or a tumor tissue allows the judgment on the tumor cell or the tumor tissue as to whether the tumor cell or the tumor tissue is derived from the tumor.

The nucleic acids of this invention will be first described.

The nucleic acid of this invention is a nucleic acid having differential expression levels in hepatoblastoma and normal liver based on comparison therebetween, the nucleic acid comprising any one of base sequences set forth in SEQ ID NO:1 to NO:79 in the Sequence Listing.

The nucleic acid of the invention may also be a nucleic acid comprising a portion of any one of base sequences set forth in SEQ ID NO:1 to NO:79 in the Sequence Listing.

Further, the nucleic acid of the invention may be a nucleic acid hybridizing to the nucleic acid comprising any one of base sequences set forth in SEQ ID NO:1 to NO:79 in the Sequence Listing or its fragment, or its complementary nucleic acid under stringent conditions. The base sequence is not particularly limited insofar as it satisfies this condition. Such base sequences specifically include a nucleic acid comprising deletions, substitutions, insertions or additions in some bases of the nucleic acid comprising any one of base sequences set forth in SEQ ID NO:1 to NO:79 or its complementary nucleic acid thereof. As used herein, the deletion, the substitution, the insertion and the addition include not only a short deletion, substitution, insertion and addition with 1 to 10 bases, but also a long deletion, substitution, insertion and addition with 10 to 100 bases.

On the other hand, the nucleic acid comprising any one of base sequences set forth in SEQ ID NO:80 to NO:102 in the Sequence Listing has been isolated as the gene having differential expression levels in hepatoblastoma and normal liver based on comparison therebetween similarly to the case of the nucleic acid comprising any one of base sequences set forth in SEQ ID NO:1 to NO:79 in the Sequence Listing. However, the former nucleic acid differs from the nucleic acid comprising any one of base sequences set forth in SEQ ID NO:1 to NO:79 in that it has been determined to have the same base sequence as does a known gene whose base sequence is already publicly disclosed during a homology search for its base sequence.

The nucleic acid comprising any one of base sequences set forth in SEQ ID NO:1 to NO:104 can be obtained from a clinical tissue of hepatoblastoma or normal liver. An example of the method for obtaining those nucleic acids will be described below.

CDNA libraries are first constructed from a hepatoblastoma clinical tissue and a normal liver clinical tissue according to a known method, and the base sequences of the genes cloned from the respective cDNA libraries are determined.

Primers for PCR are designed based on the determined base sequences, and the cDNA libraries derived respectively from the hepatoblastoma and the normal liver are used as templates to carry out PCR semi-quantitatively. Screening is conducted for the genes whose expression levels are differentially noted in hepatoblastoma and normal liver based on comparison therebetween. Here, the semi-quantitative PCR may be performed according to a known method, and specifically, it may be performed by adjusting the concentration of cDNA, which serves as the template, and thereafter carrying out normal PCR. In this case, the PCR conditions may adequately be determined depending on the base numbers of primers for use or Tm values. The thus obtained PCR products may be electrophoresed on agarose gel or acryl amide gel and determination may be made as to whether there is a noted difference in the expression level between hepatoblastoma and normal liver. As for the method of screening a gene for which expression levels are different in hepatoblastoma and normal liver based on comparison therebetween, there may be mentioned a method of cloning genes from plural specimens based on the differential expression levels as an index, including differential display other than the method by differential screening as described above.

The thus obtained nucleic acids of this invention have been found as the genes having differential expression levels in hepatoblastoma and normal liver based on comparison therebetween. Such nucleic acids are provided with the characteristics described below.

Hepatoblastoma is one of liver cancers that develops only at infancy and this suggests that the analysis of genes whose expression levels are enhanced or lowered therein provides information very useful for the understanding of the biology of hepatic cells. That is, the nucleic acids of this invention are the genes involved in the early phase of hepatic development, and at the same time, are the important genes involved in the proliferation and differentiation of hepatic cells, which can be mentioned as characteristics of the nucleic acids.

Hepatoblastoma is also characteristically a pediatric tumor, and because of the very low possibility of effects by acquired factors, it is expected that analysis of the mechanism of cancerization will also yield embryological information with high probability.

Furthermore, the nucleic acids of this invention are those for which differential expression levels are noted in hepatoblastoma and normal liver based on comparison therebetween. Therefore, the nucleic acids can also be utilized as data for tumor markers to diagnose hepatoblastoma by detecting DNA and/or RNA having any of their base sequences and by detecting a protein encoded by the DNA.

In addition, it has been reported in recent years that there is anomaly in the Wnt signal transduction path in hepatoblastoma. Wnt is a notation originating in wingless which was found as one of the segment polarity genes of *drosophila* (Rijsewijk F. et al., Cell, 50: 649, 1987) and in int-1 which was identified in murine breast cancer (Nusse R. et al., Cell, 31: 99, 1982): similar genes are also included and generally termed "Wnt."

Wnt shows time- and location-dependent expression at various phases in all animals including nematodes, insects, mice and humans; Wnt functions as an inducing factor of morphogenesis, a polarity-determining factor of cell and a modulating factor of proliferation and differentiation.

Further, in many cancers such as colorectal cancer, breast cancer, kidney cancer, gastric cancer and thyroid cancer, 20 to 30% of the cancers are knowingly due to the anomaly of Wnt signal. There has also been a report that a majority of such anomalies of the Wnt signal is caused by mutation in β-catenin gene (Jikken Igaku: Experimental Medicine Vol. 19, No. 6, 2001). Mutation in β-catenin at the somatic cell level is also noted in 65% of Japanese hepatoblastoma patients. Immunohistochemical staining recognizes the nuclear accumulation of β-catenin in approximately 85% of hepatoblastoma patients. These suggest that the anomaly of β-catenin or the anomaly in the Wnt signal is responsible for the crisis of hepatoblastoma.

It is also suggested that the Wnt signal transduction path is connected to oncogenesis since cancer suppressor genes such as APC (which is the causative gene of familial colorectal adenoma) are present in the path. Specifically, catenin existing in cytoplasm increases due to the anomaly in the Wnt signal transduction path and the catenin binds to transcription factor TCF/LEF, which is believed to contribute to oncogenesis.

The nucleic acid of this invention comprising any one of base sequences set forth in SEQ ID NO:1 to SEQ ID NO:104 in the Sequence Listing is in the group of genes for which differential expression levels are noted in hepatoblastoma and normal liver based on comparison therebetween. The nucleic acid, therefore, is believed to be more or less involved in the anomaly in the Wnt signal. Accordingly, one or more genes in the gene group are analyzed for their expression levels and they can be used as markers for detection of any anomaly in the Wnt family or the Wnt signal transduction path in addition to as cancer markers for various cancers such as colorectal cancer, breast cancer, kidney cancer, gastric cancer, ovarian cancer and thyroid cancer, not to mention hepatoblastoma.

The nucleic acids of this invention further encompass a cancer gene known as Plk-1 (polo-like kinase-1). (Clay F. J. et al., Proc. Natl. Acad Sci USA., 90: 4882-6, 1993.) Plk-1 displays noted differential expression levels in hepatoblastoma and normal liver based on comparison therebetween similarly to the case of the nucleic acid of the invention comprising any one of base sequences set forth in SEQ ID NO:1 to SEQ ID NO:101 and SEQ ID NO:103 to SEQ ID NO:104 in the Sequence Listing. The base sequence of Plk-1 is shown in SEQ ID NO:102 in the Sequence Listing (Gene Bank Accession No. X73458).

Thus, when the nucleic acid of the invention comprising any one of base sequences set forth in SEQ ID NO:1 to SEQ ID NO:104 in the Sequence Listing is used as a cancer marker, the cancer targeted for diagnosis is not particularly limited insofar as it is regarded as resulting from the anomaly in the Wnt signal, particularly the anomaly of β-catenin gene. Preferably, it is any of hepatoblastoma described above (to begin with), liver cancer, colorectal cancer, breast cancer, kidney cancer, gastric cancer, ovarian cancer and thyroid cancer. More preferably, it is any of hepatoblastoma, hepatocellular carcinoma (HCC), hereditary non-polyposis colorectal cancer (HNPCC), desmoid tumor, ovarian cancer, anaplastic thyroid carcinoma and Willms' tumor.

As stated above, this invention will make it possible to obtain various kinds of information on hepatoblastoma or related thereto through the following means.

(1) Probes for Use in Hybridization

The nucleic acid comprising a portion or the whole of a base sequence disclosed in this specification (or which may be referred to as "nucleic acid(s) of the invention") may be at least used as a probe for hybridization in order to detect genes expressed in human hepatoblastoma. The nucleic acids of the invention can also be used as probes for hybridization in order to determine gene expression in various tumors and normal tissues, to identify the distribution of the gene expression.

When the nucleic acid of the invention is used as a probe for hybridization, there are no particular limitations on the actual method of hybridization. As preferred methods there may be mentioned, for example, Northern hybridization, Southern hybridization, colony hybridization, dot hybridization, fluorescence in situ hybridization (FISH), in situ hybridization (ISH), DNA chip methods, and microarray methods.

As one application example of the hybridization, the nucleic acid of this invention can be used as a probe for Northern hybridization to measure the length of mRNA or to quantitatively detect gene expression in an assayed sample.

When the nucleic acid of the invention is used as a probe for Southern hybridization, it enables the detection of the presence or absence of the nucleic acid in the genomic DNA of an assayed sample.

The nucleic acid of the invention can also be used as a probe for fluorescence in situ hybridization (FISH) to identify the location of the gene on a chromosome.

The nucleic acid of the invention can also be used as a probe for in situ hybridization (ISH) to identify the tissue distribution of gene expression.

When the nucleic acid of the invention is used as a probe for hybridization, a base length of at least 40 is necessary; and among the nucleic acids of the invention, a nucleic acid having a base length of 40 or more contiguous bases is preferably used. More preferably, one having a base length of 60 or more bases is used.

Nucleic acid probe techniques are well known to one skilled in the art, and for example, conditions suitable for hybridization between a probe of specific length according to this invention and the target polynucleotide may be readily determined. In order to obtain hybridization conditions optimal to probes of various lengths, Sambrook et al. "Molecular Cloning: A Laboratory Manual, 2nd Edition, Cold Spring Harbor (1989)" may be followed for such manipulations which are well known to one skilled in the art.

The probe of the invention is preferably labeled in an easily detectable fashion. The detectable label may be any type or portion which can be detected either visually or using devices. As commonly used detectable labels there may be mentioned radioactive isotopes such as $^{32}P$, $^{14}C$, $^{125}I$, $^{3}H$ and $^{35}S$ Biotin-labeled nucleotides may be incorporated into DNA or RNA by nick translation, or chemical or enzymatic means. The biotin-labeled probes are detected after hybridization using labeling means such as avidin/streptavidin, fluorescent labels, enzymes, gold colloidal complexes or the like. The nucleic acid may also be labeled by binding with a protein. Nucleic acid cross-linked to a radioactive or fluorescent histone single-stranded DNA binding protein may also be used.

(2) Primers for use in PCR

For other possible methods of detecting target genes, a primer may be designed after any sequence contained in a nucleic acid of this invention and can be used in a polymerase chain reaction (PCR). For example, RNA may be extracted from a sample to be assayed, and the gene expression can be semi-quantitatively measured by RT-PCR. Such method may be carried out by a technique well known to one skilled in the art. For example, "Molecular Cloning: A Laboratory Manual," (T. Maniatis, Cold Spring Harbor Laboratory Press) or Idenshibyo Nyumon [Introduction to Genetic Diseases] (Takahisa, S.: Nankodo Publishing) may be followed.

When a nucleic acid of this invention is used as a PCR primer, a base length of 10 to 60 is necessary; and among the nucleic acids of the invention, the nucleic acid having 10 to 60 contiguous bases is preferably used. More preferably, one having 15 to 30 bases is used. Generally, a primer sequence with a GC content of 40-60% is preferred. Also, there is preferably no difference in the Tm values of the two primers used for amplification. Preferably there is no annealing at the 3' ends of the primers and no secondary structure is formed in the primers.

(3) Nucleic Acid Screening

The nucleic acid of this invention can also be used to detect the expression distribution of a target gene which is expressed in various tissues or cells. The detection of expression distribution of the target gene can be accomplished, for example, by using the nucleic acid of the invention as a probe for hybridization or as a primer for PCR.

The expression distribution of a gene can also be detected using a DNA chip, microarray or the like. That is, the nucleic acid of the invention may be directly attached to the chip or array. There is known a method by which nucleic acids or others (DNA) are spotted to a substrate for the purpose of attaching them to a chip or array by using a high-precision dispenser (for example, see U.S. Pat. No. 5,807,522). RNA extracted from a clinical tissue may be labeled with a fluorescent substance or the like, hybridized, and an analysis can be made of the type of tissue cells with high expression of the gene. The DNA attached to the chip or the array may be the reaction product of PCR using the nucleic acid of the invention or a fragment thereof. As an alternative method, the nucleic acid fragment of the invention (DNA fragment) may be directly synthesized on a substrate to form a DNA chip or a DNA array (See, for example, U.S. Pat. No. 5,424,186).

By utilizing the aforementioned technology, it is possible to use as a diagnostic agent, at least one among the nucleic acids of this invention. In recent years, it has becoming clear that the genetic information possessed by individuals governs their susceptibility to a certain disease as well as governs the effectiveness of a particular drug. The DNA chips or microarrays produced using the aforementioned nucleic acids may be used to clarify the cause-effect relationship between the disease of a subject and the nucleic acid, which will enable not only the diagnosis of that disease but also the selection of a drug to be administered. Specifically, if the result detected using the DNA chip or microarray is employed as an indicator of selection of a drug to be administered, the expression level of one nucleic acid among the nucleic acids of the invention can be examined, but also the expression levels of two or more nucleic acids can be comparatively examined to select the drug to be administered, which will then enable more accurate judgment. As used herein, the disease is not particularly limited insofar as it is that which can be diagnosed by the nucleic acids of this invention. The disease is preferably a cancer-related disorder, more preferably liver cancer, breast cancer, kidney cancer, gastric cancer, ovarian cancer and thyroid cancer, and most preferably hepatoblastoma.

(4) DNA Cloning

The nucleic acid of invention can be at least used for cloning a gene which is expressed in human hepatoblastoma. For example, by using the nucleic acid of the invention as a probe for Northern hybridization or colony hybridization, or as a primer for PCR, cloning of a gene containing the nucleic acid of the invention is possible.

(5) Methods of Diagnosing Tumor Prognosis and Tumor Markers to be Used Therefor

The nucleic acid of this invention can be used as a probe for hybridization, or as a primer for PCR to determine the presence or absence of enhancement in expression of the target gene in sample cells, which enables the diagnosis of hepatoblastoma. To determine the presence or absence of enhancement in the gene expression, any method that utilizes probes capable of hybridizing to any portion contained in the nucleic acid of the invention is provided for use. Specifically, a sample cell can be diagnosed as a cell derived from hepatoblastoma if the amount of nucleic acid hybridizing to the probe sequence in the sample cell is in accord with the expression profile of the probe. When the nucleic acid is used as a primer for PCR, RNA is extracted from the sample to be assayed and the gene expression can be semi-quantitatively measured by the RT-PCR method, for example.

According to another embodiment of this invention there are provided antisense oligonucleotides against the nucleic acids of the invention. The antisense oligonucleotides are capable of hybridizing to the nucleic acids of the invention, and include antisense DNAs and antisense RNAs. Antisense DNA inhibits transcription of mRNA from DNA, while antisense RNA inhibits translation of mRNA. Such antisense oligonucleotides may be synthesized using an automated synthesizer or by PCR using the nucleic acid of the invention as a template. The antisense oligonucleotides also encompass antisense oligonucleotide derivatives having improved binding affinity for DNA or mRNA, tissue selectivity, cell permeability, nuclease resistance and intracellular stability. Such derivatives may be synthesized using antisense technology known in the art.

Antisense oligonucleotides having sequences complementary to the sequences near the translation initiation codon of the mRNA, those of the ribosome-binding site, and those of the capping site or the splicing site are capable of inhibiting synthesis of the RNA and therefore will exhibit a particularly notable inhibitory effect on gene expression. This invention, therefore, encompasses such antisense oligonucleotides.

(7) Gene Therapy

According to a further embodiment of this invention, there are provided therapeutic genes to be used in gene therapy. As will be considered in practicing this invention, the nucleic acid encoding the gene according to this invention may be transferred into a vector for use in gene transportation, whereby the transgene can be expressed by an arbitrary expression promoter and can be used for the gene therapy of cancers, for example.

1. Vectors

The transferable viral vectors may be prepared from DNA viruses or RNA viruses. They may be any viral vector of an MoMLV vector, a herpes virus vector, an Adenovirus vector, an AAV vector, a HIV vector, a SIV vector, a Seidai virus vector and the like. One or more proteins among the constituent protein group of a viral vector are substituted by the constituent proteins of a different species of virus, or alternatively a part of the base sequence constituting genetic information is substituted by the base sequence of a different species of virus to form a viral vector of the pseudo-type which can also be used in this invention. For example, there is mentioned a pseudo-type viral vector wherein the Env protein (an envelop protein of HIV) is substituted by the VSV-G protein (an envelop protein of vesicular stomatitis virus or VSV) (Naldini L., et al., Science 272, 263-267, 1996). Further, a virus having a host spectrum other than human is usable as the viral vector insofar as it is efficacious. As for the vectors other than those of viral origin, there may be used complexes of calcium phosphate and nucleic acid, ribosomes, cation-lipid complexes, Seidai virus liposomes, polymer carriers having polycation as the backbone main chain and others. In addition, methods such as electroporation and gene guns may be used as a gene transfer system.

2. Expression Promoters

As for the expression cassettes to be used for the therapeutic gene, any cassettes without any particular limitations may be used insofar as they can cause genes to express in the target cells. One skilled in the art can readily select such expression cassettes. Preferably, they are expression cassettes capable of gene expression in the cells derived from an animal, more preferably, expression cassettes capable of gene expression in the cells derived from a mammal, and most preferably expression cassettes capable of gene expression in the cells derived from a human. The gene promoters that can be used as expression cassettes include: for example, virus-derived promoters from an Adenovirus, a cytomegalovirus, a human immunodeficiency virus, a simian virus 40, a Rous sarcoma virus, a herpes simplex virus, a murine leukemia virus, a sinbis virus, a hepatitis type A virus, a hepatitis type B virus, a hepatitis type C virus, a papilloma virus, a human T cell leukemia virus, an influenza virus, a Japanese encephalitis virus, a JC virus, parbovirus B19, a poliovirus, and the like; mammal-derived promoters such as albumin, SR $\alpha$, a heat shock protein, and an elongation factor; chimera type promoters such as a CAG promoter; and the promoters whose expression can be induced by tetracyclines, steroids and the like.

(8) Marker Proteins for Detection of Hepatoblastoma

The protein encoded by the nucleic acid of this invention comprising any one of base sequences set forth in SEQ ID NO:1 to SEQ ID NO:104 in the Sequence Listing can be used as a marker protein for hepatoblastoma by detecting the protein in blood or a liver tissue of a patient suspected of having hepatoblastoma or by measuring the expression level of the protein. Specifically, the protein in the blood collected from the patient may be detected according to a known method that is commonly used for protein detection.

As described above, the nucleic acid of this invention, the protein encoded by the nucleic acid, or the information obtained from the foregoing can be utilized to diagnose whether or not the clinical tissue to be an assayable sample has been derived from hepatoblastoma. The gene, the protein or the information obtained from the foregoing can be utilized to design a tumor marker useful for the diagnosis of hepatoblastoma.

EXAMPLES

This invention will now be explained in greater detail by way of the examples; however, the invention will not be restricted to those example.

Preparation Example 1

Clinical Tissue of Hepatoblastoma

The clinical tissues of hepatoblastoma and normal liver were provided by the tissue bank from JPLT (Japanese Pediatric Liver Tumor Study Group), which were used. The normal liver was prepared by extracting a normal portion of the same liver from which the hepatoblastoma tissue had been extracted. The patients were treated at different hospitals and facilities under the coordination of JPLT during 1991 to 2001. Tissue specimens were frozen during surgery and then preserved at −80° C. prior to use.

Preparation Example 2

Extraction of Total RNA from the Clinical Tissues of Hepatoblastoma and Normal Liver Total RNA Extraction Kit (QIAGEN Inc.) was used to extract the total RNAs from the human hepatoblastoma clinical tissue and the normal liver clinical tissue. The extracted total RNAs were purified with phenol/chloroform, after which their concentrations were determined.

Example 1

Construction of cDNA Libraries cDNA libraries were constructed from the total RNAs which had been prepared from the clinical tissues in Preparation Example 1, according to the oligo capping method (Suzuki et al., Gene. 1997 October 24; 200(1-2): 149-56). They were two libraries (HMFT and HYST) derived from a human hepatoblastoma tissue which secreted AFP, a library (HKMT) derived from a human hepatoblastoma tissue which did not secret AFP, and a library (HMFN) derived from the corresponding infant normal liver tissue. The obtained cDNA libraries were used for transformation into *E. coli* (TOP-10, Invitrogen Corporation).

Example 2

Analysis of Both End Sequences of cDNAs

With respect to the *E. coli* cell prepared in Example 1, approximately 3000 clones each were picked up from the three types of cDNA libraries derived from the hepatoblastoma and from one type of cDNA library derived from the normal liver and end-sequencing was performed. Plasmid DNAs were extracted from the picked up *E. coli*. cell and both end sequences of the cDNAs were determined using a DNA Sequencing Kit (ABI). Specifically, there were combined 600 ng of plasmid DNA, 8 μl of premix (kit accessory) and 3.2 pmol of primers, and sterile distilled water was added to a total of 20 μl. After denaturing the mixture at 96° C. for 2 minutes, a cycle of 96° C. for 10 seconds, 50° C. for 5 seconds and 60° C. for 4 minutes was repeated 25 times for reaction. The products were then purified by ethanol precipitation. Sequencing was carried out by polyacrylamide gel electrophoresis under denaturing conditions, using ABI377 (ABI).

Example 3

Homology Search Using Database

An Internet-mediated DNA sequence homology search was conducted for the cDNA samples of which the both end-sequences were analyzed in Example 2. The search was conducted using the BLAST of the NCBI (National Center of Biotechnology Information, USA). Primers were designed for the clones that turned out to be novel genes as a result of the homology search.

The results obtained through Examples 1-3 are summarized in Table 1.

TABLE 1

| cDNA library | the number of clones | the number of genes with completed both end sequencing | the number of novel genes (percentage) |
|---|---|---|---|
| HMFT, HYST | 6,000 | 5,126 | 323 (6.3%) |
| HKMT | 3,000 | 2,537 | 262 (10.3%) |
| HMFN | 3,000 | 2,768 | 262 (9.5%) |
| total number | 12,000 | 10,431 | 847 (8.1%) |

Based on the obtained results from the homology search, the expression profiles of the known genes were compared between the hepatoblastoma tissue and the normal liver tissue. In both of the hepatoblastoma (HMFT and HYST in the presence of AFP) and the normal liver (HMFN), albumin was expressed most abundantly. Needless to indicate, in the former case AFP was expressed next to albumin; in the latter case cytochrome P450 was expressed next to albumin. The hepatoblastoma that did not secrete AFP (HKMT) and the hepatoblastoma that secreted AFP (HMFT and HYST) have different expression profiles. While Wnt inhibiting factor 1, which is a Wnt signal inhibiting factor 1, (Accession No. NM_007191) and dickkopf-1 (Accession No. BC001539) were expressed in the former case, they were scarcely expressed in the latter case.

Example 4

Mutation Screening of β-Catenin

The mutation screening of β-catenin was carried out on the genomic DNAs obtained from the hepatoblastoma clinical tissue and the normal liver clinical tissue according to the method by Takayasu et al. (Takayasu et al., Clin. Cancer Res. 2001, April; 7 (4): 901-908). Specifically, these genomic DNAs were used as templates to perform PCR that amplified a part of Exon 3 of β-catenin. The primers used were 5'-AAAAATCCAGCGTGGACAATGG-3' (ex3-2f: SEQ ID NO:105) and 5'-TGTGGCAAGTTCTGCATCATC-3' (ex3-2r: SEQ ID NO:106).

To conduct mutation screening for the coding region of β-catenin five kinds of primer sets described below were used to perform RT-PCR.

```
IDP1f: 5'-GAAAATCCAGCGTGGACAAT-3'  (SEQ ID NO:107)
IDP1r: 5'-CATCTGAGGAGAACGCATGA-3'  (SEQ ID NO:108)
IDP2f: 5'-TGCAATCCCTGAAACTGACAA-3' (SEQ ID NO:109)
IDP2r: 5'-TCAGCACTCTGCTTGTGGTC-3'  (SEQ ID NO:110)
IDP3f: 5'-TACTGGCTAGTGGTGGACCC-3'  (SEQ ID NO:111)
IDP3r: 5'-AGTGGGATGGTGGGTGTAAG-3'  (SEQ ID NO:112)
IDP4f: 5'-TGCAGTTCGCCTTCACTATG-3'  (SEQ ID NO:113)
IDP4r: 5'-GCAGTCTCATTCCAAGCCAT-3'  (SEQ ID NO:114)
IDP5f: 5'-GAAACGGCTTTCAGTTGAGC-3'  (SEQ ID NO:115)
IDP5r: 5'-CTCGACCAAAAAGGACCAGA-3'  (SEQ ID NO:116)
```

For RT-PCR 30 μl of a mixed transcriptase solution containing 5 μg of total RNA prepared from the hepatoblastoma clinical tissue or the normal liver clinical tissue, 200 units of Superscript II reversetranscriptase (Life Technologies. Inc., Gaithersburg, Md.), 160 pmol of random primer (Takara Shuzo Co. Ltd.) was subjected to dissociation reaction at 65° C. for 15 minutes, after which incubation was carried out at 42° C. for 90 minutes. Subsequently, five kinds of primer sets described in Table 1 were, respectively, used to perform PCR. PCR was performed by subjecting a solution of 1 μM primer, 200 μM dNTPs, 50 mM KCl, 10 mM Tris-HCl (pH 8.3), 1.5 mM $MgCl_2$, and 1 unit Taq Polymerase (Boehringer Mannheim AG.) to a 35-cylce reaction with one cycle of 94° C. for 15 seconds, 60° C. for 15 seconds and 72° C. for 45 seconds.

The PCR products were electrophoresed on 2% agarose gel or 5% polyacrylamide gel to analyze the presence or the absence of deletion mutation. Concurrently, sequencing was conducted on all the PCR products to determine point mutation.

Example 5

RT-PCR

Four kinds of samples (Cases 10, 58, 77 and 85) for which the mutation in β-catenin was observed in Example 4 and four kinds of samples (Cases 14, 67, 78 and 81) for which the mutation in β-catenin was not observed in Example 4 were subjected to RT-PCR and cDNAs were synthesized, which were to be used as templates for later differential screening. RT-PCR was performed using a SuperScript II kit (Life Technologies Inc., Gaithersburg, Md.). Specifically, a solution containing 5 μg of RNA, 2 μl of random primers (10 μg/μl), and DEPC water added as required was incubated at 65° C. for 15 minutes and was placed on ice after reaction was completed. To this solution was added a mixed solution containing 6 μl of 5× buffer, 1 μl of 0.1 mM DTT, 7.5 μl of dNTPs and 1 μl of SuperScript II per sample. Reaction was allowed at 42° C. for 2 hours and then 95° C. for 5 minutes.

The prepared cDNAs were diluted 50-fold with DDW and then concentrations were adjusted with GAPDH primers. The base sequences of the GAPDH primers were as follows: 5'-ACCTGACCTGCCGTCTAGAA-3' (forward: SEQ ID NO:117) and 5'-TCCACCACCCTGTTGCTGTA-3' (reverse: SEQ ID NO:118). To 1 μl of cDNA were added each 5 μl of 10 μM the forward primer and the reverse primer, 1 μl of dNTPs, 6 μl of DDW, and 0.1 μl of rTaq polymerase, respectively, whereby a mixed solution was prepared. A 27-cylce PCR was performed at 95° C. for 15 seconds, 58° C. for 15 seconds and 72° C. for 20 seconds. The PCR products were electrophoresed on 1.5% agarose gel for 20 minutes to determine the concentrations.

Consequently, the samples diluted 50-fold with DDW were respectively further diluted to be almost even concentrations: 6-fold in Case 14t (hepatoblastoma), 2-fold in Case 14h (normal liver), 5-fold in Case 67t, 6-fold in Case 67h, 10-fold in Case 78t, 12-fold in Case 78h, 8-fold in Case 81t, 9-fold in Case 81h, 2-fold in Case 10t, 1-fold in Case 10h, 20-fold in Case 58t, 4-fold in Case 58h, 15-fold in Case 77t, 6-fold in Case 85t, and 2-fold in Case 85h.

Example 6

Differential Screening

Primers were designed for novel genes obtained from the cDNA libraries and differential screening was conducted using 8 pairs (or 16 samples) with the adjusted concentrations. For the reaction solution of PCR, to 1 μl of cDNA were mixed 10 μM of the forward and reverse primers respectively in 5 μl and 1 μl of 10× reaction buffers, 1 μl of dNTPs, 6 μl of DDW, and 0.1 μl of rTaq polymerase, which mixed solution was used. As for PCR annealing temperature, the reaction was subjected to PCR at three levels of annealing temperatures (57° C., 59° C. and 61° C.) and in 35 cycles, and then, the temperature at which the deepest color band appeared was employed as the annealing temperature of the primer. When no band appeared, the conditions were examined in a similar manner by subjecting the reaction to 40 cycles. Thus, the respective annealing temperatures and cycle numbers for the primers were determined.

PCR was performed at the thus determined annealing temperature. The PCR products obtained were electrophoresed on 1.5% agarose gel for 20 minutes and were stained with ethidium bromide, whereby the band concentrations were compared between the hepatoblastoma and the normal liver of the same patient.

Figure 2:
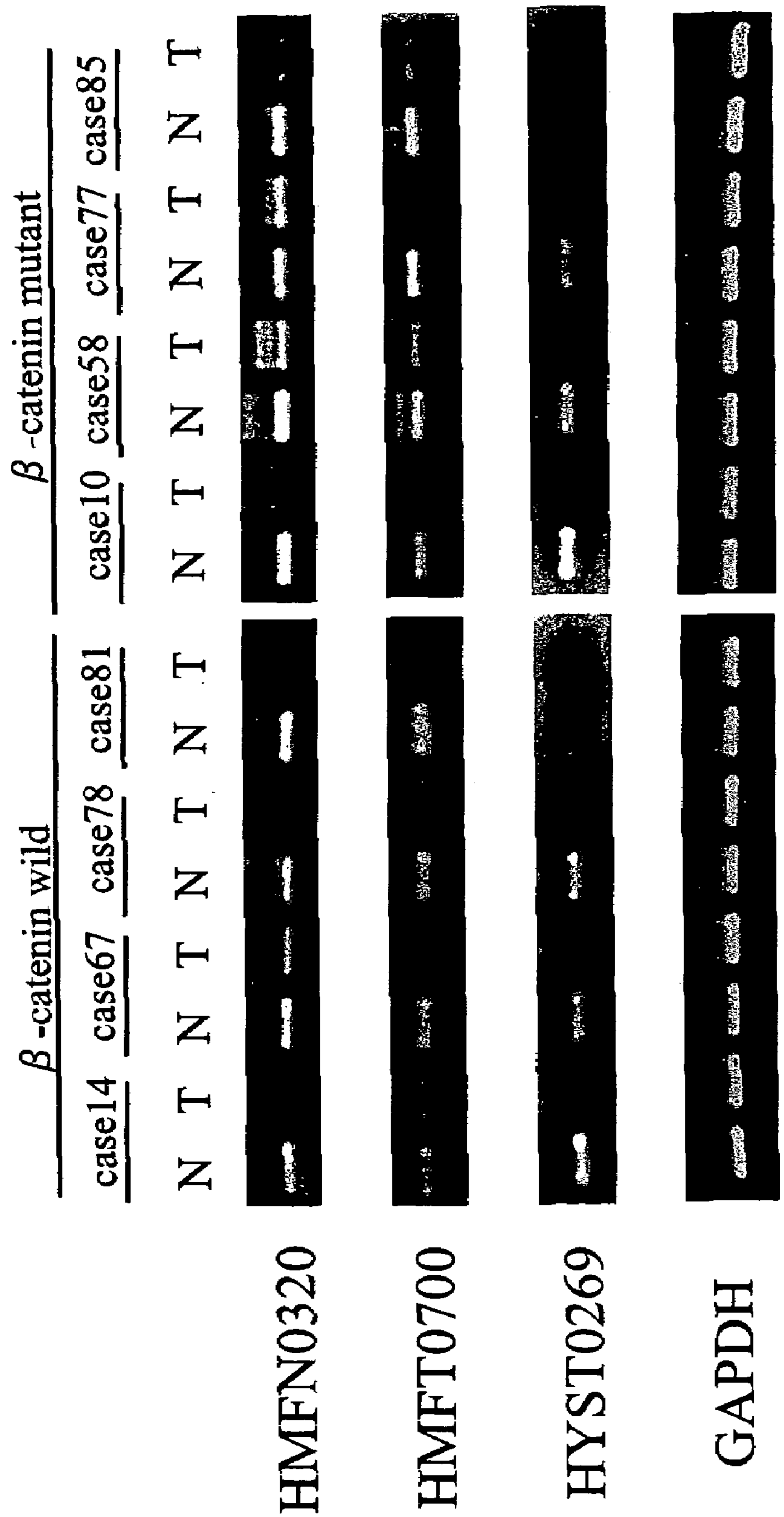
FIG. 2 is a figure corresponding to an electrophoregram showing another example of the results from differential screening by RT-PCR.
Figure 3:
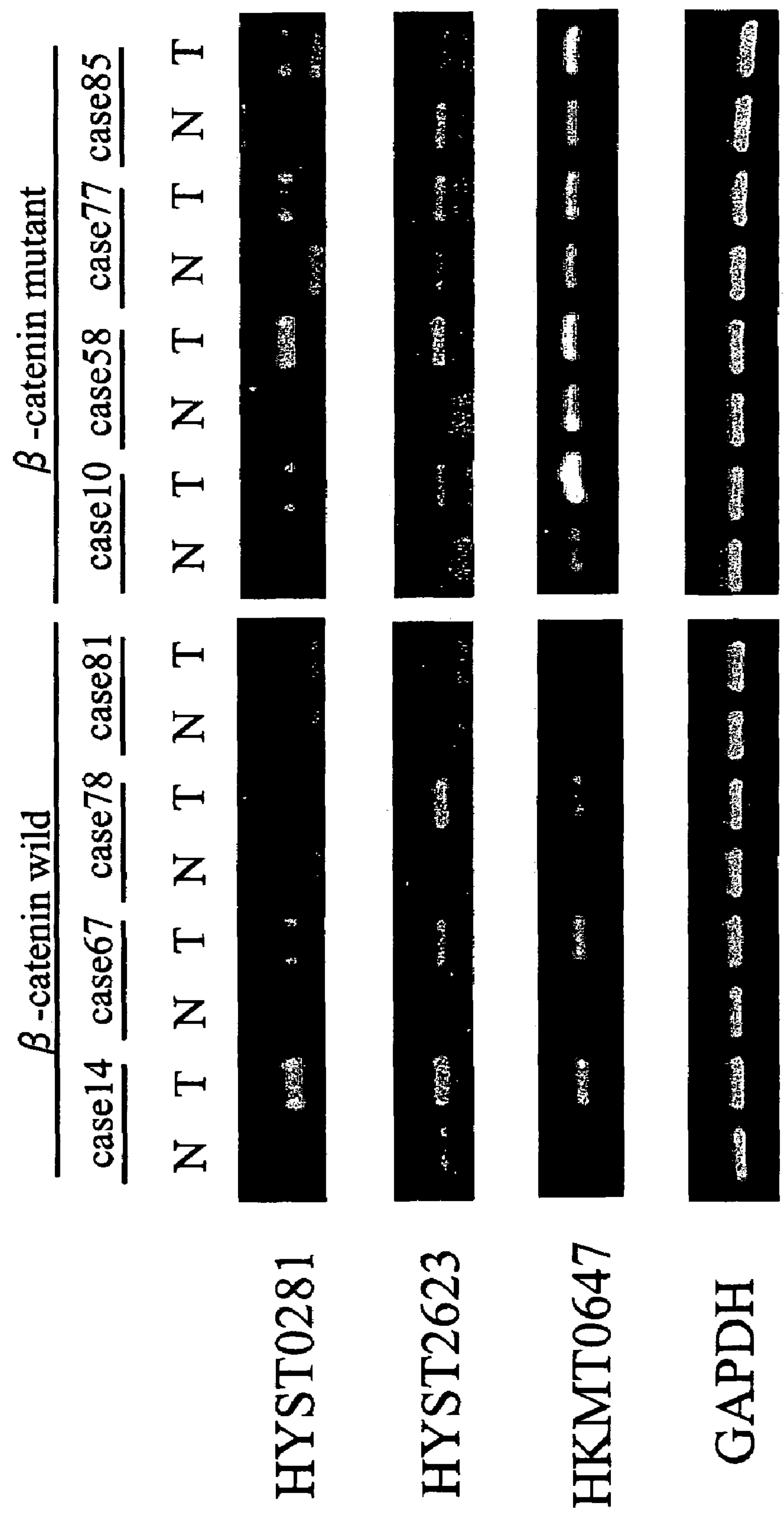
FIG. 3 is a figure corresponding to an electrophoregram showing a still further example of the results from differential screening by RT-PCR.

FIG. 1 shows one example of the electrophoresis patterns for four types of genes for which differential expression levels are noted in hepatoblastoma and normal liver based on comparison therebetween. FIGS. 2 and 3 show other examples. The expression level of each gene is normalized against the expression of GAPDH. In each figure Lane N corresponds to a normal liver tissue and Lane T corresponds to a hepatoblastoma tissue. However, Case 77 corresponds to a hepatocellular carcinoma tissue.

As the table below shows, in not less than 5 cases out of 8 cases reproducibility was confirmed on the genes for which strong expression had been observed in the hepatoblastoma (regardless of the β-catenin mutation) or the normal liver. The genes for which reproducibility was confirmed were judged to be the genes having differences in hepatoblastoma and normal liver based on comparison therebetween. In the tables below N<T shows that expression is high in the hepatoblastoma tissue; N>T shows that expression is high in the normal liver tissue; and N=T shows that the expression levels are almost the same in the hepatoblastoma tissue and the normal liver tissue.

TABLE 2

| | case14 | case67 | case78 | case81 | case10 | case58 | case77 | case85 | total | annealing temperature | cycle |
|---|---|---|---|---|---|---|---|---|---|---|---|
| HKMT0647 | N < T | N < T | N < T | N < T | N < T | N = T | N < T | N < T | N < T in 7 cases | — | — |
| HKMT1098 | N > T | N = T | N < T | N < T | N > T | N > T | N > T | N > T | N > T in 5 cases | — | — |
| HKMT1188 | N < T | N < T | N = T | N < T | N < T | N < T | N < T | N > T | N < T in 6 cases | — | — |

TABLE 3

| | case14 | case67 | case78 | case81 | case10 | case58 | case77 | case85 | total | annealing temperature | cycle |
|---|---|---|---|---|---|---|---|---|---|---|---|
| HMFN0044 | N = T | N = T | N > T | N > T | N > T | N > T | N > T | N > T | N < T in 6 cases | — | — |
| HMFN0320 | N > T | N > T | N > T | N > T | N > T | N > T | N > T | N > T | N > T in 8 cases | — | — |
| HMFN0376 | N > T | N > T | N > T | N > T | N > T | N > T | N > T | N > T | N > T in 8 cases | 59 | 40 |
| HMFN0601 | N < T | N < T | N > T | N < T | N < T | N < T | N = T | N > T | N < T in 5 cases | 57 | 35 |
| HMFN0656 | N > T | N > T | N > T | N > T | N > T | N > T | N > T | N > T | N < T in 6 cases | 59 | 40 |
| HMFN0672 | N = T | N > T | N > T | N > T | N > T | N = T | N > T | N > T | N < T in 6 cases | 57 | 35 |
| HMFN0883 | N = T | N = T | N > T | N > T | N > T | N = T | N > T | N > T | N < T in 5 cases | — | — |
| HMFN1045 | N > T | N > T | N > T | N > T | N > T | N > T | N = T | N > T | N < T in 7 cases | 57 | 35 |
| HMFN1187 | N > T | N = T | N > T | N > T | N > T | N > T | N > T | N > T | N < T in 7 cases | — | — |
| HMFN1249 | N = T | N = T | N > T | N > T | N > T | N < T | N > T | N > T | N < T in 5 cases | — | — |
| HMFN1655 | N = T | N > T | N > T | N > T | N > T | N > T | N > T | N > T | N < T in 7 cases | 57 | 35 |
| HMFN1661 | N = T | N > T | N > T | N > T | N > T | N > T | N > T | N > T | N < T in 7 cases | 57 | 40 |
| HMFN1864 | N > T | N = T | N > T | N > T | N > T | N > T | N > T | N > T | N < T in 7 cases | 57 | 35 |
| HMFN1876 | N = T | N = T | N = T | N > T | N > T | N > T | N > T | N > T | N < T in 5 cases | 59 | 40 |
| HMFN2073 | N = T | N > T | N > T | N > T | N > T | N = T | N = T | N > T | N < T in 5 cases | — | — |

TABLE 3-continued

| | case14 | case67 | case78 | case81 | case10 | case58 | case77 | case85 | total | annealing temperature | cycle |
|---|---|---|---|---|---|---|---|---|---|---|---|
| HMFN2121 | N > T | N > T | N > T | N < T | N > T | N = T | N = T | N > T | N < T in 5 cases | — | — |
| HMFN2567 | N = T | N = T | N > T | N > T | N > T | N > T | N > T | N > T | N < T in 6 cases | — | — |
| HMFN2729 | N > T | N > T | N = T | N > T | N > T | N > T | N = T | N > T | N < T in 6 cases | — | — |

TABLE 4

| | case14 | case67 | case78 | case81 | case10 | case58 | case77 | case85 | total | annealing temperature | cycle |
|---|---|---|---|---|---|---|---|---|---|---|---|
| HMFT0128 | N > T | N > T | N > T | N > T | N > T | N > T | N > T | N > T | N > T in 8 cases | 57 | 40 |
| HMFT0141 | N > T | N > T | N > T | N > T | N > T | N > T | N > T | N > T | N > T in 8 cases | 61 | 40 |
| HMFT0656 | N > T | N < T | N > T | N < T | N > T | N > T | N > T | N > T | N > T in 6 cases | — | — |
| HMFT0673 | N > T | N = T | N > T | N > T | N > T | N > T | N > T | N > T | N > T in 7 cases | 57 | 35 |
| HMFT0700 | N > T | N > T | N > T | N > T | N > T | N > T | N > T | N > T | N > T in 8 cases | 61 | 35 |
| HMFT1272 | N > T | N > T | N > T | N > T | N > T | N = T | N = T | N > T | N > T in 6 cases | 61 | 40 |
| HMFT1488 | N < T | N > T | N > T | N > T | N > T | N > T | N > T | N > T | N > T in 7 cases | 57 | 35 |
| HMFT1638 | N > T | N > T | N > T | N > T | N > T | N > T | N > T | N = T | N > T in 7 cases | 57 | 35 |
| HMFT1716 | N > T | N > T | N > T | N > T | N > T | N > T | N > T | N = T | N > T in 7 cases | 61 | 35 |
| HMFT1766 | N = T | N = T | N > T | N > T | N > T | N > T | N > T | N > T | N > T in 6 cases | 57 | 35 |
| HMFT2263 | N > T | N > T | N > T | N > T | N > T | N = T | N > T | N > T | N > T in 7 cases | 57 | 40 |
| HMFT2489 | N = T | N > T | N > T | N > T | N > T | N = T | N > T | N = T | N > T in 5 cases | 57 | 35 |

TABLE 5

| | case14 | case67 | case78 | case81 | case10 | case58 | case77 | case85 | total | annealing temperature | cycle |
|---|---|---|---|---|---|---|---|---|---|---|---|
| HYST0269 | N > T | N > T | N > T | N > T | N > T | N > T | N > T | N > T | N > T in 8 cases | 57 | 35 |
| HYST0281 | N < T | N < T | N < T | N > T | N < T | N < T | N < T | N < T | N < T in 7 cases | 57 | 40 |
| HYST1031 | N > T | N > T | N > T | N > T | N > T | N > T | N < T | N = T | N > T in 6 cases | — | — |
| HYST1046 | N > T | N > T | N > T | N > T | N > T | N > T | N > T | N > T | N > T in 8 cases | 57 | 40 |
| HYST1888 | N = T | N = T | N = T | N > T | N > T | N > T | N > T | N > T | N > T in 5 cases | — | — |
| HYST2056 | N = T | N > T | N > T | N > T | N > T | N > T | N = T | N > T | N > T in 6 cases | — | — |
| HYST2477 | N = T | N = T | N > T | N > T | N > T | N > T | N > T | N > T | N > T in 6 cases | 57 | 35 |
| HYST2623 | N < T | N < T | N < T | N = T | N < T | N < T | N = T | N = T | N < T in 5 cases | — | — |

TABLE 6

| | case14 | case67 | case78 | case81 | case10 | case58 | case77 | case85 | total | annealing temperature | cycle |
|---|---|---|---|---|---|---|---|---|---|---|---|
| HMFT1163 | N = T | N < T | N < T | N < T | N > T | N < T | N > T | N > T | — | — | — |
| HMFT1345 | N = T | N < T | N < T | N < T | N > T | N = T | N > T | N > T | — | — | — |

In not less than 3 cases out of 4 cases where no mutation was observed in the β-catenin gene differential expressions were noted and in not less than 3 cases out of 4 cases where mutation was observed in the β-catenin gene differential expressions were noted in a manner opposite to the foregoing cases where no mutation was observed. Such genes were judged to have differential expressions depending on the presence of the β-catenin mutation (Table 6). That is, the genes described in Table 6 show such genotype that N<T holds when no mutation was observed in β-catenin and N>T holds when mutation was observed in β-catenin.

TABLE 7

| | case14 | case67 | case78 | case81 | case10 | case58 | case77 | case85 | total | annealing temperature | cycle |
|---|---|---|---|---|---|---|---|---|---|---|---|
| HKMT0020 | N < T | N < T | N > T | N < T | N < T | N < T | N < T | N = T | N < T in 7 cases | 57 | 35 |
| HKMT1013 | N > T | N = T | N > T | N > T | N > T | N > T | N = T | N > T | N > T in 5 cases | 57 | 35 |
| HKMT0359 | N = T | N = T | N > T | N > T | N > T | N > T | N > T | N = T | N < T in 6 cases | 57 | 35 |

TABLE 8

| | case14 | case67 | case78 | case81 | case10 | case58 | case77 | case85 | total | annealing temperature | cycle |
|---|---|---|---|---|---|---|---|---|---|---|---|
| HFMN0043 | N = T | N > T | N > T | N > T | N > T | N > T | N > T | N > T | N > T in 7 cases | 57 | 40 |
| HFMN0077 | N = T | N > T | N > T | N > T | N > T | N > T | N > T | N > T | N > T in 7 cases | 57 | 35 |
| HFMN0549 | N > T | N > T | N > T | N > T | N > T | N = T | N > T | N = T | N > T in 6 cases | 57 | 35 |
| HFMN1050 | N > T | N > T | N > T | N > T | N > T | N > T | N > T | N > T | N > T in 8 cases | — | — |
| HFMN2802 | N > T | N > T | N > T | N > T | N > T | N > T | N > T | N > T | N > T in 8 cases | — | — |

TABLE 9

| | case14 | case67 | case78 | case81 | case10 | case58 | case77 | case85 | total | annealing temperature | cycle |
|---|---|---|---|---|---|---|---|---|---|---|---|
| HMFT | N < T | N < T | N < T | N < T | N = T | N < T | N = T | N < T | N < T in 6 cases | 61 | 40 |
| HMFT | N > T | N = T | N > T | N > T | N > T | N > T | N > T | N > T | N > T in 7 cases | 61 | 35 |
| HMFT | N = T | N > T | N > T | N > T | N > T | N > T | N = T | N > T | N > T in 6 cases | 59 | 35 |
| HMFT | N = T | N = T | N > T | N > T | N > T | N > T | N > T | N > T | N > T in 6 cases | 57 | 35 |
| HMFT | N > T | N > T | N > T | N > T | N > T | N > T | N > T | N > T | N > T in 8 cases | 61 | 40 |
| HMFT | N > T | N > T | N > T | N > T | N > T | N > T | N > T | N = T | N > T in 7 cases | 57 | 35 |
| HMFT | N > T | N = T | N > T | N > T | N > T | N > T | N = T | N > T | N > T in 6 cases | 61 | 40 |
| HMFT | N > T | N = T | N > T | N > T | N > T | N > T | N > T | N = T | N > T in 5 cases | 61 | 35 |
| HMFT | N > T | N < T | N > T | N > T | N > T | N > T | N > T | N > T | N > T in 7 cases | 57 | 35 |
| HMFT | N > T | N > T | N > T | N > T | N > T | N > T | N > T | N > T | N > T in 8 cases | 59 | 35 |
| HMFT | N > T | N > T | N > T | N > T | N > T | N > T | N > T | N > T | N > T in 8 cases | 59 | 35 |

TABLE 10

| | case14 | case67 | case78 | case81 | case10 | case58 | case77 | case85 | total | annealing temperature | cycle |
|---|---|---|---|---|---|---|---|---|---|---|---|
| HYST0078 | N < T | N < T | N > T | N > T | N > T | N = T | N > T | N > T | N > T in 5 cases | 57 | 35 |
| HYST2010 | N > T | N > T | N > T | N > T | N > T | N = T | N = T | N > T | N > T in 6 cases | 57 | 35 |
| HYST2465 | N = T | N = T | N > T | N > T | N > T | N = T | N > T | N > T | N > T in 5 cases | 59 | 35 |

TABLE 11

| clone | Acc. No. | gene |
|---|---|---|
| HKMT0020 | NM_006325 | *Homo sapiens* RAN, member RAS oncogene family (RAN), mRNA |
| HKMT0359 | NM_005079 | *Homo sapiens* tumor protein D52 (TPD52), mRNA |
| HKMT1013 | HM_000598 | *Homo sapiens* insulin-like growth factor binding protein 3 (IGFBP3), mRNA |
| HMFN0043 | X03178 | Human mRNA for group-specific component (GC) |
| HMFN0077 | K01763 | Human haptoglobin alpha(1S)-beta precursor, mRNA |
| HMFN0722 | AF153821 | *Homo sapiens* alcohol dehydrogenase beta2 subunit mRNA, complete cds |
| HMFN1050 | D45045 | Human DNA for ceruloplasmin, exon 19 |
| HMFN2802 | XM_006765 | *Homo sapiens* microsomal NAD+-dependent retinol dehydrogenase 4 (RODH-4), mRNA |
| HMFT0048 | X73458 | *H. sapiens* plk-1 mRNA |
| HMFT0306 | D49742 | Human mRNA for HGF activator like protein, complete cds |
| HMFT0550 | AF171237 | *Homo sapiens* clone A2-53-73 3-phosphoglycerate dehydrogenase (PGDH3) mRNA, alternatively spliced, complete cds |
| HMFT0609 | AF052153 | *Homo sapiens* clone 24441 cytosolic aspartate aminotransferase mRNA, partial cds |
| HMFT0716 | X14174 | Human mRNA for liver-type alkaline phosphatase (EC 3.1.3.1) |
| HMFT0844 | AF177775 | *Homo sapiens* egasyn mRNA, complete cds |
| HMFT1154 | Z28339 | *H. sapiens* mRNA for delta 4-3-oxosteroid 5 beta-reductase |
| HMFT1198 | M13755 | Human interferon-induced 17-kDa/15-kDa protein mRNA, complete cds |
| HMFT1264 | M81349 | *H. sapiens* serum amyloid A protein mRNA, complete cds |
| HMFT1599 | X56692 | *H. sapiens* mRNA for C-reactive protein |
| HMFT1603 | L21893 | Human Na/taurocholate cotransporting polypeptide mRNA, complete cds |
| HYST0078 | L32179 | Human arylacetamide deacetylase mRNA, complete cds |
| HYST2010 | X03168 | Human mRNA for S-protein |
| HYST2465 | S82800 | IHRP = inter-alpha-trypsin inhibitor family heavy chain-related protein/major acute phase serum protein [swine, liver, mRNA Partial, 2952 nt] |

The genes described in Tables 7-10 are known genes. Table 11 describes the names of genes for which homologies to the named genes were recognized as a result of homology search.

The genes described in Table 12 are also novel and are genes for which differential expression levels are noted hepatoblastoma and normal liver based on comparison therebetween in accordance with the above-mentioned criteria. The full length of each of these genes was not sequenced except for HMFN0839. However, as a result of both end sequencing and homology search, they were found to have homology to the respective known genes shown in Table 13.

TABLE 12

| | Case14 | Case67 | Case78 | Case81 | Case10 | Case58 | Case77 | Case85 |
|---|---|---|---|---|---|---|---|---|
| HMFN0217 | N = T | N = T | N > T | N > T | N > T | N > T | N > T | N > T |
| HMFN0668 | N = T | N > T | N > T | N > T | N > T | N > T | N = T | N > T |
| HMFN0839 | N = T | N > T | N > T | N > T | N > T | N > T | N = T | N > T |
| HMFN2700 | N > T | N > T | N > T | N > T | N > T | N > T | N = T | N > T |
| HKMT2698 | N > T | N = T | N > T | N = T | N > T | N = T | N > T | N > T |
| HYST2198 | N < T | N < T | N < T | N < T | N = T | N > T | N < T | N > T |
| HYST2935 | N < T | N < T | N < T | N = T | N < T | N < T | N = T | N = T |
| HMFT1511 | N > T | N = T | N > T | N > T | N > T | N > T | N > T | N > T |

TABLE 13

| clone | length | Acc. No. | gene |
|---|---|---|---|
| HMFN0217f | 510 | AP000356 | *Homo sapiens* genomic DNA, chromosome 22q11.2, clone KB1995A5 |
| HMFN0668f | 666 | 548898\|sp\| P36536 | SARA_MOUSE GTP-binding protein SARA |
| HMFN0668r | 597 | AW976405 | EST388514 MAGE resequences, MAGN *Homo sapiens* cDNA, mRNA sequence |
| HMFN0839f | 531 | T24032 | hypothetical protein R07E3.5 *Caenorhabditis elegans* |
| HMFN0839r | 607 | BE349224 | *Homo sapiens* cDNA clone |
| HMFN2700f | 429 | | |
| HKMT2698f | 420 | AR083267 | Sequence 19 in U.S. Pat. No. 5976837 |
| HKMT2698r | 517 | AR083267 | Sequence 19 in U.S. Pat. No. 5976837 |
| HYST2198f | 484 | AK024066 | *Homo sapiens* cDNA FLJ14004 fis., clone Y79AA1002351 |
| HYST2935f | 564 | BF345917 | *Homo sapiens* cDNA clone 602017918F1 |
| HMFT1511f | 401 | AW786459 | *Sus scrofa* cDNA 5', mRNA sequence |
| HMFT1511r | 466 | AP000359 | *Homo sapiens* genomic DNA, chromosome 22q11.2, clone KB63E7 |

Example 7

Differential Screening of Plk-1

Figure 4:
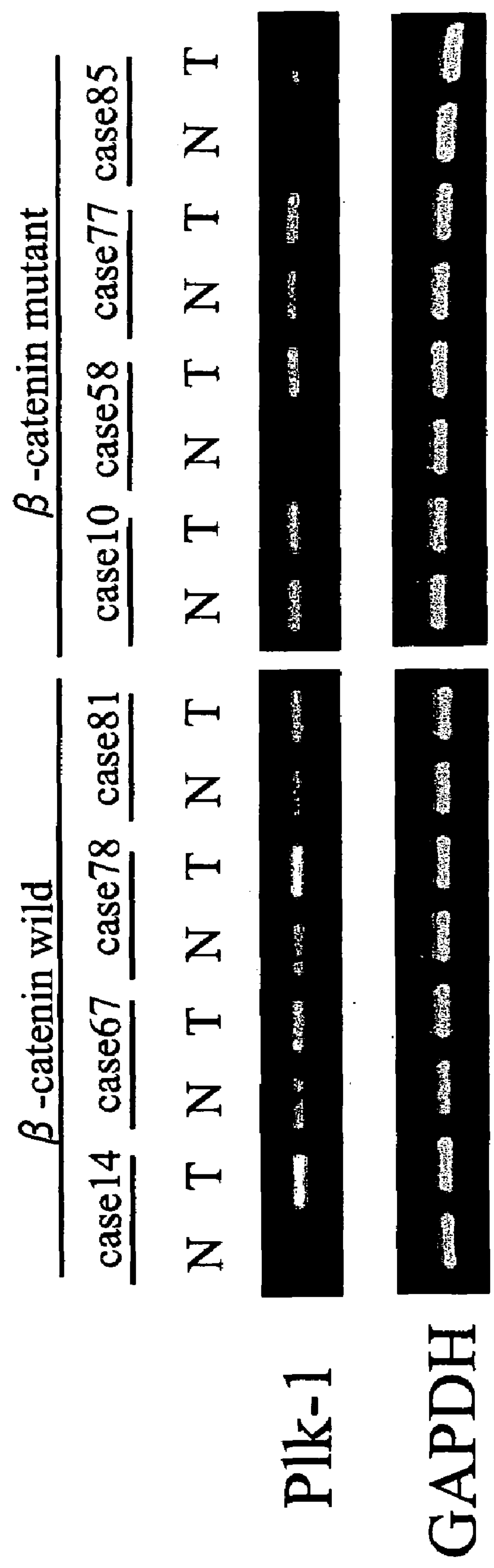
FIG. 4 is a figure corresponding to an electrophoregram showing an example of Plk-1 gene resulting from differential screening by RT-PCR.

Similarly to Example 6, a semi-quantitative RT-PCR was performed and the expression of Plk-1 was confirmed in 8 pairs (16 samples). Results are shown in FIG. 4. Here, the expression levels of the Plk-1 gene were normalized against the expression of GAPDH. In the figure Lane N corresponds to the normal liver tissue and Lane T corresponds to the hepatoblastoma. However, Case 77 corresponds to the hepatocellular carcinoma tissue. The expression level of Plk-1 was clearly greater in the tumor tissue than in the normal tissue.

Example 8

Northern Blotting

Figure 5:
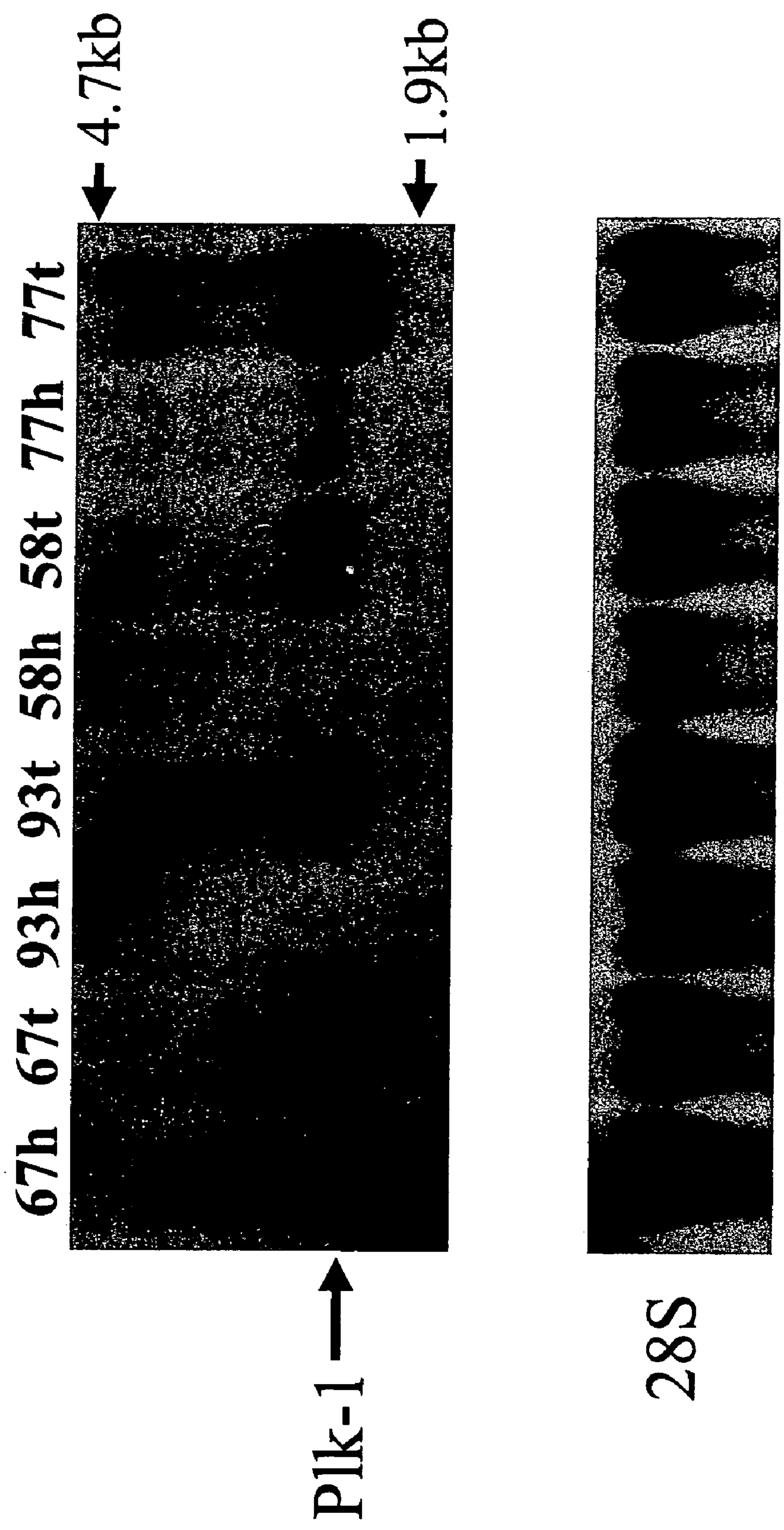
FIG. 5 is a figure of Northern blotting in which the expression of Plk-1 was examined in a hepatoblastoma tissue and a normal liver tissue.

Total RNA (25 μg) was prepared from human hepatoblastoma, hepatocellular carcinoma and normal liver according to a conventional method (Chomczynski P., Sacchi N., Anal. Biochem., 162: 156-9, 1987). This was electrophoresed on 1% agarose gel containing formaldehyde and fixed through UV cross-linking. Hybridization was conducted in the presence of a human Plk-1 cDNA fragment labeled with α-$^{32}$P-dCTP Random (976 bases) using random priming: 65° C. in a solution containing 1M NaCl, 1% SDS, 7.5% dextran sulfate, 100 μg/ml thermally denatured salmon serum. Results are shown in FIG. 5. In the figure 67t, 93t and 58t are the human hepatoblastoma tissue and 67h, 93h and 58h are the corresponding normal liver tissues, 77t is the hepatocellular carcinoma tissue, and 77h is the corresponding normal liver tissue. It is understood that the expression of Plk-1 is higher in both the human hepatoblastoma and the hepatocellular carcinoma tissues than the normal liver tissue.

Example 9

Statistical Analysis of Prognosis

Figure 6:
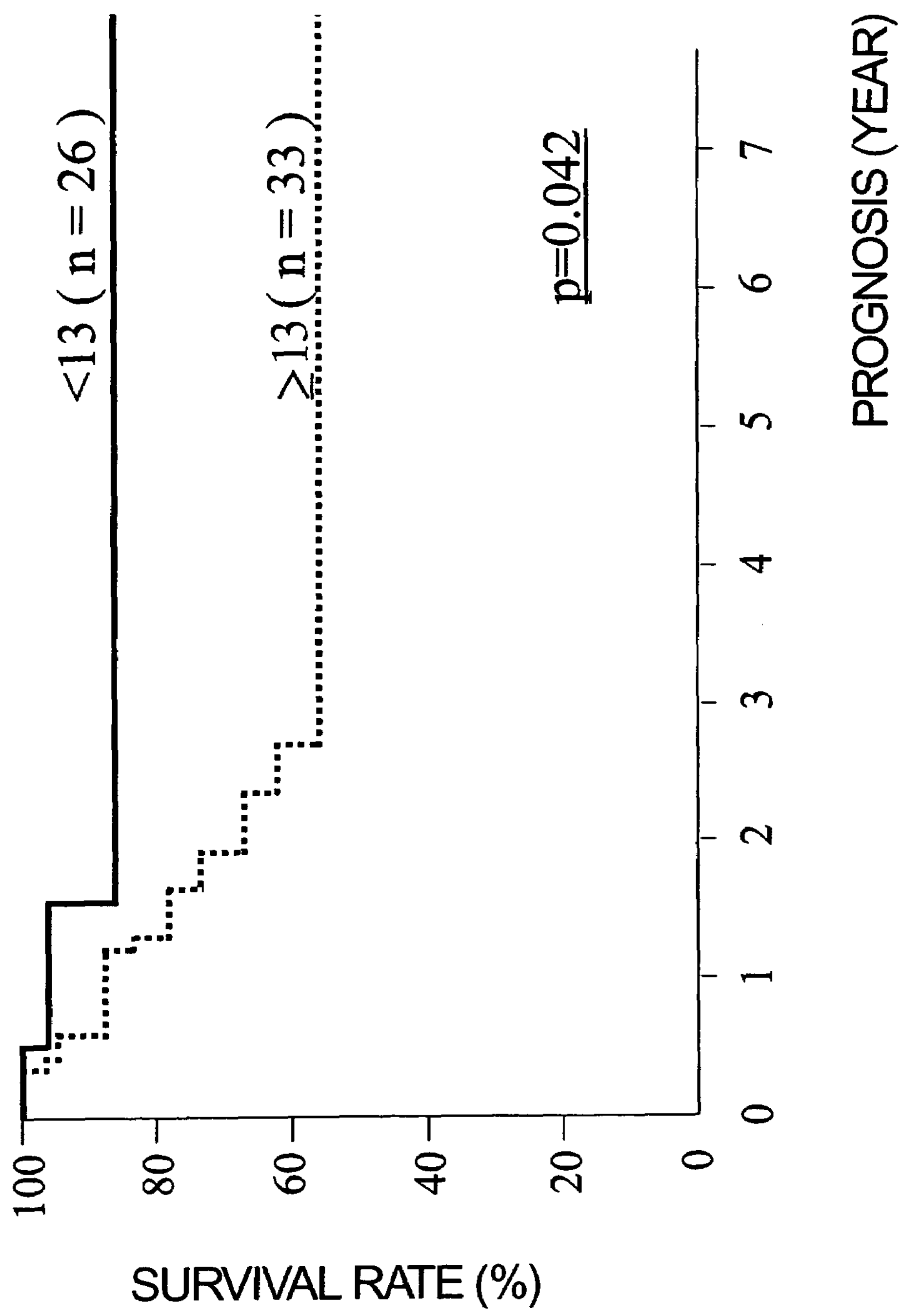
FIG. 6 is a Kaplan-Meier curve plot showing the survival rates of hepatoblastoma patients.

A Kaplan-Meier analysis of 59 cases of hepatoblastoma patients was attempted using the expression levels of Plk-1 as indices around the central value of Plk-1 expression level=13. The results of analysis are shown in FIG. 6. The patients with high Plk-1 expression showed more unfavorable prognosis than do the patients with low PLk-1 expression. The survival rate of the former group is 55.9% while that of the latter group is 87.0% (with statistical significance being p=0.042). Therefore, it has been demonstrated that the expression level of the Plk-1 gene is an excellent marker for the diagnosis of prognosis of human hepatoblastoma.

INDUSTRIAL APPLICABILITY

As described above, this invention discloses gene sequences displaying differential expression levels between hepatoblastoma and normal liver and will enable the provision of their genetic information and the diagnosis of hepatoblastoma by utilizing the nucleic acids and proteins according to the invention derivable from the genetic information as probes and PCR primers.

The invention claimed is:

1. An isolated nucleic acid consisting of SEQ ID NO:56.

* * * * *

SEQUENCE LISTING

<160> NUMBER OF SEQ ID NOS: 118

<210> SEQ ID NO 1
<211> LENGTH: 1996
<212> TYPE: DNA
<213> ORGANISM: Homo sapiens
<220> FEATURE:
<223> OTHER INFORMATION: hkmt-0647

<400> SEQUENCE: 1

```
gcctgtacgg aagtgttact tctgctctaa aagctgcgga attcctcgag cactgttggc     60

ctactggatg tataattgca ggaatttttt tttattttt tattttccat cattctatat     120

atgtgatggt gaaagatatg cctggaaaag ttttgttttg aaaagtttat tttctgcttc    180

gtcttcagtt ggcaaaagct ctcaattctt tagcttccag tttcttttct ctctttttct    240

ttgttaggta attaaaggta tgtaaacaaa ttatctcatg tagcagggga ttttcatgtt    300

gagaggaatc ttccgtgtga gttgtttggt cacacaaata accctttctc aattttagga    360

gtttggattg tcaaatgtag gtttttctca aagggggcat ataactacat attgactgcc    420

aagaactatg actgtagcac taatcagcac acatagagcc acacaattat ttaatttcta    480

actctctgtg gtccctagaa aaattccgtt gatgtgctta ggttaaagtt ctgaagatac    540

ccgttgtacc cttacttgaa agtttctaat cttaagtttt atgaaatgca ataatatgta    600

tcagctagca atatttctgt gatcaccaac aactctcagt ttgatcttaa agtctgaata    660

ataaaacaaa tcccagcagt aatacatttc ttaaacctca cagtgcatga tatatctttt    720

cattctgatc ctgtgtttgc aaaaatatac acatgtatat catagttcct cactttttat    780

tcatttgttt tcctattacc tgtagtaaat atattagtta gtacatggaa tttatagcat    840

cagctacccc caggaacagc acctgacagg cgggggattt tttttcaagt tgttctacat    900

ttgcataaat tatttctatt attattcatg tatgttattt atttctgaat cacactagtc    960

ctgtgaaagt acaactgaag gcagaaagtg ttaggatttt gcatctaatg ttcattatca   1020

tggtattgat ggacctaaga aaataaaaat tagactaagc ccccaaataa gctgcatgca   1080

tttgtaacat gattagtaga tttgaatata tagatgtagt attttgggta tctaggtgtt   1140

ttatcattat gtaaaggaat taaagtaaag gactttgtag ttgtttttat taaatatgca   1200

tatagtagag tgcaaaaata tagcaaaaat aaaaactaaa ggtagaaaag cattttagat   1260

atgccttaat ttagaaactg tgccaggtgg ccctcggaat agatgccagg cagagaccag   1320

tgcctgggtg gtgcctcctc ttgtctgccc tcatgaagaa gcttccctca cgtgatgtag   1380

tgccctcgta ggtgtcatgt ggagtagtgg gaacaggcag tactgttgag aggagagcag   1440

tgtgagagtt tttctgtaga agcagaactg tcagcttgtg ccttgaggct tccagaacgt   1500

gtcagatgga gaagtccaag tttccatgct tcaggcaact tagctgtgta cagaagcaat   1560

ccagtgtggt aataaaaagc aaggattgcc tgtataattt attataaaat aaaagggatt   1620

ttaacaacca acaattccca acacctcaaa agcttgttgc attttttggt atttgaggtt   1680

tttatctgaa ggttaaaggg caagtgtttg gtatagaaga gcagtatgtg ttaagaaaag   1740

aaaaatattg gttcgcgtag agtgcaaatt agaactagaa agttttatac gattatcatt   1800

ttgagatgtg ttaaagtagg ttttcactgt aaaatgtatt agtgtttctg cattgccata   1860

gggcctggtt aaaactttct cttaggtttc aggaagactg tcacatacag taagcttttt   1920

tccttctgac ttataataga aaatgttttg aaagtaaaaa aaaaaaaaaa aaaggccaca   1980
```

-continued

```
tgtgctcgag ctgcag                                                    1996


<210> SEQ ID NO 2
<211> LENGTH: 2961
<212> TYPE: DNA
<213> ORGANISM: Homo sapiens
<220> FEATURE:
<223> OTHER INFORMATION: hkmt-1098

<400> SEQUENCE: 2

taggcctgta cggaagtgtt acttctgctc taaaagctgc ggaattcctc gagcactgtt      60

ggcctactgg agtctccgga tctccctcgg tccctctctc ctcctcttcc tctctctgga     120

cgcccggctc ctccgcaccc cctccccccgg ggatcccgcg gccttgctcc ctaccctcac    180

ctcaagacga ccatggccac catcccagac tggaagctac agctgctagc ccggcgccgg     240

caggaggagg cgtccgttcg aggccgagag aaagcagaac gggagcgcct gtcccagatg     300

ccagcctgga aacgagggct cctggagcgc cgccgggcca agcttgggct gtcccctggg     360

gagcctagcc ctgtgctagg gactgtagag gctggacctc cagacccgga tgagtctgcg     420

gtccttctgg aggccatcgg gccagtgcac cagaaccgat tcatccggca ggagcggcag     480

cagcagcagc agcaacaaca acggagtgaa gagctgctag cagagagaaa gcctgggcct     540

ctggaggccc gggagcggag acccagccct ggggagatgc gggatcagag ccccaaggga     600

agagagtcaa gagaagagag actaagtccg agggagacca gagagaggag gctggggata     660

gggggagccc aagagttgag cctgaggcct ctggaggctc gggactggag gcaaagccca     720

ggagaggtgg gagacaggag ctcccgactg tcagaggcat ggaaatggag gctgagtcct     780

ggagaaactc cagagcggag tctgagacta gcagagtctc gagagcaaag ccccaggaga     840

aaagaggtgg aaagtagact gagcccaggg gaatctgcct accagaagtt gggcctgaca     900

gaggcccata aatggagacc tgactccaga gagtctcagg aacagagttt ggtacaactg     960

gaggcaacag agtggaggct gaggtcagga gaagaaagac aagactactc ggaagaatgt    1020

gggagaaaag aagagtggcc agttccaggg gtagctccaa aagagactgc agagctgtcc    1080

gagaccctga caagggaggc ccaaggcaac ggttctgcag gagtggaggc agcagagcag    1140

aggcctgtgg aagatggcga gaggggcatg aagccaacag aagggtggaa atggaccctg    1200

aactccggga aggctcgaga atggacaccc agggacatag aggctcaaac tcagaaacca    1260

gaacctccag agtcagcaga gaagcttctg gaatctcccg gtgtggaggc tggagaaggg    1320

gaggctgaga aggaggaggc gggggctcag ggcaggcctc tgagagccct gcagaactgc    1380

tgctctgtgc cctccccccct cccaccagag gacgctggga ctggaggcct gagacagcag   1440

gaagaggaag cagtggagct ccagccccca ccaccagccc ctctgtctcc cccaccccca    1500

gccccaactg ccccccaacc tcctggggat cccctcatga gccgcctgtt ctatggggtg    1560

aaggcagggc caggggtggg ggccccccgc cgcagtggac acaccttcac cgtcaacccc    1620

cggcggtctg tgcccccctgc gaccccagcc accccaacct ctccagccac agttgatgct   1680

gcagtcccgg gggctgggaa gaagcggtac ccaactgccg aggagatctt ggttctgggg    1740

ggctacctcc gtctcagccg cagctgcctt gccaaggggt cccccgaaag acaccacaaa    1800

cagcttaaga tctccttcag cgagacagcc ctggagacca cgtaccaata cccctccgag    1860

agttcggtac tggaggagct gggcccggag cctgaggtcc ccagtgcccc caaccctcca    1920

gcagcccaac ccgacgacga agaggatgag gaagagctgc tgctgctgca gccagagctc    1980
```

-continued

```
cagggcgggc tgcgcaccaa ggccctgatt gtggatgagt cctgccggcg gtgaccatct   2040

tccaacatag ggatatacct ccctccttct tataactgaa gatcctggag cccggaagat   2100

tcagggcaga cagaccctga taatgagcct ggcagggaag ggcaaccaac atcttgtaac   2160

ttgctttccc caccctgttt ctgggggcag agccaattgc ccaatttcta ccctaatcca   2220

aagtccctgg tgtgggtggg gttaaacgtg ctggtgcatc ctaggtcatc caagagtgag   2280

cgccaagtcc tgagaagggg cacagaactc cctggagggt ggagatggag cacctgcccc   2340

ccatggcagg gtacactctc cccacagcct tcctccccac catcccgtgg ggactctcgg   2400

gatttaagca ctcgtctctc tgggaggccc agaccccact ccatttatag gcacatctcc   2460

ttcatttcct aggtcactgc ccctttgttt acagctcctg cctcctccct tgaccacagc   2520

ctggtttaca aattccatca gctcccagcc ccacctgcca aagtcccagg tttacaagcc   2580

acgcttactt gctgtgtctg cgtggaattc tctcctctgt cccctccagt ctcctcattg   2640

gagtgacctg aaggtgtggc ttcctccact tttctcagt attactttgc cttagttttc    2700

cccaagaggg aaggctggaa ctcttaactc tgtacccctt gatagttatt taattctgtt   2760

tctcctagtg gttcacaatt gaactgaatt gagatggtgt cgggtggcta aggagacacc   2820

tcacctctcc ttccccattg tgccgccttt atcaattgcc tgttttgttt tgtttgtttt   2880

ttaactttcc ataataaaat ggagttctct tcaaaaaaaa aaaaaaaaaa aaaaaaaagg   2940

ccacatgtgc tcgagctgca g                                             2961


<210> SEQ ID NO 3
<211> LENGTH: 1973
<212> TYPE: DNA
<213> ORGANISM: Homo sapiens
<220> FEATURE:
<223> OTHER INFORMATION: hkmt-1188

<400> SEQUENCE: 3

ttctaggcct gtacggaagt gttacttctg ctctaaaagc tgcggaattc ctcgagcact     60

gttggcctac tggattccgg gctcgaaggc tgtgcggtct gccaggagct gcggccccgt    120

ccggcccggg ctggcatggg ttggaattgg agcctatccc ccaacccgaa ggctaacagc    180

atcatgtggt tactaactgt tcctcattca ccggttgatg cctcccagaa aaaaacgccg    240

ccagccttcc cagaaagccc cgctgctgtt ccaccaacaa ccactggagg gccccaaaca    300

cagctgtgca tctacacagc ttcccatcac tcacactcga caggtgccca gcaagcccat    360

tgaccacagc accatcactt cctgggtatc acctgatttt gatacagcag caggaagctt    420

gttcccagcc taccagaaac accaaaaccg ggcgagacac tcaagtcgaa aacctaccac    480

ctccaagttt ccacatctaa cttttgagag tccgcaatct tccagttcag agacattggg    540

gatcccctta atccgagagt gccccagtga atcagaaaag gatgtttcca gaagaccctt    600

agttccagtg ctcagtcccc aaagctgtgg gaacatgtca gtgcaggcac ttcagagctt    660

accttatgtg ttcattccac ctgatatcca gaccccagag tcatcgtctg tgaaggaaga    720

actcattccc caagatcaga aggaaaacag ccttctaagc tgcactcttc acactggcac    780

tcctaatagc ccagagcctg gacctgttct ggttaaagac acccccgagg acaagtatgg    840

aataaaggtc acatggagga gacgacagca cctgcttgct tacctcaggg agagagggaa    900

gctgagcaga agccaattcc ttgtgaaaag ctgactgcca tcagtaatct caatagaaaa    960

gagatatgtt ttctggagtc ataaaggaat tcaattccta gggtttttgt ttttgttttt   1020

gagatgtaat attgctctgt tgcccaggct ggagtgcagt ggtatgatct caccttactg   1080
```

```
caaccaccac ttcctgggtt caagcgattc tcctgcctca gcctccccag tagctgggat   1140

tacaggcacc agccaccatg cctggctaat ttttttgtat ttttagtaga gatgtggttt   1200

ctccatgttg gccaggctgg tctcaaaatc ctgacctcaa gtcatctgct ggccttgacc   1260

tcacaaagtg ctggcccagc cgagatttgt tttctaagat actttgtgtc atgaacagtt   1320

cagtttagtg tcatgaacta ttcacttcat atttttcttg tattaactgt ttaaattttt   1380

aaaatatctt gtagtaactc tttaaaatgt atgtaagtaa atggctgcag aaagtttttt   1440

tagagaatcc tgcttccatc agtaatacag caatattacc ccatccacta atggtctttg   1500

tttccttaac cactactcat taatccttaa tcacctcatt caaactaatt cattctgcat   1560

ttttgagtac caactcttgt caggctcagt ggcagcttct acgacctgat ggatggaaaa   1620

aaatcaaact ctgtgactct atggttgact gccacctctg caaccttgac tcatctgctg   1680

aaaaggcaag aagaagaaag ggcagcaagc cctgttttag ggactacata agatgagggg   1740

agataagggg gacatagatg agttctttag gattgcgtgt gttttgagtt tttgtttcta   1800

actgaagaaa tctgtcaata ttaaataggg tgggaaaatg gtttcttaga ataactgttc   1860

aactgtgtgt aaataaggaa agttttcaat gagtattact tattgtaatt aatgcagaag   1920

gacttcccca gtcaaaaaaa aaaaaaaaaa ggccacatgt gctcgagctg cag           1973
```

```
<210> SEQ ID NO 4
<211> LENGTH: 635
<212> TYPE: DNA
<213> ORGANISM: Homo sapiens
<220> FEATURE:
<223> OTHER INFORMATION: hkmt-1345-f

<400> SEQUENCE: 4

cactgttggc ctactgggag acagcgccgc cggccgtggg gagcggacgc agtgatttgc     60

tccccctcgt gcagcaaccc ccacacccag caccaggccc ccagaactct ccttccagct    120

gaactccctg ggaacaagtc agttgggctg atcactgaac tcacatttct ggacctgagg    180

agcctgttcc tctcacgccc tcacctggct gagccgcagt agttcttcag tggcaagctt    240

tatgtcctga cccagctaaa gctgccagtt gaagaactgt tgccctctgc ccctggcttc    300

gaggaggagg aggagctgct ttccccatca tctggaaggt gacagaaatg ggctgggaag    360

gtccgaacag cagggtggat gatacgtttt gggcaagttg gagagccttt gcccagattg    420

gcccagcaag gagcggtttt agattagaga cactggctgg attgaggagt agaaggctca    480

aacaacccaa gcggctacag gaagctgtgt ctgttcgatt tggtgggagg agatgtgcag    540

ggagctgtat cttgtcctcc gcttgtgaaa aactcaagga tgtggagaag agtagaccgt    600

ggaaccctgc tcttctgcag ccaagctgag gggca                               635
```

```
<210> SEQ ID NO 5
<211> LENGTH: 683
<212> TYPE: DNA
<213> ORGANISM: Homo sapiens
<220> FEATURE:
<223> OTHER INFORMATION: hkmt-1345-r

<400> SEQUENCE: 5

ctgcagctcg agcacatgtg gccttttttt tttttttttt tcttaaatta tatttattat     60

atgaaataca aaatgtggaa aatttggaaa ttacagaaaa accaaagatg aaaattacag    120

tgactttgtt ccaccataca aagataacca ctcaacattt tttagtatgc cttccgtctt    180
```

-continued

```
ttttatctgc tctacgtata caagcataca cccatatttt aaaaaaacaa aattgaaatc    240

acataacatg cactattttt acaacctttt aatattcaag gagcattttt ctttcagtca    300

gatgttcttt tacatgactt ttaatgtctg cgcggtactc caccatctgg atggagatac    360

aataatttac ttaagcaatc ccctattgca aactttcgtt acagcagaaa aggaataaat    420

tcccaaccaa accattgctt cccatttttc tccattgcaa tgctgggatg aacatcttat    480

cactaactaa atccttaagt attttcttag gataaattcc caaagataga attcgtaggt    540

caaatgacat ggaggctttt aggccacatg acacatatca cccaactgtc atccaggaag    600

cctgcaccga tgtatactcc cacacgcaat gtatgggaat gtttttttcag tagtctcttt    660

gccaatattg ggtcttattt ttt                                            683


<210> SEQ ID NO 6
<211> LENGTH: 407
<212> TYPE: DNA
<213> ORGANISM: Homo sapiens
<220> FEATURE:
<223> OTHER INFORMATION: hmfn-0044-f

<400> SEQUENCE: 6

ttaaataaaa gctcgtaaca caactaatta aggacttgca agcctggagt gtttgagaga     60

tgtttgtctc aggtgtgtgg gtaggagaag gaagcatcgc gggctggcct ctttgagtgg    120

gcttgcctca tctcagcgca ccaactcctg atttttttca gtgggaaatg tggtggtcat    180

agggtagata ccgatgtctg ccctgctctt tcatctctga aagcctgttt gcagaatgag    240

gccctggctc taccctcatc tcaggctctt ctaaagagct tttgtattct aaagaggatt    300

tttccatcag agaggtagga gctgtaggaa ccccgagggc agataagcag ccctcactct    360

agataaggta tgctgggggga gcttactgag ggaatcctgt acacagc                  407


<210> SEQ ID NO 7
<211> LENGTH: 404
<212> TYPE: DNA
<213> ORGANISM: Homo sapiens
<220> FEATURE:
<223> OTHER INFORMATION: hmfn-0044-r

<400> SEQUENCE: 7

tgtggccttt tttttttttc tttttttgga agcaccagag tccatgaggc attttatttg     60

taaatatatg tattacatcc ctagaaaaag aatcccagga ttttccctcc tgtgtgtttt    120

cgtcttgctt cttcatggtc catgatgcca gctgaggttg tcagtacaat gaaaccaaac    180

tggcgggatg gaagcagatt attctgccat ttttccaggt ctttgagttg cacgtcaaat    240

ctggggctga tcaccccaca cttgtttagc ctgcctgtga ggttcacaac aatttttccca    300

gctctgtggt catcaatgat tccaaattcg ccaatgtaac catgcttcat catcacagtg    360

agaaaccgga cgatgactct ggagcacggc ctaataagca cctg                      404


<210> SEQ ID NO 8
<211> LENGTH: 529
<212> TYPE: DNA
<213> ORGANISM: Homo sapiens
<220> FEATURE:
<223> OTHER INFORMATION: hmfn-0320-f

<400> SEQUENCE: 8

acagtgctgg cctctgcctc catctcagtc acacatgtct agcctccagg cgctgtgctc     60

tggcctgccc ctgcggcccc tcccagagaa ccggggacgc caggctgggg tgccccatgc    120
```

-continued

```
ccctgtcagg acccccagcc tcagccctgt ggagaaacag ctggcgctga ggaacgccct    180

gcgctacttc cccccggatg tccaggagct gctggcccca gagtttgccc aggagctgca    240

actgtacgga cacatctaca tgtaccggtt ttgccccgac attgaaatga gggcctaccc    300

gattgagcag taccccctgcc agacgaaagt ggctgccgcc atcatgcaca tgattatgaa   360

caacctggat cctgccgtgg cccagtttcc ccaggagctg gtgacctatg gaggaaatgg    420

gcaggtgttc agcaactggg ctcagttctg gctgaccatg ttctacttgt cgaagatgac    480

agaggagcag actttggtca tgtacagtgg gcacccactt ggcctcttt               529
```

<210> SEQ ID NO 9
<211> LENGTH: 415
<212> TYPE: DNA
<213> ORGANISM: Homo sapiens
<220> FEATURE:
<223> OTHER INFORMATION: hmfn-0320-r

<400> SEQUENCE: 9

```
tgtggccttt tttttttttt ttttttttct ctgttgaccc tttatttcct ggtctatcct     60

ccttcccgaa ctcctccagg ccagcagccc agggtgccag ggtccagaag ttgcttgcac    120

agacagcaga tgggcagcag acagacagag ttgcatggag gctggcaggt ggccaggaag    180

cagagggtgt gatcatccca gccggagaga gctttaccag tgttcaccgc agggcccccg    240

ggcaggcttg ggacttggcc ctaaatggac tttgacagcc ttcagggctc ccatgcaagt    300

ggcatggttg tggacagaga gctgcatgtc tctgggcctc agggggctgt ctgtaaaatg    360

aggctgtggt ggcaccctgc acagggcacc ataagggcca cgtgaggatg tgcga         415
```

<210> SEQ ID NO 10
<211> LENGTH: 2484
<212> TYPE: DNA
<213> ORGANISM: Homo sapiens
<220> FEATURE:
<223> OTHER INFORMATION: hmfn-0376

<400> SEQUENCE: 10

```
taggcctgta cggaagtgtt acttctgctc taaaagctgc ggaattcctc gagcactgtt     60

ggcctactgg gactgaacca gaaggaagag gacagagcaa agccatgaac atcatcctag    120

aaatccttct gcttctgatc accatcatct actcctactt ggagtcgttg gtgaagtttt    180

tcattcctca gaggagaaaa tctgtggctg gggagattgt tctcattact ggagctgggc    240

atggaatagg caggcagact acttatgaat ttgcaaaacg acagagcata ttggttctgt    300

gggatattaa taagcgcggt gtggaggaaa ctgcagctga gtgccgaaaa ctaggcgtca    360

ctgcgcatgc gtatgtggta gactgcagca acagagaaga gatctatcgc tctctaaatc    420

aggtgaagaa agaagtgggt gatgtaacaa tcgtggtgaa taatgctggg acagtatatc    480

cagccgatct tctcagcacc aaggatgaag agattaccaa gacatttgag gtcaacatcc    540

taggacattt ttggatcaca aaagcacttc ttccatcgat gatggagaga aatcatggcc    600

acatcgtcac agtggcttca gtgtgcggcc acgaagggat tccttacctc atcccatatt    660

gttccagcaa atttgccgct gttggctttc acagaggtct gacatcagaa cttcaggcct    720

tgggaaaaac tggtatcaaa acctcatgtc tctgcccagt ttttgtgaat actgggttca    780

ccaaaaatcc aagcacaaga ttatggcctg tattggagac agatgaagtc gtaagaagtc    840

tgatagatgg aatacttacc aataagaaaa tgatttttgt tccatcgtat atcaatatct    900
```

-continued

```
ttctgagact acagaagttt cttcctgaac gcgcctcagc gattttaaat cgtatgcaga    960
atattcaatt tgaagcagtg gttggccaca aaatcaaaat gaaatgaata aataagctcc   1020
agccagagat gtatgcatga taatgatatg aatagtttcg aatcaatgct gcaaagcttt   1080
atttcacatt ttttcagtcc tgataatatt aaaaacattg gtttggcact agcagcagtc   1140
aaacgaacaa gattaattac ctgtcttcct gtttctcaag aatatttacg tagtttttca   1200
taggtctgtt tttcctttca tgcctcttaa aaacttctgt gcttacataa acatacttaa   1260
aaggttttct ttaagatatt ttatttttcc atttaaaggt ggacaaaagc tacctcccta   1320
aaagtaaata caaagagaac ttatttacac agggaaggtt taagactgtt caagtagcat   1380
tccaatctgt agccatgcca cagaatatca acaagaacac agaatgagtg cacagctaag   1440
agatcaagtt tcagcaggca gctttatctc aacctggaca tattttaaga ttcagcattt   1500
gaaagatttc cctagcctct tcctttttca ttagcccaaa acggtgcaac tctattctgg   1560
actttattac ttgattctgt cttctgtata actctgaagt ccaccaaaag tggaccctct   1620
atatttcctc ccttttata gtcttataag atacattatg aaaggtgacc gactctattt   1680
taaatctcag aattttaagt tctagcccca tgataacctt tttctttgta atttatgctt   1740
tcatatatcc ttggtcccag agatgtttag acaattttag gctcaaaaat taaagctaac   1800
acaggaaaag gaactgtact ggctattaca taagaaacaa tggacccaag agaagaaaag   1860
gaagaaagaa aggtttttttg gtttttgttt tgttttgttt tgttttttgt ttttttgaga   1920
tggagtctca ctctttcgcc caggctggag tgcagtcgta tgatctcagc tcactgcaag   1980
ctccacctcc cgggttcacg ccattctcct gcctcagcct cctgagtagc tgggactaca   2040
ggcgcccgcc accacacccg gctaattttt tgtatttttt gtagagacgg ggtttcacca   2100
tgttagccaa gatggtctcg atctcctgac ctcgtgatcc acctgcctcg gcctcccaaa   2160
gtgctgggat tacgggtgtg agccaccgtg cccagccttt tttttttta atagaaaaaa   2220
taatccgact cccactacat caagactaat cttgttttgt gtgtttttca catgtattat   2280
agaatgcttt tgcatggact atcctcttgt ttttattaaa aacaaatgat ttttttaaaa   2340
gtcacaaaaa caattcacta aaaataaata tgtcattgtg ctttaaaaaa ataacctctt   2400
gtagttataa aataaaacgt ttgacttcta aaaaaaaaaa aaaaaaaaaa aaaaaaaaaa   2460
aggccacatg tgctcgagct gcag                                          2484
```

<210> SEQ ID NO 11
<211> LENGTH: 1870
<212> TYPE: DNA
<213> ORGANISM: Homo sapiens
<220> FEATURE:
<223> OTHER INFORMATION: hmfn-0601

<400> SEQUENCE: 11

```
ttctaggcct gtacggaagt gttacttctg ctctaaaagc tgcggaattc ctcgagcact     60
gttggcctac tgggtcccgg aggtgcggtg tggggcaccg ggcggggccg cgggaaccgg    120
cgccccacgg agctgctgct gtcagaccaa ccccgggccc ccatcatcac tgcgccgcgc    180
tttcaggcgc cgagaactac cgttcccggc atgccatgaa attggcctcg gcgctgaggc    240
ggggtccggc cctccacccg ctcccgccgc gcgcgaatcg cggtcgcgag ccatggagga    300
ggaggcatcg tccccggggc tgggctgcag caagccgcac ctggagaagc tgaccctggg    360
catcacgcgc atcctagaat cttccccagg tgtgactgag gtgaccatca tagaaaagcc    420
tcctgctgaa cgtcatatga tttcttcctg ggaacaaaag aataactgtg tgatgcctga    480
```

-continued

```
agatgtgaag aacttttacc tgatgaccaa tggcttccac atgacatgga gtgtgaagct    540

ggatgccagt gatgatcagc cagagaagcc tcactttgac tctcgcagtg tgatatttga    600

gctggattca tgcaatggca gtgggaaagt ttgccttgtc tacaaaagtg ggaaaccagc    660

attagcagaa gacactgaga tctggttcct ggacagagcg ttatactggc attttctcac    720

agacaccttt actgcctatt accgcctgct catcacccac ctgggcctgc cccagtggca    780

atatgccttc accagctatg gcattagccc acaggccaag caatggttca gcatgtataa    840

acctatcacc tacaacacaa acctgctcac agaagagacc gactcctttg tgaataagct    900

agatcccagc aaagtgttta agagcaagaa caagatcgta atcccaaaaa agaaagggcc    960

tgtgcagcct gcaggtggcc agaaagggcc ctcaggaccc tccggtccct ccacttcctc   1020

cacttctaaa tcctcctctg gctctggaaa ccccacccgg aagtgagcac ccctccctcc   1080

aactccctac cagctccaga gtggtggttt ccatgcacag atggccctag ggtgacctc    1140

cagttttgcg tgtggaccgt aggcctcttt ctagttgaat gaccaaaatt gtaaggcttt   1200

tagtcccacc gacattagcc aggctcgtag tgaggcctcc agagcaggtt gtgctgtccc   1260

ctgcctctgg aagcaatggg gaatttggaa tcttgtgtaa gtgcccaaat aagtctgagt   1320

gctttcctct tcttcaacac tcaaccctca atcccttagc actgattgat tagagaggtc   1380

ccccaaagaa accactggtt ttgacccatg aagcattaga actgcattgt tcattcagga   1440

gccactagtc acatatgact atttaaattt aaagtaaatt gtatgaaaaa ttcatttctt   1500

caattgcatt agccacattt tgagtattca tgtggctggt agattctgta ttagcacaaa   1560

gatatggaac atttccatca ccacagaaag ttctgttgga cagcactgca ttagaatatt   1620

ttcatactgc tcttcctcaa ttaatttttg ttgttaatgt tgatgtcttc attggatggg   1680

tcataatgtt ccatgaaacc tctcaagtac acaattgtat gttctttgta tcccttacca   1740

caaatatctc gctctgctca tttcttttgc agcttcctat aaagtttgtc ttcctcatca   1800

aaaaaaaaaa aaaaaaaaaa aaaaaaaaaa aaaaaaaaaa aaaaaaaggc cacatgtgct   1860

cgagctgcag                                                          1870
```

```
<210> SEQ ID NO 12
<211> LENGTH: 2252
<212> TYPE: DNA
<213> ORGANISM: Homo sapiens
<220> FEATURE:
<223> OTHER INFORMATION: hmfn-0656

<400> SEQUENCE: 12

taggcctgta cggaagtgtt acttctgctc taaaagctgc ggaattcctc gagcactgtt     60

ggcctactgg gtgcgttcct cgtctgccag ccggcttggc tagcgcgcgg cggccgtggc    120

taaggctgct acgaagcgag cttgggagga gcagcggcct gcggggcaga ggagcatccc    180

gtctaccagg tcccaagcgg cgtggcccgc gggtcatggc caaaggagaa ggcgccgaga    240

gcggctccgc ggcggggctg ctacccacca gcatcctcca aagcactgaa cgcccggccc    300

aggtgaagaa agaaccgaaa aagaagaaac aacagttgtc tgtttgcaac aagctttgct    360

atgcacttgg gggagccccc taccaggtga cgggctgtgc cctgggtttc ttccttcaga    420

tctacctatt ggatgtggct caggtgggcc ctttctctgc ctccatcatc ctgtttgtgg    480

gccgagcctg ggatgccatc acagaccccc tggtgggcct ctgcatcagc aaatccccct    540

ggacctgcct gggtcgcctt atgccctgga tcatcttctc cacgcccctg gccgtcattg    600
```

-continued

```
cctacttcct catctggttc gtgcccgact tcccacacgg ccagacctat tggtacctgc    660

ttttctattg cctctttgaa acaatggtca cgtgtttcca tgttccctac tcggctctca    720

ccatgttcat cagcaccgag cagactgagc gggattctgc caccgcctat cggatgactg    780

tggaagtgct gggcacagtg ctgggcacgg cgatccaggg acaaatcgtg ggccaagcag    840

acacgccttg tttccaggac ctcaatagct ctacagtagc ttcacaaagt gccaaccata    900

cacatggcac cacctcacac agggaaacgc aaaaggcata cctgctggca gcgggggtca    960

ttgtctgtat ctatataatc tgtgctgtca tcctgatcct gggcgtgcgg gagcagagag   1020

aaccctatga agcccagcag tctgagccaa tcgcctactt ccggggccta cggctggtca   1080

tgagccacgg cccatacatc aaacttatta ctggcttcct cttcacctcc ttggctttca   1140

tgctggtgga ggggaacttt gtcttgtttt gcacctacac cttgggcttc cgcaatgaat   1200

tccagaatct actcctggcc atcatgctct cggccacttt aaccattccc atctggcagt   1260

ggttcttgac ccggtttggc aagaagacag ctgtatatgt tgggatctca tcagcagtgc   1320

catttctcat cttggtggcc ctcatggaga gtaacctcat cattacatat gcggtagctg   1380

tggcagctgg catcagtgtg gcagctgcct tcttactacc ctggtccatg ctgcctgatg   1440

tcattgacga cttccatctg aagcagcccc acttccatgg aaccgagccc atcttcttct   1500

ccttctatgt cttcttcacc aagtttgcct ctggagtgtc actgggcatt tctaccctca   1560

gtctggactt tgcagggtac cagacccgtg gctgctcgca gccggaacgt gtcaagttta   1620

cactgaacat gctcgtgacc atggctccca tagttctcat cctgctgggc ctgctgctct   1680

tcaaaatgta ccccattgat gaggagaggc ggcggcagaa taagaaggcc ctgcaggcac   1740

tgagggacga ggccagcagc tctggctgct cagaaacaga ctccacagag ctggctagca   1800

tcctctaggg cccgccacgt tgcccgaagc caccatgcag aaggccacag aagggatcag   1860

gacctgtctg ccggcttgct gagcagctgg actgcaggtg ctaggaaggg aactgaagac   1920

tcaaggaggt ggcccaggac acttgctgtg ctcactgtgg ggccggctgc tctgtggcct   1980

cctgcctccc ctctgcctgc ctgtggggcc aagccctggg gctgccactg tgaatatgcc   2040

aaggactgat cgggcctagc ccggaacact aatgtagaaa cctttttttt acagagccta   2100

attaataact taatgactgt gtacatagca atgtgtgtgt atgtatatgt ctgtgagcta   2160

ttaatgttat taattttcat aaaagctgga aagcagaaaa aaaaaaaaaa aaaaaaaaaa   2220

aaaaaaaaaa ggccacatgt gctcgagctg ca                                 2252
```

<210> SEQ ID NO 13
<211> LENGTH: 487
<212> TYPE: DNA
<213> ORGANISM: Homo sapiens
<220> FEATURE:
<223> OTHER INFORMATION: hmfn-0672-f

<400> SEQUENCE: 13

```
aaatacctga accaaggaga agctgccacc atctcctctg tggattcctg taaccaaacc     60

agaacttttt tttttttttt tctgttcagt gacatctggc tggttctcct gaactgagaa    120

gagcaggagt tcacgtaaca aggaatggca gaaacgaagg atgtttttgg ccaggaaccg    180

catccagttg aagatgattt atataaagaa ccaacgagaa aaagaaggaa atcagatcga    240

gaccagcggt tccgagcatt tccctccatg gagcagagtg ctcttaagga atatgaaaaa    300

ttggaatcac ggaccagaag ggttttgagc aacacttatc agaaacttat tcagtctgtc    360

ttcctggatg acagcatccc taatggagtc aagtatctca taaataggct tcttgccttg    420
```

```
attgaaaagc cgacagtgga cccaatctac attgcattat ttggaagcac tggggctggg    480

aagagct                                                              487


<210> SEQ ID NO 14
<211> LENGTH: 432
<212> TYPE: DNA
<213> ORGANISM: Homo sapiens
<220> FEATURE:
<223> OTHER INFORMATION: hmfn-0672-r

<400> SEQUENCE: 14

tgtggccttt tttttttttt tttttgagac atagtctcac tccgtcgtcc aggctggagt     60

gcagtgatgt cccggggggg ccagccttgc tgggggatgc ccttaggagg aattcttgca    120

tgcccttcct cagccgtgca ttctccgcga cctccctcag gcttctgtgc agcttctcca    180

tctccttgta ttcactcccg acatctgcaa gctccttgta gaggccatcc ccctgggacg    240

aagcaagggc cagcatagtg gtgatgctgc ccttcacctt ctccacgatt ccagtcttca    300

gctgctgaaa ctggtgctgc atcctttcct gggccctttc aaacatgccc tcagccacct    360

gccggtccac tcctcttctg atggcatctt tcatccgctc acacgctttt ttgcccgtga    420

tctgagctgc ct                                                        432


<210> SEQ ID NO 15
<211> LENGTH: 507
<212> TYPE: DNA
<213> ORGANISM: Homo sapiens
<220> FEATURE:
<223> OTHER INFORMATION: hmfn-0883-f

<400> SEQUENCE: 15

gattagctga gctctctttc cgacagtgca gggattctga agctgtctgc ttgagttact     60

gtgctctctt ccaaggctgt aggagttctg gagctgctgg ctggagagga gggtggacga    120

agctctctcc agaaagacat cctgagagga cttggcaggc ctgaacatgc attggctgcg    180

aaaagttcag ggactttgca ccctgtgggg tactcagatg tccagccgca ctctctacat    240

taatagtagg caactggtgt ccctgcagtg gggccaccag gaagttccgg ccaagtttaa    300

ctttgctagt gatgtgttgg atcactgggc tgacatggag aaggctggca agcgactccc    360

aagcccagcc ctgtggtggg tgaatgggaa ggggaaggaa ttaatgtgga atttcagaga    420

actgagtgaa aacagccagc aggcagccaa cgtcctctcg ggagcctgtg gcctgcagcg    480

tggggatcgt gtggcagtga tgctgcc                                        507


<210> SEQ ID NO 16
<211> LENGTH: 566
<212> TYPE: DNA
<213> ORGANISM: Homo sapiens
<220> FEATURE:
<223> OTHER INFORMATION: hmfn-0883-r

<400> SEQUENCE: 16

tgtggccttt tttttttttt ttttggtttt aaaattattt taatatttga ttctaggaag     60

agtagataac accaaaaaca tgaggtatgg gtagctgata actttggcag tgcttacttt    120

gttctcacag ctatgatcta aggtctgtag atgccacaca caggtgaaac aatgtggtat    180

ttataatgtg tctgggtcag tgcctggcac atggcaaatg cttaataaat ggtggttccc    240

ctctgaccct gacagtttca aggtttggag tgacttgcgg atgattctaa tgtcccagcc    300
```

-continued

```
ccacacacaa gtcttcctgt atggaggtct tctcctaggg taaaagaaag taccacttct    360

tttcctttca tttccttctc aagctccagt tttatgcttg actttgtcta tctgtgggaa    420

tatttatagg ttttcctctt tacttccctc tcttcctttc ttcctgtctt ccatgacttt    480

tctttatcag tttcttttac tatttttatt tttacaattt ttttctctcc ctttctccct    540

ctctttctcc ctctctttct ttcttg                                         566
```

<210> SEQ ID NO 17
<211> LENGTH: 2124
<212> TYPE: DNA
<213> ORGANISM: Homo sapiens
<220> FEATURE:
<223> OTHER INFORMATION: hmfn-1045

<400> SEQUENCE: 17

```
taggcctgta cggaagtgtt acttctgctc taaaagctgc ggaattcctc gagcactgtt     60

ggcctactgg aaaagcagct acaggtcatc tcagtgctcc agtgggtcct gtccttcctt    120

gtactgggag tggcctgcag tgccatcctc atgtacatat tctgcactga ttgctggctc    180

atcgctgtgc tctacttcac ttggctggtg tttgactgga acacacccaa gaaaggtggc    240

aggaggtcac agtgggtccg aaactgggct gtgtggcgct actttcgaga ctactttccc    300

atccagctgg tgaagacaca caacctgctg accaccagga actatatctt tggataccac    360

ccccatggta tcatgggcct gggtgccttc tgcaacttca gcacagaggc cacagaagtg    420

agcaagaagt tcccaggcat acggccttac ctggctacac tggcaggcaa cttccgaatg    480

cctgtgttga gggagtacct gatgtctgga ggtatctgcc ctgtcagccg ggacaccata    540

gactatttgc tttcaaagaa tgggagtggc aatgctatca tcatcgtggt cgggggtgcg    600

gctgagtctc tgagctccat gcctggcaag aatgcagtca ccctgcggaa ccgcaagggc    660

tttgtgaaac tggccctgcg tcatggagct gacctggttc ccatctactc ctttggagag    720

aatgaagtgt acaagcaggt gatcttcgag gagggctcct ggggccgatg ggtccagaag    780

aagttccaga aatacattgg tttcgcccca tgcatcttcc atggtcgagg cctcttctcc    840

tccgacacct gggggctggt gccctactcc aagcccatca ccactgttgt gggagagccc    900

atcaccatcc ccaagctgga gcacccaacc cagcaagaca tcgacctgta ccacaccatg    960

tacatggagg ccctggtgaa gctcttcgac aagcacaaga ccaagttcgg cctcccggag   1020

actgaggtcc tggaggtgaa ctgagccagc cttcggggcc aattccctgg aggaaccagc   1080

tgcaaatcac tttttttgctc tgtaaatttg gaagtgtcat gggtgtctgt gggttattta   1140

aaagaaatta taacaatttt gctaaaccat tacaatgtta ggtctttttt aagaaggaaa   1200

aagtcagtat ttcaagttct ttcacttcca gcttgccctg ttctaggtgg tggctaaatc   1260

tgggcctaat ctgggtggct cagctaacct ctcttcttcc cttcctgaag tgacaaagga   1320

aactcagtct tcttggggaa gaaggattgc cattagtgac ttggaccagt tagatgattc   1380

actttttgcc cctagggatg agaggcgaaa gccacttctc atacaagccc ctttattgcc   1440

actaccccac gctcgtctag tcctgaaact gcaggaccag tttctctgcc aaggggagga   1500

gttggagagc acagttgccc cgttgtgtga gggcagtagt aggcatctgg aatgctccag   1560

tttgatctcc cttctgccac ccctacctca cccctagtca ctcatatcgg agcctggact   1620

ggcctccagg atgaggatgg gggtggcaat gacaccctgc aggggaaagg actgcccccc   1680

atgcaccatt gcagggagga tgccgccacc atgagctagg tggagtaact ggtttttctt   1740

gggtggctga tgacatggat gcagcacaga ctcagccttg gcctggagca catgcttact   1800
```

```
ggtggcctca gtttaccttc cccagatcct agattctgga tgtgaggaag agatccctct   1860

tcagaagggg cctggccttc tgagcagcag attagttcca aagcaggtgg cccccgaacc   1920

caagcctcac ttttctgtgc cttcctgagg gggttgggcc ggggaggaaa cccaaccctc   1980

tcctgtgtgt tctgttatct cttgatgaga tcattgcacc atgtcagact tttgtatatg   2040

ccttgaaaat aaatgaaagt gagaatcctc aaaaaaaaaa aaaaaaaaaa aaaaaaaaaa   2100

aggccacatg tgctcgagct gcag                                          2124


<210> SEQ ID NO 18
<211> LENGTH: 404
<212> TYPE: DNA
<213> ORGANISM: Homo sapiens
<220> FEATURE:
<223> OTHER INFORMATION: hmfn-1187-f

<400> SEQUENCE: 18

atgtaccagc tgcgtcctct gggccacgct ccacttgccc gcttccaccc ggaaagcccc     60

ccaggctgag tgcggcatga tctccatcac cgaatggcag aagattggtg tggggatcac    120

cggtttcggc atcttcttca tcctctttgg aacactcctg tactttgatt ccgtgctcct    180

ggcctttgga aacctgctgt tcctgacggg cctgtccctc atcattggcc tgaggaagac    240

cttttggttc ttcttccaac ggcacaaact caagggaacc agcttcctcc tgggggggtgt    300

ggttatcgtg ctcctacgct ggcccctcct cggcatgttc ctggaaacct acggattctt    360

cagcctcttt aagggctttt tccctgtcgc cttcggcttc ctgg                    404


<210> SEQ ID NO 19
<211> LENGTH: 414
<212> TYPE: DNA
<213> ORGANISM: Homo sapiens
<220> FEATURE:
<223> OTHER INFORMATION: hmfn-1187-r

<400> SEQUENCE: 19

tgtggccttt tttttttttt tttttttttt tttttcacac gcacaacttg ggaatttaat     60

cttcactttt cctcccataa atatagagtg agggtgtgat accagcccca gcccagtctc    120

cttggggtct gcatctctgc ttcctggcag cctcttgagt cgacttgggg atttgacgtc    180

agttgctcag ctccattcct tccttctgga cttggggagg tccggatatg tcggggagtg    240

agtcagtgca ggggactgag gggtggttcc ccattctccc tctagccccc tcaaccaatg    300

atccaagttc aaggagctca tctctgtttt tcaaaccatc gagctagtgc cttgaagtct    360

ccggaacagc tgtgggagcc aagaatcatt actccacaca aagggtagag agca          414


<210> SEQ ID NO 20
<211> LENGTH: 498
<212> TYPE: DNA
<213> ORGANISM: Homo sapiens
<220> FEATURE:
<223> OTHER INFORMATION: hmfn-1249-f

<400> SEQUENCE: 20

agtctctccc agcgaccgcc gcgggggcaa ggcctggagc tgtggttcga atttgtgcag     60

gcagcgggtg ctggctttta gggtccgccg cctctctgcc taatgagctg caccagaatg    120

atccaggttt tagatccacg tcctttgaca agttcggtca tgcccgtgga tgtggccatg    180

aggctttgct tggcacattc accacctgtg aagagtttcc tgggcccgta cgatgaattt    240
```

-continued

```
caacgacgac attttgtgaa taaattaaag cccctgaaat catgtctcaa tataaaacac    300

aaagccaaat cacagaatga ctggaagtgc tcacacaacc aagccaagaa gcgcgttgtg    360

tttgctgact ccaagggcct ctctctcact gcgatccatg tcttctccga cctcccagaa    420

gaaccagcgt gggatctgca gtttgatctc ttggacctta atgatatctc ctctgcctta    480

aaacaccacg aggagaaa                                                  498
```

```
<210> SEQ ID NO 21
<211> LENGTH: 1772
<212> TYPE: DNA
<213> ORGANISM: Homo sapiens
<220> FEATURE:
<223> OTHER INFORMATION: hmfn-1655

<400> SEQUENCE: 21

taggcctgta cggaagtgtt acttctgctc taaaagctgc ggaattcctc gagcactgtt     60

ggcctactgg gttgaggcca ccctggtggc accaaagccc tctcaggcag gcagacccag    120

ggcctccccg ccacaccttg ttcatggatt ttgtcgctgg agccatcgga ggcgtctgcg    180

gtgttgctgt gggctacccc ctggacacgg tgaagggcct gctggccttg ccctaggcct    240

ggagccgctc gtgcctgaag cccacttctc ctgcaggtca ggatccagac ggagccaaag    300

tacacaggca tctggcactg cgtccgggat acgtatcacc gagagcgcgt gtggggcttc    360

taccggggcc tctcgctgcc cgtgtgcacg gtgtccctgg tatcttccgt gtcttttggc    420

acctaccgcc actgcctggc gcacatctgc cggctccggt acggcaaccc tgacgccaag    480

cccaccaagg ccgacatcac gctctcggga tgcgcctccg gcctcgtccg cgtgtcctgt    540

gcccccagcc tgcccagagc ccaagtaccg cgggccactg cactgcctgg ccacggtagc    600

ccgtgaggag gggctgtgcg gcctctacaa gggcagctcg gccctggtct tacgggacgg    660

ccactccttt gccacctact tcctttccta cgccgctggc cacagccggc cagatgtccc    720

gggcgtgctg gtggccgggg gctgtgcagg agtcctggcc tgggctgtgg ccaccccccat   780

ggacgtgatc aagtcgagac tgcaggcaga cgggcagggc cagaggcgct accggggtct    840

cctgcactgt atggtgacca gcgttcgaga ggagggaccc cgggtccttt tcaaggggct    900

ggtactcaat tgctgccgcg ccttccctgt caacatggtg gtcttcgtcg cctatgaggc    960

agtgctgagg ctcgcccggg gtctgctcac atagccggtc cccacgccca gcggcccacc   1020

caccagcagc tgctggaggt tgtagtggct ggaggaggca aggggtagtg tggctgggtt   1080

cgggacccca cagggccatt gcccaggaga atgaggagcc tccctgcagt gttgtcggcc   1140

gaggcctgag ctcgccctgc ccagctactg acctcaggtc gaggggcccg ccagccatca   1200

gccagggttg gcctagggtg gcaggagcca gggaggagtg ggcctctttg atgagagcgt   1260

tgagttgcat ggagtcggtt gttcatccca gcctccccat ggccctcgcc tcccatgtct   1320

ttgaagcacc cctccaggga gtcaggtgtg tgctcagcca ccctctgccc cattcctaga   1380

ccctcacccc caccactgtt cctgtgtctt cacgagctgt ccccttacagg cagggggcttc  1440

ccacaggctg gggcctcgg ggcggggagc atgagctggg ctggcaccac gactgagggc   1500

tcccggcccg gcttcttccc cacagcaggc tgctcagagg gggtgctgcc gggactgcca   1560

tgcccacctg agaggggcct ggggtggccg tcctcggccg gttagggaat ttggggtgag   1620

gttcctcagg agccctcact ctgcctgtgg acgctgcacc tgccacttaa agaccccaaa   1680

gactctgttg ggaactgttg tcaataaaat gtttctgagg aaaaaaaaaa aaaaaaaaaa   1740

aaaaaaaaag gccacatgtg ctcgagctgc ag                                 1772
```

<210> SEQ ID NO 22
<211> LENGTH: 426
<212> TYPE: DNA
<213> ORGANISM: Homo sapiens
<220> FEATURE:
<223> OTHER INFORMATION: hmfn-1661-f

<400> SEQUENCE: 22

```
ctaagcctcg attgaaggag cacatccctt ccattgaagc tgcagaggag cagctgccac     60

cctgtgcacc cacacttgct taagggtcta gctggataac aaaaggaggc ccagaatcgg    120

tggagcttgg agatgagcga agcagtcctg caccaggttc tgaactaatt agctggtgga    180

ggggacagta cgagtttaaa cagcggctct gggtgcctaa gattctacat tttatacaga    240

catccttggt tccagagggg gctgagcagg ggggtccgag gtgagtctgt gagcatgtgc    300

aagtctatac cagcttgtga aggacatgcc atgtcccctg agtactcata gaaagacacc    360

aacatgacaa aggtagtttg gctttatacc tagaaaaggc ccccaggtca caagcttctc    420

aggact                                                               426
```

<210> SEQ ID NO 23
<211> LENGTH: 588
<212> TYPE: DNA
<213> ORGANISM: Homo sapiens
<220> FEATURE:
<223> OTHER INFORMATION: hmfn-1661-r
<220> FEATURE:
<221> NAME/KEY: modified_base
<222> LOCATION: (58)..(58)
<223> OTHER INFORMATION: a, t, c, g, unknown or other
<220> FEATURE:
<221> NAME/KEY: modified_base
<222> LOCATION: (66)..(66)
<223> OTHER INFORMATION: a, t, c, g, unknown or other
<220> FEATURE:
<221> NAME/KEY: modified_base
<222> LOCATION: (83)..(83)
<223> OTHER INFORMATION: a, t, c, g, unknown or other
<220> FEATURE:
<221> NAME/KEY: modified_base
<222> LOCATION: (86)..(86)
<223> OTHER INFORMATION: a, t, c, g, unknown or other
<220> FEATURE:
<221> NAME/KEY: modified_base
<222> LOCATION: (92)..(92)
<223> OTHER INFORMATION: a, t, c, g, unknown or other
<220> FEATURE:
<221> NAME/KEY: modified_base
<222> LOCATION: (99)..(99)
<223> OTHER INFORMATION: a, t, c, g, unknown or other
<220> FEATURE:
<221> NAME/KEY: modified_base
<222> LOCATION: (105)..(105)
<223> OTHER INFORMATION: a, t, c, g, unknown or other
<220> FEATURE:
<221> NAME/KEY: modified_base
<222> LOCATION: (108)..(108)
<223> OTHER INFORMATION: a, t, c, g, unknown or other
<220> FEATURE:
<221> NAME/KEY: modified_base
<222> LOCATION: (117)..(117)
<223> OTHER INFORMATION: a, t, c, g, unknown or other
<220> FEATURE:
<221> NAME/KEY: modified_base
<222> LOCATION: (127)..(127)
<223> OTHER INFORMATION: a, t, c, g, unknown or other
<220> FEATURE:
<221> NAME/KEY: modified_base
<222> LOCATION: (133)..(133)
<223> OTHER INFORMATION: a, t, c, g, unknown or other
<220> FEATURE:

-continued

<221> NAME/KEY: modified_base
<222> LOCATION: (135)..(135)
<223> OTHER INFORMATION: a, t, c, g, unknown or other
<220> FEATURE:
<221> NAME/KEY: modified_base
<222> LOCATION: (145)..(145)
<223> OTHER INFORMATION: a, t, c, g, unknown or other
<220> FEATURE:
<221> NAME/KEY: modified_base
<222> LOCATION: (158)..(158)
<223> OTHER INFORMATION: a, t, c, g, unknown or other
<220> FEATURE:
<221> NAME/KEY: modified_base
<222> LOCATION: (164)..(164)
<223> OTHER INFORMATION: a, t, c, g, unknown or other
<220> FEATURE:
<221> NAME/KEY: modified_base
<222> LOCATION: (177)..(177)
<223> OTHER INFORMATION: a, t, c, g, unknown or other
<220> FEATURE:
<221> NAME/KEY: modified_base
<222> LOCATION: (180)..(180)
<223> OTHER INFORMATION: a, t, c, g, unknown or other
<220> FEATURE:
<221> NAME/KEY: modified_base
<222> LOCATION: (187)..(187)
<223> OTHER INFORMATION: a, t, c, g, unknown or other
<220> FEATURE:
<221> NAME/KEY: modified_base
<222> LOCATION: (197)..(197)
<223> OTHER INFORMATION: a, t, c, g, unknown or other
<220> FEATURE:
<221> NAME/KEY: modified_base
<222> LOCATION: (204)..(204)
<223> OTHER INFORMATION: a, t, c, g, unknown or other
<220> FEATURE:
<221> NAME/KEY: modified_base
<222> LOCATION: (207)..(207)
<223> OTHER INFORMATION: a, t, c, g, unknown or other
<220> FEATURE:
<221> NAME/KEY: modified_base
<222> LOCATION: (221)..(221)
<223> OTHER INFORMATION: a, t, c, g, unknown or other
<220> FEATURE:
<221> NAME/KEY: modified_base
<222> LOCATION: (225)..(225)
<223> OTHER INFORMATION: a, t, c, g, unknown or other
<220> FEATURE:
<221> NAME/KEY: modified_base
<222> LOCATION: (234)..(234)
<223> OTHER INFORMATION: a, t, c, g, unknown or other
<220> FEATURE:
<221> NAME/KEY: modified_base
<222> LOCATION: (239)..(240)
<223> OTHER INFORMATION: a, t, c, g, unknown or other
<220> FEATURE:
<221> NAME/KEY: modified_base
<222> LOCATION: (246)..(246)
<223> OTHER INFORMATION: a, t, c, g, unknown or other
<220> FEATURE:
<221> NAME/KEY: modified_base
<222> LOCATION: (255)..(255)
<223> OTHER INFORMATION: a, t, c, g, unknown or other
<220> FEATURE:
<221> NAME/KEY: modified_base
<222> LOCATION: (260)..(260)
<223> OTHER INFORMATION: a, t, c, g, unknown or other
<220> FEATURE:
<221> NAME/KEY: modified_base
<222> LOCATION: (263)..(263)
<223> OTHER INFORMATION: a, t, c, g, unknown or other
<220> FEATURE:
<221> NAME/KEY: modified_base
<222> LOCATION: (266)..(266)
<223> OTHER INFORMATION: a, t, c, g, unknown or other
<220> FEATURE:
<221> NAME/KEY: modified_base
<222> LOCATION: (269)..(269)
<223> OTHER INFORMATION: a, t, c, g, unknown or other
<220> FEATURE:
<221> NAME/KEY: modified_base
<222> LOCATION: (273)..(273)
<223> OTHER INFORMATION: a, t, c, g, unknown or other
<220> FEATURE:
<221> NAME/KEY: modified_base
<222> LOCATION: (278)..(278)
<223> OTHER INFORMATION: a, t, c, g, unknown or other
<220> FEATURE:
<221> NAME/KEY: modified_base
<222> LOCATION: (281)..(282)
<223> OTHER INFORMATION: a, t, c, g, unknown or other
<220> FEATURE:
<221> NAME/KEY: modified_base
<222> LOCATION: (299)..(299)
<223> OTHER INFORMATION: a, t, c, g, unknown or other
<220> FEATURE:
<221> NAME/KEY: modified_base
<222> LOCATION: (301)..(301)
<223> OTHER INFORMATION: a, t, c, g, unknown or other
<220> FEATURE:
<221> NAME/KEY: modified_base
<222> LOCATION: (304)..(304)
<223> OTHER INFORMATION: a, t, c, g, unknown or other
<220> FEATURE:
<221> NAME/KEY: modified_base
<222> LOCATION: (308)..(308)
<223> OTHER INFORMATION: a, t, c, g, unknown or other
<220> FEATURE:
<221> NAME/KEY: modified_base
<222> LOCATION: (312)..(312)
<223> OTHER INFORMATION: a, t, c, g, unknown or other
<220> FEATURE:
<221> NAME/KEY: modified_base
<222> LOCATION: (333)..(333)
<223> OTHER INFORMATION: a, t, c, g, unknown or other
<220> FEATURE:
<221> NAME/KEY: modified_base
<222> LOCATION: (357)..(357)
<223> OTHER INFORMATION: a, t, c, g, unknown or other
<220> FEATURE:
<221> NAME/KEY: modified_base
<222> LOCATION: (364)..(364)
<223> OTHER INFORMATION: a, t, c, g, unknown or other
<220> FEATURE:
<221> NAME/KEY: modified_base
<222> LOCATION: (377)..(377)
<223> OTHER INFORMATION: a, t, c, g, unknown or other
<220> FEATURE:
<221> NAME/KEY: modified_base
<222> LOCATION: (381)..(381)
<223> OTHER INFORMATION: a, t, c, g, unknown or other
<220> FEATURE:
<221> NAME/KEY: modified_base
<222> LOCATION: (392)..(392)
<223> OTHER INFORMATION: a, t, c, g, unknown or other
<220> FEATURE:
<221> NAME/KEY: modified_base
<222> LOCATION: (421)..(421)
<223> OTHER INFORMATION: a, t, c, g, unknown or other
<220> FEATURE:
<221> NAME/KEY: modified_base
<222> LOCATION: (426)..(426)
<223> OTHER INFORMATION: a, t, c, g, unknown or other
<220> FEATURE:
<221> NAME/KEY: modified_base
<222> LOCATION: (466)..(466)
<223> OTHER INFORMATION: a, t, c, g, unknown or other
<220> FEATURE:
<221> NAME/KEY: modified_base
<222> LOCATION: (478)..(478)
<223> OTHER INFORMATION: a, t, c, g, unknown or other
<220> FEATURE:
<221> NAME/KEY: modified_base
<222> LOCATION: (484)..(484)
<223> OTHER INFORMATION: a, t, c, g, unknown or other
<220> FEATURE:
<221> NAME/KEY: modified_base
<222> LOCATION: (487)..(487)

<223> OTHER INFORMATION: a, t, c, g, unknown or other
<220> FEATURE:
<221> NAME/KEY: modified_base
<222> LOCATION: (512)..(512)
<223> OTHER INFORMATION: a, t, c, g, unknown or other
<220> FEATURE:
<221> NAME/KEY: modified_base
<222> LOCATION: (516)..(516)
<223> OTHER INFORMATION: a, t, c, g, unknown or other
<220> FEATURE:
<221> NAME/KEY: modified_base
<222> LOCATION: (536)..(536)
<223> OTHER INFORMATION: a, t, c, g, unknown or other
<220> FEATURE:
<221> NAME/KEY: modified_base
<222> LOCATION: (576)..(576)
<223> OTHER INFORMATION: a, t, c, g, unknown or other

<400> SEQUENCE: 23

```
tgtggccttt tttttttttt tttttttttt tttttttttt tttttttttt tttttganaa     60

tttacntata tctttatata aangcntata tntttatana gcctntgnct aaaacanccg    120

ggcttgnttt ttnanttcat tcctnttcca aagggccngc cggncaaact caaaaanggn    180

catgccnaaa acttggnaaa actnttnctg ggacaggggg ngctntaaac gggncctgnn    240

tacatncttg ggcangcggn ttnttnctnt tgnagtcncc nncagcagtt cataagggna    300

natnttgnac tntcgcatgc cccaattgac tgngttcatg ctgtcgtaat ggaaaangtc    360

tgcnctgggt gtcctgngca ncccattttt tnggtaggca ggcagggagg caaatttgga    420

natganagga tcactgtcag ccaggtagtg cgaccgaggg gagccnttgg gggacatntc    480

atanccngct gggtgcaggg ctttcccgct gntggnggaa ctcccgggga gggggncagg    540

ggatttgcat aagaactcga cccggccctt attttntttc tttaaaat                 588
```

<210> SEQ ID NO 24
<211> LENGTH: 2459
<212> TYPE: DNA
<213> ORGANISM: Homo sapiens
<220> FEATURE:
<223> OTHER INFORMATION: hmfn-1864

<400> SEQUENCE: 24

```
taggcctgta cggaagtgtt acttctgctc taaaagctgc ggaattcctc gagcactgtt     60

ggcctactgg ggctgcgctt cggtcccgga cccgggccac ccacggggta gtgggtgctc    120

ctcggccccg gacattgcaa gccccagaag gcaagactaa ctcggtgttg ctcctcccgg    180

cgctgacttc gaggcccggc tatggacggc gagagcgagg tggatttttc tagcaacagc    240

ataacccctt tgtggcggag gcggtcgatt cctcagcccc accagcttct gggccggagc    300

aagccgaggc cccagtccta ccagagcccc aacgggttac taattacgga tttcccggtg    360

gaggacggag ggacgctccc cgcagcgcag attcccgccc aggtgcccac cgcctcggac    420

agcaggacgg tacataggag ccccctgctt ctgggcgccc agcggagagc ggtggccaat    480

ggtgggacgg catccccgga gtacagggct gcctctcctc gacttcgacg gcccaagtca    540

cccaagctcc ccaaagcggt gcctggcggc tccccgaaat ctccagcaaa tggcgcggtg    600

accttgcctg cgccgccgcc gccgccggtt ctgcgccccc cgcggactcc taacgcgccc    660

gccccctgca cccccgagga ggaccttact gggttgactg ccagcccggt gccttcgccc    720

actgcaaatg gccttgccgc taataacgac tctcctgggt caggttcgca gtccggccgg    780

aaggcaaagg accccgaacg ggggctctct cctgggcccc agaaaagttc ttcggaacaa    840

aaactccccc tccaaaggct gccctcccag gagaacgagc tcctcgagaa tccttccgtg    900
```

```
gttttgagta caaacagccc cgccgccctc aaagtgggga agcagcagat cattccgaag    960

agtctggcct cggaaattaa aataagtaaa tccaacaatc aaaatgtgga gccccacaag   1020

agactcctca aggtgcgcag catggtggag ggcctaggag gacccctggg tcacgcaggg   1080

gaggagagtg aggtcgataa cgacgtggat agcccagggt ctctgcggag aggcttgcgg   1140

tccacgtctt atcgcagggc agtggtcagt ggctttgatt ttgacagtcc taccagctcg   1200

aagaagaaga acagaatgtc ccagcctgtt ctgaaagtgg tgatggaaga caaggagaag   1260

ttttccagtc tgggaaggat aaagaaaaaa atgctgaaag gacaaggaac atttgatggg   1320

gaagaaaatg ctgtcctgta tcaaaactac aaggaaaagg cccttgacat tgattctgat   1380

gaagagtcag agcccaaaga acagaagtca gatgaaaaaa ttgtgattca ccataagcca   1440

ttgagatcca catggagcca actctctgcg gtgaagagaa aggttatctt aatagtcggt   1500

ttcatggaga tgaaggatgg gagattaaga gggggaaat gatttttact ggcagctata   1560

ttccctctct gttctatttg ctttaacaaa gggataaaac ctggcaaagt gtacattatt   1620

ggaggactca aatctgtatg tgacatgtcc caactactgt ccgctaacta gttatccaaa   1680

ttgtaaagct acagaagccc agttgagggg taagtgtgcc tggctcacac agcctgcacc   1740

ctgtcacctc ggcaatgagc cagtgtgggg cactggggac ttctaaccct tggattgctc   1800

tttttgacct gtgcatacct tctaattgta aaatatattt cagaccgtga gtaccttgag   1860

atctgagcaa ctgtgttaat gaagtaatag caatggtcca cagtgaaaga tgtgttgggg   1920

tttgcaaaac aagcattccg tcacctcttt aataatgtca cagacttttt aaaagagagg   1980

ctatcaagtt gtaatataat ctgtcatgtt ttatttagga aggaaggtaa atttgtgctt   2040

gcacggggat cattttgtat tatttttgct aatacccagt tgaagctaaa aagcaactat   2100

ttgaatcctg tgaattaatt tataagaatg ttaaacagct ttggaaatac atgcatctta   2160

tgaatcatag ccttatttag caagatcaat gttaaagtgt tgttatatgg caagtattta   2220

acacattcac agtgtttgtt tgatttcaac tgtgaattgt cttacagttt tttcaaacct   2280

agttgtttct atggacacct gctctgaatt gtacattgac ttcattacta aagaacaaaa   2340

atgttcattt ttgtcccagt aaattgagac tgcttgtaca ctttcagaaa aatatgtgaa   2400

tttataaaga ttttgtagat acttaaaaaa aaaaaaggcc acatgtgctc gagctgcag    2459
```

<210> SEQ ID NO 25
<211> LENGTH: 530
<212> TYPE: DNA
<213> ORGANISM: Homo sapiens
<220> FEATURE:
<223> OTHER INFORMATION: hmfn-1876-f

<400> SEQUENCE: 25

```
agcccaacaa tggcggcgcc cgcggagtcg ctgaggaggc ggaagactgg gtactcggat     60

ccggagcctg agtcgccgcc cgcgccgggg cgtgaccccg caggctctcc ggcccatctc    120

cacacgggca ccttctggct gacccggatc gtgctcctga aggccctagc cttcgtgtac    180

ttcgtggcat tcctggtggc tttccatcag aacaagcagc tcatcggtga caggggggctg   240

cttccctgca gagtgttcct gaagaacttc cagcagtact tccaggacag gacaagctgg    300

gaagtcttca gctacatgcc caccatcctc tggctgatgg actggtcaga catgaactcc    360

aacctggact tgctggctct tctcggactg ggcatctcgt ctttcgtact gatcacgggc    420

tgcgccaaca tgcttctcat ggctgccctg tggggcctct acatgtccct ggttaatgtg    480
```

-continued

```
ggccatgtct ggtactcttt cggatgggag tcccagcttc tggagacggg             530


<210> SEQ ID NO 26
<211> LENGTH: 446
<212> TYPE: DNA
<213> ORGANISM: Homo sapiens
<220> FEATURE:
<223> OTHER INFORMATION: hmfn-2073-f

<400> SEQUENCE: 26

acaagttgcc ggcagctgag cgccgcgcct cctcctgctc gcagccccct acgcccaccc    60

ggcggcggtg gccagcgcca ggacgcacat cccgcggaca ccgacccccc ggcgcgatcg   120

acagtctcgc cagcgtctcc tctgccaaaa cccagggctg gaagatgtgg cagccggcca   180

cggagcgcct gcagcacttt cagaccatgc tgaagtctaa attgaatgtc ttaacactga   240

aaaaggaacc tctcccagcg gtcatcttcc atgagccgga ggccattgag ctgtgcacga   300

ccacaccgct gatgaagaca aggactcaca gtggctgcaa ggttacctac ctgggcaaag   360

tctccaccac tggcatgcag tttttgtcag gctgcacaga aaagccagtc attgagctct   420

ggaagaagca cacgctagcc cgagag                                        446


<210> SEQ ID NO 27
<211> LENGTH: 520
<212> TYPE: DNA
<213> ORGANISM: Homo sapiens
<220> FEATURE:
<223> OTHER INFORMATION: hmfn-2073-r

<400> SEQUENCE: 27

tgtggccttt tttttttttt tttttttttt ttaatgcaaa catattttta ttaaagaatg    60

aatgcattta tgctaaagaa tagcttacat atgttgtaaa gcaacaagca tatcttcaag   120

aagtgagtcc tcctcaatat gactccatgc ttattctaca tgcctgaaaa ctgggcccac   180

acacaggggc acacgtacac gcacacaaac gcagatacgg acacacagat atgcagaccg   240

aaatgctgac accatcgctc tctagattgg attagctctc atttaaggct tcttaggtgc   300

cgcagtgccc ctaatattac caggattgaa aacagacttt taggaaggag cagcattact   360

tcgaaaagta gtcatctgct cttgtcctcc aatgtgtgta ttttaacaaa tacaatttca   420

ttctatgttg actctgtgtt tataatattt aaagaaccat gaaattaaga aatctcagga   480

ttgttttagt gagaacttcc cattcaaaat aaaaaaaaag                         520


<210> SEQ ID NO 28
<211> LENGTH: 456
<212> TYPE: DNA
<213> ORGANISM: Homo sapiens
<220> FEATURE:
<223> OTHER INFORMATION: hmfn-2121-f

<400> SEQUENCE: 28

aatataaata aataaataaa taataaataa ataaataagg taggcattgg cttaagggaa    60

tgctgtggct ggttagatct gtccagccca ataaaatttt tcccacactg gcaataaggc   120

tgttttgctt tcttatcatt tgtatgttca ctggagtagc aacttttaat ttccttcaag   180

aactttccct ttgcagtcac aacatggata accttggcac aggaagccta gcttttagcc   240

tatcttggct ttcgacatgc cttcctcact aagcttaatc atttctagct tttgatttta   300

agtaataatc tgtgactctt tctttcactt gaacacttag aggccattta aagttattaa   360
```

```
ttggcctaat ttcaatataa ttttgtctca gggaataggg aggcctgagg aaggagagag    420

aggggtgata gccagtgagt gcagcagtca gaccag                              456


<210> SEQ ID NO 29
<211> LENGTH: 485
<212> TYPE: DNA
<213> ORGANISM: Homo sapiens
<220> FEATURE:
<223> OTHER INFORMATION: hmfn-2121-r

<400> SEQUENCE: 29

tgtggccttt tttttttttt tttttggatt gaggaccaat tcacctgcaa atcaaggtaa     60

tcgaaccaag tgcctacatc agacatgata ggcaaagacc agatctgagg ggtcagaaaa    120

cactgacaac aatgatcaga gctaccactt taaagtagga aagaaggtag acaagcagga    180

tgccaatcaa agttcctgta agactttcct gaacaatcga aacgtatcta gctgacggca    240

gcttgtcttg tttccttttg caaaatggtt ctttccttgt gtcattccat tttgatgtat    300

gtgagcaaag attgcttgta tgaagatcag acaccttttg tgttaacact accaaagaaa    360

agttctgtct gtcttattct catgtttaaa aaattctggt gatggtgatg gttatgtttt    420

aagaagtact taaaagaata agactccaaa ggaaataaat gtcttttatt ctggagtcaa    480

agctt                                                                485


<210> SEQ ID NO 30
<211> LENGTH: 543
<212> TYPE: DNA
<213> ORGANISM: Homo sapiens
<220> FEATURE:
<223> OTHER INFORMATION: hmfn-2567-f

<400> SEQUENCE: 30

gactacaaaa taacatctac ctcctgatag caaaagaact gaggaagctc tttccactac     60

ggctgtattg cactgagaac tttgctgcag ccattcctgg tcatcgttgc tgggtccaca    120

tgctggacaa taatactgga tctggtaatg aaactggaat cctcagtgaa gatgccctct    180

tgagaatctc tatcccacta gactcaaatc tgaggccaga gaagtgtcgt cgctttgtcc    240

atccccagtg acagcttctt cacctgaatg ggactatcca cagcacaagt gaggcagaca    300

cagaaccctg tgtggatggc tgggtatatg atcaaagcta cttcccttcg accattgtga    360

ctaagtggga cctggtatgt gattatcagt cactgaaatc agtggttcaa ttcctacttc    420

tgactggaat gctggtggga ggcatcatag gtggccatgt ctcagacagg tttgggcgaa    480

gatttattct cagatggtgt ttgctccagc ttgccatcac tgacacctgc gctgccttcg    540

ctc                                                                  543


<210> SEQ ID NO 31
<211> LENGTH: 443
<212> TYPE: DNA
<213> ORGANISM: Homo sapiens
<220> FEATURE:
<223> OTHER INFORMATION: hmfn-2567-r

<400> SEQUENCE: 31

tgtggccttt tttttttttt ttttttaatt tatagttatt ttattaaatg tacatacagt     60

ttgaaaattg ctgaacctgg cctttgccct tcaatttgaa caatatcttt ataatattgt    120

aaactatacc agctatttgt ttaaaatata cagagagaaa attacaaaga aaaagtaatt    180

aaaattccac catggaaaag taactaacat catttagtga ctgtatttac aaagagatag    240
```

-continued

```
tcaatgttat ttagtatcta atctttccgt tttccagtgg cttattatgt caaaagtatc    300

atgtattaaa tgcatttata taggtctcta tttctggatt tattttgatt tctggttgca    360

tgtacagtat tgttttgact tttgcaactt tatgaattca tcacatggtg cttcatacac    420

cagccagcca catcctaatt ctg                                            443


<210> SEQ ID NO 32
<211> LENGTH: 529
<212> TYPE: DNA
<213> ORGANISM: Homo sapiens
<220> FEATURE:
<223> OTHER INFORMATION: hmfn-2729-f

<400> SEQUENCE: 32

agttggtgag ctagggtagc gcactacggt tcactcttgc tttctttgct tcacaggatt     60

ggagaaggtt tgtgttcccg acgccttggt agttggcata ggctaaagaa aagggatctc    120

agccccgagg aagggtcacc ctcctagaga tagctactac cccgtctcag gagaccctgg    180

tatttctaga gcacgctttg ctttcaccaa acccaaggag gtgacaggag gagccccgc     240

acaggaccta agaatgctgt gaccagaaga tgggatcgcg gaacagcagc agtgcaggat    300

ccgggtccgg agacccctcc gagggcttgc cccgaagagg ggctggcctg cgtcggagtg    360

aggaagagga agaagaggat gaagatgtgg atctggccca ggtactggcc tatctcctcc    420

gcagaggcca agtgaggttg gtgcagggag gaggtgcagc aaatttacaa ttcattcagg    480

ccctcttgga ctcagaggaa gagaatgaca gagcttggga tggtcgtct                 529


<210> SEQ ID NO 33
<211> LENGTH: 404
<212> TYPE: DNA
<213> ORGANISM: Homo sapiens
<220> FEATURE:
<223> OTHER INFORMATION: hmfn-2729-r

<400> SEQUENCE: 33

tgtggccttt tttttttttt tttttttttt ttcaggttcc cacacagttt attgagggag     60

ccaaagccag tgagaggacg aaggagtcct acttcaacct acttccttaa agctgtgtgc    120

ctccagcatg aagggacctt cccagaaggg cagggcctgc cctataaggg gccacatgaa    180

gccttgtgga gactcctgcc tctcatacca cagcctgtcc taccctaaag acccagacat    240

gacagcagac ataatcccca ccccaggagg gtgctgagga aacaccctta cccatgcccc    300

tcccctagag acctcaggaa gaaaggccag gacacctgtc ctgtgattgg ccagttgaat    360

cctcaacgtg aagacctggc aggcctggct gacaggtctg ttca                      404


<210> SEQ ID NO 34
<211> LENGTH: 871
<212> TYPE: DNA
<213> ORGANISM: Homo sapiens
<220> FEATURE:
<223> OTHER INFORMATION: hmft-0128

<400> SEQUENCE: 34

ttctaggcct gtacggaagt gttacttctg ctctaaaagc tgcggaattc ctcgagcact     60

gttggcctac tggaaaaata taaaaaatta gccaggcgtg gtggtgggca cctgtagtcc    120

cagcaactcg ggaggctgag gcaggagaat ggcgtgaact tgggaggcgg agcttgcggt    180

gagccaagat cgtgccactg cactctagcc tgggcaacag agcaagactg tctcaaaaaa    240
```

```
attaaaatta aaattaaaaa caaataatcc tgccttttac aggtgaaact cggggctgtc    300

catagcggct gggaccccgt ttcatccatc catgcttcct agaacacacg atgggctttc    360

cttacccatg cccaaggtgt gccctccgtc tggaatgccg ttccctgttt cccagatctc    420

ttgaactctg ggttctccca gccccttgtc cttccttcca gctgagccct ggccacactg    480

gggctgcctt tctctgactc tgtcttcccc aagtcagggg gctctctgag tgcagggtct    540

gatgctgagt cccacttagc ttggggtcag aaccaagggg tttaataaat aacccttgaa    600

aactggatcg gatgaattgg ctttcattgt gttcctagca tcttctcaaa tcaacttccc    660

aggactccag ggtgaaggag gaaaagaggc atggcccagg ccctggggtg tgggatatgg    720

tctccctagg ggatgacagt tgggatcaat ggcctgtgac ttctcctctc ccttccccca    780

tcctgggacc taactggaaa taaaaccttg actgttaaaa aaaaaaaaaa aaggccacat    840

gtgctcgagc tgcaggtcgc ggccgctaga c                                   871
```

```
<210> SEQ ID NO 35
<211> LENGTH: 1938
<212> TYPE: DNA
<213> ORGANISM: Homo sapiens
<220> FEATURE:
<223> OTHER INFORMATION: hmft-0141

<400> SEQUENCE: 35

taggcctgta cggaagtgtt acttctgctc taaaagctgc ggaattcctc gagcactgtt     60

ggcctactgg gtgcctgtct ccctccagca ctgccgaggt tctctgccga ggccaaccag    120

aaatacccct tggaagctgg aatcctgcaa caatggccca gggtgtcctc tggatcctac    180

tcggattgct actgtggtca gacccaggga cagcctccct gcccctgctc atggactctg    240

tcatccaggc cctggctgag ctggagcaga aagtgccagc tgccaaggcc agacacacag    300

cttctgcgtg gctgatgtca gctccaaact ctggccccca caatcgcctc taccacttcc    360

tgctgggggc atggagcctc aatgctacag agttggatcc ctgcccacta agcccagagc    420

tgttaggcct gaccaaggag gtggcccaac atgacgtacg agaagggaag gaatatgggg    480

tggtgctggc acctgatggc tcgaccgtgg ctgtggagcc tctgctggcg gggctggagg    540

cagggctgca agggcgcagg gtcataaatt tgcccttgga cagcatggct gccccttggg    600

agactggaga tacctttcca gatgttgtgg ccattgctcc agatgtaaga gccacctcct    660

ccccaggact cagggatggc tctccagatg tcaccactgc agatattgga gccaacactc    720

cagatgctac aaaaggctgt ccagatgtcc aagcttcctt gccagatgcc aaagccaagt    780

ccccaccgac catggtggac agcctcctgg cagtcaccct ggctggaaac ctgggcctga    840

ccttcctccg aggttcccag acccagagcc atccagacct gggaactgag ggctgctggg    900

accagctctc tgcccctcgg acctttacgc ttttggaccc caaggcatct ctgttaacca    960

aggccttcct caatggcgcc ctggatgggg tcatccttgg agactacctg agccggactc   1020

ctgagccccg gccatccctc agccacttgc tgagccagta ctatggggct ggggtggcca   1080

gagacccagg gttccgcagc aacttccgac ggcagaacgg tgctgctctg acttcagcct   1140

ccatcctggc ccagcaggtg tggggaaccc ttgtccttct acagaggctg gagccagtac   1200

acctccagct tcagtgcatg agccaagaac agctggccca ggtggctgcc aatgctacca   1260

aggaattcac tgaggccttc ctgggatgcc cggccatcca cccccgctgc cgctggggag   1320

cggcgcctta tcagggccgc ccgaagctgc tgcagctgcc gctgggattc ttgtacgtgc   1380

atcacaccta cgtgcctgca ccaccctgca cggacttcac gcgctgcgca gccaacatgc   1440
```

-continued

```
gctccatgca gcgctaccac caggacacgc aaggctgggg agacatcggc tacagtttcg   1500

tggtgggctc ggacggctac gtgtacgagg gacgcggctg gcactgggtg ggcgcccaca   1560

cgctcggcca caactcccgg ggcttcggcg tggccatagt gggcaactac accgcggcgc   1620

tgcccaccga ggccgctctg cgcacggtgc gcgacacgct cccgagttgt gcggtgcgcg   1680

ccggcctcct gcggccagac tacgcgctgc tgggccaccg ccagctggtg cgcaccgact   1740

gccccggcga cgcgctcttc gacctgctgc gcacctggcc gcacttcacc gcgactgtta   1800

agccaagacc tgccaggagt gtctctaaga gatccaggag ggagccaccc ccaaggaccc   1860

tgccagccac agacctccaa taaagacagc atggaaacaa aaaaaaaaaa aaaaaggcca   1920

catgtgctcg agctgcag                                                 1938
```

<210> SEQ ID NO 36
<211> LENGTH: 535
<212> TYPE: DNA
<213> ORGANISM: Homo sapiens
<220> FEATURE:
<223> OTHER INFORMATION: hmft-0656-f

<400> SEQUENCE: 36

```
aggagcgggg gtggggtcag tggagtgggc tcaggtcagg gtggaggggg actcctgagg     60

gatgaagtgg gcgatccaga ctcctagctt cccaccgagg cactaaggga atcagagtgg    120

gtcagcgagt acgggaagtg tggtccacga gggctggttc ctgagggaga atccacaagc    180

cccctcccct cttcagtgga tactgaagac tccctcgacg aaggacccgg ggccctggta    240

ttggagagtg atttgctact aggccaggat ctggagtttg aggaggaaga ggaagaggag    300

gaaggcgacg gcaacagtga ccagctcatg ggcttcgaga gagactcgga aggagactct    360

ctgggggcca ggcctgggct tccctatggg ctgagcgacg atgagtctgg gggcggccgg    420

gcactaagtg cggagagtga agttgaggag ccagccaggg gtccagggga ggccaggggt    480

gagaggccag gcccagcctg ccagctgtgt tggggggccg acaggtgagg ggccg         535
```

<210> SEQ ID NO 37
<211> LENGTH: 610
<212> TYPE: DNA
<213> ORGANISM: Homo sapiens
<220> FEATURE:
<223> OTHER INFORMATION: hmft-0656-r
<220> FEATURE:
<221> NAME/KEY: modified_base
<222> LOCATION: (55)..(55)
<223> OTHER INFORMATION: a, t, c, g, unknown or other
<220> FEATURE:
<221> NAME/KEY: modified_base
<222> LOCATION: (69)..(69)
<223> OTHER INFORMATION: a, t, c, g, unknown or other
<220> FEATURE:
<221> NAME/KEY: modified_base
<222> LOCATION: (74)..(74)
<223> OTHER INFORMATION: a, t, c, g, unknown or other
<220> FEATURE:
<221> NAME/KEY: modified_base
<222> LOCATION: (79)..(79)
<223> OTHER INFORMATION: a, t, c, g, unknown or other
<220> FEATURE:
<221> NAME/KEY: modified_base
<222> LOCATION: (86)..(86)
<223> OTHER INFORMATION: a, t, c, g, unknown or other
<220> FEATURE:
<221> NAME/KEY: modified_base
<222> LOCATION: (100)..(100)
<223> OTHER INFORMATION: a, t, c, g, unknown or other
<220> FEATURE:

-continued

<221> NAME/KEY: modified_base
<222> LOCATION: (105)..(105)
<223> OTHER INFORMATION: a, t, c, g, unknown or other
<220> FEATURE:
<221> NAME/KEY: modified_base
<222> LOCATION: (107)..(107)
<223> OTHER INFORMATION: a, t, c, g, unknown or other
<220> FEATURE:
<221> NAME/KEY: modified_base
<222> LOCATION: (109)..(109)
<223> OTHER INFORMATION: a, t, c, g, unknown or other
<220> FEATURE:
<221> NAME/KEY: modified_base
<222> LOCATION: (114)..(114)
<223> OTHER INFORMATION: a, t, c, g, unknown or other
<220> FEATURE:
<221> NAME/KEY: modified_base
<222> LOCATION: (130)..(130)
<223> OTHER INFORMATION: a, t, c, g, unknown or other
<220> FEATURE:
<221> NAME/KEY: modified_base
<222> LOCATION: (137)..(137)
<223> OTHER INFORMATION: a, t, c, g, unknown or other
<220> FEATURE:
<221> NAME/KEY: modified_base
<222> LOCATION: (148)..(148)
<223> OTHER INFORMATION: a, t, c, g, unknown or other
<220> FEATURE:
<221> NAME/KEY: modified_base
<222> LOCATION: (150)..(151)
<223> OTHER INFORMATION: a, t, c, g, unknown or other
<220> FEATURE:
<221> NAME/KEY: modified_base
<222> LOCATION: (157)..(157)
<223> OTHER INFORMATION: a, t, c, g, unknown or other
<220> FEATURE:
<221> NAME/KEY: modified_base
<222> LOCATION: (165)..(165)
<223> OTHER INFORMATION: a, t, c, g, unknown or other
<220> FEATURE:
<221> NAME/KEY: modified_base
<222> LOCATION: (179)..(179)
<223> OTHER INFORMATION: a, t, c, g, unknown or other
<220> FEATURE:
<221> NAME/KEY: modified_base
<222> LOCATION: (181)..(181)
<223> OTHER INFORMATION: a, t, c, g, unknown or other
<220> FEATURE:
<221> NAME/KEY: modified_base
<222> LOCATION: (184)..(184)
<223> OTHER INFORMATION: a, t, c, g, unknown or other
<220> FEATURE:
<221> NAME/KEY: modified_base
<222> LOCATION: (186)..(186)
<223> OTHER INFORMATION: a, t, c, g, unknown or other
<220> FEATURE:
<221> NAME/KEY: modified_base
<222> LOCATION: (196)..(196)
<223> OTHER INFORMATION: a, t, c, g, unknown or other
<220> FEATURE:
<221> NAME/KEY: modified_base
<222> LOCATION: (203)..(203)
<223> OTHER INFORMATION: a, t, c, g, unknown or other
<220> FEATURE:
<221> NAME/KEY: modified_base
<222> LOCATION: (205)..(205)
<223> OTHER INFORMATION: a, t, c, g, unknown or other
<220> FEATURE:
<221> NAME/KEY: modified_base
<222> LOCATION: (223)..(223)
<223> OTHER INFORMATION: a, t, c, g, unknown or other
<220> FEATURE:
<221> NAME/KEY: modified_base
<222> LOCATION: (225)..(225)
<223> OTHER INFORMATION: a, t, c, g, unknown or other
<220> FEATURE:
<221> NAME/KEY: modified_base
<222> LOCATION: (235)..(235)
<223> OTHER INFORMATION: a, t, c, g, unknown or other
<220> FEATURE:
<221> NAME/KEY: modified_base
<222> LOCATION: (245)..(245)
<223> OTHER INFORMATION: a, t, c, g, unknown or other
<220> FEATURE:
<221> NAME/KEY: modified_base
<222> LOCATION: (254)..(254)
<223> OTHER INFORMATION: a, t, c, g, unknown or other
<220> FEATURE:
<221> NAME/KEY: modified_base
<222> LOCATION: (259)..(259)
<223> OTHER INFORMATION: a, t, c, g, unknown or other
<220> FEATURE:
<221> NAME/KEY: modified_base
<222> LOCATION: (262)..(263)
<223> OTHER INFORMATION: a, t, c, g, unknown or other
<220> FEATURE:
<221> NAME/KEY: modified_base
<222> LOCATION: (270)..(270)
<223> OTHER INFORMATION: a, t, c, g, unknown or other
<220> FEATURE:
<221> NAME/KEY: modified_base
<222> LOCATION: (274)..(274)
<223> OTHER INFORMATION: a, t, c, g, unknown or other
<220> FEATURE:
<221> NAME/KEY: modified_base
<222> LOCATION: (279)..(279)
<223> OTHER INFORMATION: a, t, c, g, unknown or other
<220> FEATURE:
<221> NAME/KEY: modified_base
<222> LOCATION: (281)..(281)
<223> OTHER INFORMATION: a, t, c, g, unknown or other
<220> FEATURE:
<221> NAME/KEY: modified_base
<222> LOCATION: (285)..(285)
<223> OTHER INFORMATION: a, t, c, g, unknown or other
<220> FEATURE:
<221> NAME/KEY: modified_base
<222> LOCATION: (295)..(296)
<223> OTHER INFORMATION: a, t, c, g, unknown or other
<220> FEATURE:
<221> NAME/KEY: modified_base
<222> LOCATION: (310)..(310)
<223> OTHER INFORMATION: a, t, c, g, unknown or other
<220> FEATURE:
<221> NAME/KEY: modified_base
<222> LOCATION: (315)..(315)
<223> OTHER INFORMATION: a, t, c, g, unknown or other
<220> FEATURE:
<221> NAME/KEY: modified_base
<222> LOCATION: (322)..(322)
<223> OTHER INFORMATION: a, t, c, g, unknown or other
<220> FEATURE:
<221> NAME/KEY: modified_base
<222> LOCATION: (325)..(325)
<223> OTHER INFORMATION: a, t, c, g, unknown or other
<220> FEATURE:
<221> NAME/KEY: modified_base
<222> LOCATION: (331)..(331)
<223> OTHER INFORMATION: a, t, c, g, unknown or other
<220> FEATURE:
<221> NAME/KEY: modified_base
<222> LOCATION: (349)..(349)
<223> OTHER INFORMATION: a, t, c, g, unknown or other
<220> FEATURE:
<221> NAME/KEY: modified_base
<222> LOCATION: (351)..(351)
<223> OTHER INFORMATION: a, t, c, g, unknown or other
<220> FEATURE:
<221> NAME/KEY: modified_base
<222> LOCATION: (355)..(355)
<223> OTHER INFORMATION: a, t, c, g, unknown or other
<220> FEATURE:
<221> NAME/KEY: modified_base
<222> LOCATION: (359)..(359)
<223> OTHER INFORMATION: a, t, c, g, unknown or other
<220> FEATURE:
<221> NAME/KEY: modified_base
<222> LOCATION: (361)..(361)

<223> OTHER INFORMATION: a, t, c, g, unknown or other
<220> FEATURE:
<221> NAME/KEY: modified_base
<222> LOCATION: (365)..(365)
<223> OTHER INFORMATION: a, t, c, g, unknown or other
<220> FEATURE:
<221> NAME/KEY: modified_base
<222> LOCATION: (367)..(367)
<223> OTHER INFORMATION: a, t, c, g, unknown or other
<220> FEATURE:
<221> NAME/KEY: modified_base
<222> LOCATION: (369)..(369)
<223> OTHER INFORMATION: a, t, c, g, unknown or other
<220> FEATURE:
<221> NAME/KEY: modified_base
<222> LOCATION: (371)..(371)
<223> OTHER INFORMATION: a, t, c, g, unknown or other
<220> FEATURE:
<221> NAME/KEY: modified_base
<222> LOCATION: (380)..(380)
<223> OTHER INFORMATION: a, t, c, g, unknown or other
<220> FEATURE:
<221> NAME/KEY: modified_base
<222> LOCATION: (386)..(386)
<223> OTHER INFORMATION: a, t, c, g, unknown or other
<220> FEATURE:
<221> NAME/KEY: modified_base
<222> LOCATION: (388)..(389)
<223> OTHER INFORMATION: a, t, c, g, unknown or other
<220> FEATURE:
<221> NAME/KEY: modified_base
<222> LOCATION: (405)..(405)
<223> OTHER INFORMATION: a, t, c, g, unknown or other
<220> FEATURE:
<221> NAME/KEY: modified_base
<222> LOCATION: (409)..(409)
<223> OTHER INFORMATION: a, t, c, g, unknown or other
<220> FEATURE:
<221> NAME/KEY: modified_base
<222> LOCATION: (421)..(421)
<223> OTHER INFORMATION: a, t, c, g, unknown or other
<220> FEATURE:
<221> NAME/KEY: modified_base
<222> LOCATION: (431)..(431)
<223> OTHER INFORMATION: a, t, c, g, unknown or other
<220> FEATURE:
<221> NAME/KEY: modified_base
<222> LOCATION: (442)..(442)
<223> OTHER INFORMATION: a, t, c, g, unknown or other
<220> FEATURE:
<221> NAME/KEY: modified_base
<222> LOCATION: (444)..(444)
<223> OTHER INFORMATION: a, t, c, g, unknown or other
<220> FEATURE:
<221> NAME/KEY: modified_base
<222> LOCATION: (448)..(448)
<223> OTHER INFORMATION: a, t, c, g, unknown or other
<220> FEATURE:
<221> NAME/KEY: modified_base
<222> LOCATION: (462)..(462)
<223> OTHER INFORMATION: a, t, c, g, unknown or other
<220> FEATURE:
<221> NAME/KEY: modified_base
<222> LOCATION: (470)..(470)
<223> OTHER INFORMATION: a, t, c, g, unknown or other
<220> FEATURE:
<221> NAME/KEY: modified_base
<222> LOCATION: (472)..(472)
<223> OTHER INFORMATION: a, t, c, g, unknown or other
<220> FEATURE:
<221> NAME/KEY: modified_base
<222> LOCATION: (474)..(474)
<223> OTHER INFORMATION: a, t, c, g, unknown or other
<220> FEATURE:
<221> NAME/KEY: modified_base
<222> LOCATION: (497)..(497)
<223> OTHER INFORMATION: a, t, c, g, unknown or other
<220> FEATURE:
<221> NAME/KEY: modified_base
<222> LOCATION: (515)..(515)
<223> OTHER INFORMATION: a, t, c, g, unknown or other
<220> FEATURE:
<221> NAME/KEY: modified_base
<222> LOCATION: (526)..(526)
<223> OTHER INFORMATION: a, t, c, g, unknown or other
<220> FEATURE:
<221> NAME/KEY: modified_base
<222> LOCATION: (542)..(542)
<223> OTHER INFORMATION: a, t, c, g, unknown or other
<220> FEATURE:
<221> NAME/KEY: modified_base
<222> LOCATION: (579)..(580)
<223> OTHER INFORMATION: a, t, c, g, unknown or other
<220> FEATURE:
<221> NAME/KEY: modified_base
<222> LOCATION: (589)..(589)
<223> OTHER INFORMATION: a, t, c, g, unknown or other
<220> FEATURE:
<221> NAME/KEY: modified_base
<222> LOCATION: (591)..(591)
<223> OTHER INFORMATION: a, t, c, g, unknown or other

<400> SEQUENCE: 37
tgtggccttt tttttttttt tttttttttt tttttttttt tttttttttt ggtangggtt 60
cctttattnt aaancactna aataanttaa ataaacaggn gggangntng gcantccccc 120
aaccggtttn tccacanccc ctgggggnan nggaggngaa tacanggccc tttttactna 180
nctngngaaa tgcctnaatc aangnaaggg cccctggtcc atntnggccc ccccncccat 240
ggggntgggc tggnccttnt anngcctacn ttantctgng ngganccccct ggccnncggg 300 ggaaaaaaan ggggnttttg gnccntctgt ntaaaacatg gggaaaaang ncctnattna 360
ngatnantnt ntgtggacan cccggntnnc aacaatcccc aaggntggng ggccccgaaa 420
nctcaaaaca nagggtgggc tntnaagngg ggcccaaccc tnaaaagcan ananaccaag 480
cccttctgcc ccaccgnggg catgcacctt ttggnggcgc ttgtanttgt cccaatggcc 540
cntggtataa gcgcaagtgg cacaacggaa aggcttttnn cctgtgtgnc ncaacatgtg 600
acctttgag 610

<210> SEQ ID NO 38
<211> LENGTH: 595
<212> TYPE: DNA
<213> ORGANISM: Homo sapiens
<220> FEATURE:
<223> OTHER INFORMATION: hmft-0673-f

<400> SEQUENCE: 38
actagctatg agtcccgctc gggcaattac agcgtcacgg agaacatgtt ctgtgctggc 60
tactacgagg gcggcaaaga cacgtgcctt ggagatagcg gtggggcctt tgtcatcttt 120
gatgacttga gccagcgctg ggtggtgcaa ggcctggtgt cctggggggg acctgaagaa 180
tgcggcagca agcaggtcta tggagtctac acaaaggtct ccaattacgt ggactgggtg 240
tgggagcaga tgggcttacc acaaagtgtt gtggagcccc aggtggaacg gtgagctgac 300
ttacttcctc ggggcctgcc tcccctgagc gaagctacac cgcacttccg acagcacact 360
ccacattact tatcagacca tatggaatgg aacacactga cctagcggtg gcttctccta 420
ccgagacagc ccccaggacc ctgagaggca gagtgtggta tagggaaaag gctccaggca 480
ggagacctgt gttcctgagc ttgtccaagt ctctttccct gtctgggcct cactctaccc 540
agtaatacaa tgcaggagct caaccaaggc ctctgtgcca atcccagcac tcctt 595

<210> SEQ ID NO 39

-continued

<211> LENGTH: 469
<212> TYPE: DNA
<213> ORGANISM: Homo sapiens
<220> FEATURE:
<223> OTHER INFORMATION: hmft-0673-r

<400> SEQUENCE: 39

```
tgtggccttt tttttttttt tttttgttgg ttatccacga gggtttattt ccacttgaga     60

cccctgatgg gagcaacaat gcagaggccc tttacagaat ggtgaagcat atgatataaa    120

agatacaaaa tataacatca tttacatgtg ccattcatag acaaaggagt gtgtttgatg    180

agccggttgg agaagtggac acttcccaat cattccctct caggggcttc tctggctgcc    240

ttgctctgat ggagattttc aggagagaga gctccaggga gaaggagaac aatcagccct    300

gtgagggcca gagaggctgc tagcagtcag ggaagctctg agtgctccag ctagaaggaa    360

cctgcagggg accttatgcc agcctgttgc tgacggagaa ccagagactc agacaaagaa    420

aatgattttt caaaggttat acagccagtt gggggcagag cagggacta                469
```

<210> SEQ ID NO 40
<211> LENGTH: 1926
<212> TYPE: DNA
<213> ORGANISM: Homo sapiens
<220> FEATURE:
<223> OTHER INFORMATION: hmft-0700

<400> SEQUENCE: 40

```
taggcctgta cggaagtgtt acttctgctc taaaagctgc ggaattcctc gagcactgtt     60

ggcctactgg agtgggcgcc gcggggcaca cgctgggcca aggtgcaggc ggccagggtg    120

ggagactgtt cgccccgccc tgagtactcc tatcttgttt ctccacctgt tcgggagttg    180

gagatgtgca cctaaaggag gcgcatctgg ggacggacac atctggcact gaggccctcg    240

ccacctgcct cgccacctgg cgaccctgac cccaccacac tgccttgaga gtcgctcaaa    300

agtagggccc cagggctcgc agcagcatgg gcaccgagaa agaaagccca gagcccgact    360

gccagaaaca gttccaggct gcagtgagcg tcatccagaa cctgcccaag aacggttctt    420

accgccccctc ctatgaagag atgctgcgat tctacagtta ctacaagcag gccaccatgg    480

ggccctgcct ggtccccggg cccgggttct gggaccccat tggacgatat aagtgggacg    540

cctggaacag tctgggcaag atgagcaggg aggaggccat gtctgcctac atcactgaaa    600

tgaaactggt ggcacagaag gtgatcgaca cagtgcccct gggtgaggtg gcagaggaca    660

tgtttggtta cttcgagccc ctgtaccagg tgatccctga catgccgagg cccccagaga    720

ccttcctgag aagggtcaca ggttggaaag agcaggttgt gaatggagat gttggggctg    780

tttcagagcc tccctgcctc cccaaggaac cggcaccccc aagcccagct tccctctggg    840

cagtaactct accaacccct ccacagagtc ccattcatcc agggacctgg actccgaggt    900

tttctgtgat tccctggagc agctggagcc tgagctggtt tggacagagc agcgggcagc    960

atctggagga aagcgtgatc ccaggaacag ccccgtgccc cccacaaaga aagaggggtt   1020

gcggggcagc ccgccggggc cccaggagtt ggacgtgtgg ctgctgggga cagttcgagc   1080

actacaggag agcatgcagg aggtgcaggc gagggtgcag agcctggaga gcatgccccg   1140

gccccctgag cagaggccgc agcccaggcc cagtgctcgg ccatggcccc ttgggctccc   1200

ggggcccgcg ctgctcttct tcctcctgtg gcccttcgtc gtccagtggc tcttccgaat   1260

gtttcggacc caaaagaggt gactgtcagt ggaggggtct ctgcagccaa ctgagactat   1320

cttgctgtgc cctgagcctt cctagggttt agaagaacag cattcaaaat tccccgtcct   1380
```

-continued gtcagtgttt gccttcgcac ctcctcccct aaagcagcgc ggggggcaaa taagacccca 1440
cccctccctg cagcttcaca gggacgcttc cttccctccc cgcaaccacc ccaggctccc 1500
ctgggaggct gcagttgtgg tacacgtccc cggtgctggg ttggccgtga ctcgggggcg 1560
gggcgatcgg gtctcagccc ctgccttccc cagtctctgg gtcacccgaa ttttcccacc 1620
cctgcttctc cccgaggagg ttgagctctt gagcaagttg ggacttgggc cggggcctgg 1680
aagaatgatt ggctgggagg ccgcgggagg gaggccagga ggcccggacc agttgggagg 1740
agtgagcagg ccccggggga gggggatgag cgcagtttgc tcgctttcct cccctgccgg 1800
ccccctccgc ccccacacac actcgggacg tcttcattga agattcactt acaaaggaat 1860
gtttcactaa ataaaagaaa accagaaaaa aaaaaaaaaa aaaggccaca tgtgctcgag 1920
ctgcag 1926

<210> SEQ ID NO 41
<211> LENGTH: 560
<212> TYPE: DNA
<213> ORGANISM: Homo sapiens
<220> FEATURE:
<223> OTHER INFORMATION: hmft-1163-f

<400> SEQUENCE: 41
atattcaaaa aaatctgaac tgtggacggc ccaggaaact attgtctatt tgggggacta 60
cttgactgtg aagaaaaaag gcagacaaag aaatgctttt tgggttcatc atcttcatca 120
agaagaaatt ctggggaggt atgttgggaa agactataag gagcagaagg ggctctggca 180
ccacttcact gatgtggagc ggcagatgac cgcacagcac tatgtgacag aatttaacaa 240
gagactctat gaacaaaaca ttcccaccca gatattctac atcccatcca caatactact 300
gattttagag gacaagacaa taaagggatg tatcagtgtg gagccttaca tactgggaga 360
atttgtaaaa ttgtcaaata acacgaaagt ggtgaaaaca gaatacaaag ccacagaata 420
tggcttggcc tatggccatt tttcttatga gttttctaat catagagatg ttgtggtcga 480
tttacaaggt tgggtaaccg gtaatggaaa aggactcatc tacctcacag atccccagat 540
tcactccgtt gatcagaaag 560

<210> SEQ ID NO 42
<211> LENGTH: 625
<212> TYPE: DNA
<213> ORGANISM: Homo sapiens
<220> FEATURE:
<223> OTHER INFORMATION: hmft-1163-r
<220> FEATURE:
<221> NAME/KEY: modified_base
<222> LOCATION: (83)..(83)
<223> OTHER INFORMATION: a, t, c, g, unknown or other
<220> FEATURE:
<221> NAME/KEY: modified_base
<222> LOCATION: (101)..(101)
<223> OTHER INFORMATION: a, t, c, g, unknown or other
<220> FEATURE:
<221> NAME/KEY: modified_base
<222> LOCATION: (104)..(104)
<223> OTHER INFORMATION: a, t, c, g, unknown or other
<220> FEATURE:
<221> NAME/KEY: modified_base
<222> LOCATION: (125)..(125)
<223> OTHER INFORMATION: a, t, c, g, unknown or other
<220> FEATURE:
<221> NAME/KEY: modified_base
<222> LOCATION: (128)..(128)
<223> OTHER INFORMATION: a, t, c, g, unknown or other
<220> FEATURE:

-continued

<221> NAME/KEY: modified_base
<222> LOCATION: (163)..(163)
<223> OTHER INFORMATION: a, t, c, g, unknown or other
<220> FEATURE:
<221> NAME/KEY: modified_base
<222> LOCATION: (169)..(169)
<223> OTHER INFORMATION: a, t, c, g, unknown or other
<220> FEATURE:
<221> NAME/KEY: modified_base
<222> LOCATION: (194)..(194)
<223> OTHER INFORMATION: a, t, c, g, unknown or other
<220> FEATURE:
<221> NAME/KEY: modified_base
<222> LOCATION: (201)..(201)
<223> OTHER INFORMATION: a, t, c, g, unknown or other
<220> FEATURE:
<221> NAME/KEY: modified_base
<222> LOCATION: (203)..(203)
<223> OTHER INFORMATION: a, t, c, g, unknown or other
<220> FEATURE:
<221> NAME/KEY: modified_base
<222> LOCATION: (205)..(205)
<223> OTHER INFORMATION: a, t, c, g, unknown or other
<220> FEATURE:
<221> NAME/KEY: modified_base
<222> LOCATION: (216)..(216)
<223> OTHER INFORMATION: a, t, c, g, unknown or other
<220> FEATURE:
<221> NAME/KEY: modified_base
<222> LOCATION: (221)..(221)
<223> OTHER INFORMATION: a, t, c, g, unknown or other
<220> FEATURE:
<221> NAME/KEY: modified_base
<222> LOCATION: (223)..(223)
<223> OTHER INFORMATION: a, t, c, g, unknown or other
<220> FEATURE:
<221> NAME/KEY: modified_base
<222> LOCATION: (226)..(226)
<223> OTHER INFORMATION: a, t, c, g, unknown or other
<220> FEATURE:
<221> NAME/KEY: modified_base
<222> LOCATION: (235)..(235)
<223> OTHER INFORMATION: a, t, c, g, unknown or other
<220> FEATURE:
<221> NAME/KEY: modified_base
<222> LOCATION: (244)..(244)
<223> OTHER INFORMATION: a, t, c, g, unknown or other
<220> FEATURE:
<221> NAME/KEY: modified_base
<222> LOCATION: (262)..(262)
<223> OTHER INFORMATION: a, t, c, g, unknown or other
<220> FEATURE:
<221> NAME/KEY: modified_base
<222> LOCATION: (269)..(269)
<223> OTHER INFORMATION: a, t, c, g, unknown or other
<220> FEATURE:
<221> NAME/KEY: modified_base
<222> LOCATION: (278)..(278)
<223> OTHER INFORMATION: a, t, c, g, unknown or other
<220> FEATURE:
<221> NAME/KEY: modified_base
<222> LOCATION: (321)..(321)
<223> OTHER INFORMATION: a, t, c, g, unknown or other
<220> FEATURE:
<221> NAME/KEY: modified_base
<222> LOCATION: (334)..(334)
<223> OTHER INFORMATION: a, t, c, g, unknown or other
<220> FEATURE:
<221> NAME/KEY: modified_base
<222> LOCATION: (351)..(351)
<223> OTHER INFORMATION: a, t, c, g, unknown or other
<220> FEATURE:
<221> NAME/KEY: modified_base
<222> LOCATION: (369)..(369)
<223> OTHER INFORMATION: a, t, c, g, unknown or other
<220> FEATURE:
<221> NAME/KEY: modified_base
<222> LOCATION: (374)..(375)
<223> OTHER INFORMATION: a, t, c, g, unknown or other

```
<220> FEATURE:
<221> NAME/KEY: modified_base
<222> LOCATION: (381)..(383)
<223> OTHER INFORMATION: a, t, c, g, unknown or other
<220> FEATURE:
<221> NAME/KEY: modified_base
<222> LOCATION: (386)..(387)
<223> OTHER INFORMATION: a, t, c, g, unknown or other
<220> FEATURE:
<221> NAME/KEY: modified_base
<222> LOCATION: (402)..(402)
<223> OTHER INFORMATION: a, t, c, g, unknown or other
<220> FEATURE:
<221> NAME/KEY: modified_base
<222> LOCATION: (412)..(414)
<223> OTHER INFORMATION: a, t, c, g, unknown or other
<220> FEATURE:
<221> NAME/KEY: modified_base
<222> LOCATION: (425)..(425)
<223> OTHER INFORMATION: a, t, c, g, unknown or other
<220> FEATURE:
<221> NAME/KEY: modified_base
<222> LOCATION: (432)..(432)
<223> OTHER INFORMATION: a, t, c, g, unknown or other
<220> FEATURE:
<221> NAME/KEY: modified_base
<222> LOCATION: (437)..(437)
<223> OTHER INFORMATION: a, t, c, g, unknown or other
<220> FEATURE:
<221> NAME/KEY: modified_base
<222> LOCATION: (448)..(449)
<223> OTHER INFORMATION: a, t, c, g, unknown or other
<220> FEATURE:
<221> NAME/KEY: modified_base
<222> LOCATION: (456)..(456)
<223> OTHER INFORMATION: a, t, c, g, unknown or other
<220> FEATURE:
<221> NAME/KEY: modified_base
<222> LOCATION: (458)..(458)
<223> OTHER INFORMATION: a, t, c, g, unknown or other
<220> FEATURE:
<221> NAME/KEY: modified_base
<222> LOCATION: (464)..(464)
<223> OTHER INFORMATION: a, t, c, g, unknown or other
<220> FEATURE:
<221> NAME/KEY: modified_base
<222> LOCATION: (466)..(466)
<223> OTHER INFORMATION: a, t, c, g, unknown or other
<220> FEATURE:
<221> NAME/KEY: modified_base
<222> LOCATION: (470)..(470)
<223> OTHER INFORMATION: a, t, c, g, unknown or other
<220> FEATURE:
<221> NAME/KEY: modified_base
<222> LOCATION: (473)..(473)
<223> OTHER INFORMATION: a, t, c, g, unknown or other
<220> FEATURE:
<221> NAME/KEY: modified_base
<222> LOCATION: (485)..(485)
<223> OTHER INFORMATION: a, t, c, g, unknown or other
<220> FEATURE:
<221> NAME/KEY: modified_base
<222> LOCATION: (499)..(499)
<223> OTHER INFORMATION: a, t, c, g, unknown or other
<220> FEATURE:
<221> NAME/KEY: modified_base
<222> LOCATION: (505)..(505)
<223> OTHER INFORMATION: a, t, c, g, unknown or other
<220> FEATURE:
<221> NAME/KEY: modified_base
<222> LOCATION: (508)..(508)
<223> OTHER INFORMATION: a, t, c, g, unknown or other
<220> FEATURE:
<221> NAME/KEY: modified_base
<222> LOCATION: (512)..(512)
<223> OTHER INFORMATION: a, t, c, g, unknown or other
<220> FEATURE:
<221> NAME/KEY: modified_base
<222> LOCATION: (525)..(525)
```

<223> OTHER INFORMATION: a, t, c, g, unknown or other
<220> FEATURE:
<221> NAME/KEY: modified_base
<222> LOCATION: (527)..(527)
<223> OTHER INFORMATION: a, t, c, g, unknown or other
<220> FEATURE:
<221> NAME/KEY: modified_base
<222> LOCATION: (530)..(531)
<223> OTHER INFORMATION: a, t, c, g, unknown or other
<220> FEATURE:
<221> NAME/KEY: modified_base
<222> LOCATION: (536)..(536)
<223> OTHER INFORMATION: a, t, c, g, unknown or other
<220> FEATURE:
<221> NAME/KEY: modified_base
<222> LOCATION: (539)..(540)
<223> OTHER INFORMATION: a, t, c, g, unknown or other
<220> FEATURE:
<221> NAME/KEY: modified_base
<222> LOCATION: (547)..(547)
<223> OTHER INFORMATION: a, t, c, g, unknown or other
<220> FEATURE:
<221> NAME/KEY: modified_base
<222> LOCATION: (549)..(549)
<223> OTHER INFORMATION: a, t, c, g, unknown or other
<220> FEATURE:
<221> NAME/KEY: modified_base
<222> LOCATION: (553)..(553)
<223> OTHER INFORMATION: a, t, c, g, unknown or other
<220> FEATURE:
<221> NAME/KEY: modified_base
<222> LOCATION: (557)..(557)
<223> OTHER INFORMATION: a, t, c, g, unknown or other
<220> FEATURE:
<221> NAME/KEY: modified_base
<222> LOCATION: (577)..(577)
<223> OTHER INFORMATION: a, t, c, g, unknown or other
<220> FEATURE:
<221> NAME/KEY: modified_base
<222> LOCATION: (586)..(586)
<223> OTHER INFORMATION: a, t, c, g, unknown or other
<220> FEATURE:
<221> NAME/KEY: modified_base
<222> LOCATION: (589)..(589)
<223> OTHER INFORMATION: a, t, c, g, unknown or other
<220> FEATURE:
<221> NAME/KEY: modified_base
<222> LOCATION: (596)..(596)
<223> OTHER INFORMATION: a, t, c, g, unknown or other
<220> FEATURE:
<221> NAME/KEY: modified_base
<222> LOCATION: (602)..(602)
<223> OTHER INFORMATION: a, t, c, g, unknown or other
<220> FEATURE:
<221> NAME/KEY: modified_base
<222> LOCATION: (605)..(607)
<223> OTHER INFORMATION: a, t, c, g, unknown or other
<220> FEATURE:
<221> NAME/KEY: modified_base
<222> LOCATION: (609)..(609)
<223> OTHER INFORMATION: a, t, c, g, unknown or other
<220> FEATURE:
<221> NAME/KEY: modified_base
<222> LOCATION: (612)..(612)
<223> OTHER INFORMATION: a, t, c, g, unknown or other
<220> FEATURE:
<221> NAME/KEY: modified_base
<222> LOCATION: (616)..(616)
<223> OTHER INFORMATION: a, t, c, g, unknown or other
<220> FEATURE:
<221> NAME/KEY: modified_base
<222> LOCATION: (619)..(619)
<223> OTHER INFORMATION: a, t, c, g, unknown or other
<220> FEATURE:
<221> NAME/KEY: modified_base
<222> LOCATION: (621)..(621)
<223> OTHER INFORMATION: a, t, c, g, unknown or other

<400> SEQUENCE: 42

```
tgtggccttt tttttttttt tttttttttt tttttttttt ttttactttt attttaagtt     60

caggggtaca tgtgcaggtt tgngtcatgg gggtttgttg ngcnaattac ttcatcaccc    120

aggtnttnag cctagtaccc attagttatt tttcctgatc ctntccctnc tcccactgtc    180

caccctttga taanccctgg ngngngttgt tccctntatg ngnccnccta ctctnatcac    240

ttanctctca cctataagtg anaacaagng gtatttantt ttctgttttt gcattagttt    300

gctaaaaata atggcctcca nctttatcca tgtncctgca aaggacatga nctcattctt    360

ttttatggnt accnngggat nnngcnnggc tttgtgtccc cnccccaatc tnnnctcgaa    420

tttgnaatcc cntaatnccc atgtgtcnng ggaaanancc tggntngggn ggnaactggg    480

gcaanttctt ttcccatgnt gttcntcntg anaagtgaat gaatncncan naaatntgnn    540

ggctttnana aanccenggc ctttccccct gggtggnacc ttaatnccnt tttccngcct    600

anccnnntna anaagnggnc ntttt                                          625
```

```
<210> SEQ ID NO 43
<211> LENGTH: 617
<212> TYPE: DNA
<213> ORGANISM: Homo sapiens
<220> FEATURE:
<223> OTHER INFORMATION: hmft-1272-f

<400> SEQUENCE: 43

actgagtcct gccggtggcc cgagcccggt ggcctcccgg cgaccctcag cgcgaggcga     60

catggcaggc ggccacagcc tcctgctgga gaacgcgcag caagtggtgt tggtgtgcgc    120

ccgcggcgag cgcttcctgg cgcgggatgc gctgcgcagc ctggcggtgc tggaaggcgc    180

cagcctggtg gtgggcaaag atggatttat aaaagctatt ggtcctgctg atgttattca    240

aagacagttt tctggagaaa cttttgaaga aataattgac tgctctggga aatgtatcct    300

accaggtttg gtggatgcac acacacatcc agtatgggct ggtgaaagag ttcacgaatt    360

tgcaatgaag ttggcaggag ccacctacat ggaaattcac caggccggag gagggatcca    420

ctttaccgtg gagcgcacgc gccaagccac agaggaggag ctgttccgct ccttgcagca    480

acggctccag tgcatgatga gggctggcac cacgctggtg gagtgcaaga gtggatatgg    540

cctcgacctg gagaccgagc tcaagatgct gcgcgtgatt gagcgcgccc ggcgagagct    600

ggacatcggc atctcgg                                                   617
```

```
<210> SEQ ID NO 44
<211> LENGTH: 480
<212> TYPE: DNA
<213> ORGANISM: Homo sapiens
<220> FEATURE:
<223> OTHER INFORMATION: hmft-1272-r

<400> SEQUENCE: 44

tgtggccttt tttttttttt ttttttttaa gagcgacagc aaacatttat tgagagctgt     60

aaaatgtgtt tcacccaatt gtaatgtaaa gaatcgaaaa ttttaaaaaa tttccaaaaa    120

aattacatga ttgtagttgg taaaaatgca cccatttcag gaaggcccct gtgcctgtgt    180

ataaatgatg tgtcttgaac gctgctggga agctctattg ctgagattga gaagacctta    240

gaaacggaag gacactcttc atcagaggac attaattcat ttgacaagca tctagaaaat    300

gaactacttg gggaaaggaa atactatttg cttaacagaa ggctatattt tagcttcatt    360

ggggcgtatc acttagattt ctttcgatcc ctcaatgttc actaaatata gtttaaaaac    420
```

tgagatgtga aatacagaca caaaatggaa attttaagcc aagcctactt ttccccacaa 480

<210> SEQ ID NO 45
<211> LENGTH: 2209
<212> TYPE: DNA
<213> ORGANISM: Homo sapiens
<220> FEATURE:
<223> OTHER INFORMATION: hmft-1488

<400> SEQUENCE: 45
taggcctgta cggaagtgtt acttctgctc taaaagctgc ggaattcctc gagcactgtt 60
ggcctactgg ctgggcctct ctgtgtttgg ttccaagcac ttcccacctc aaactcccat 120
tttcaaacca ctgtatctct gcgcacatct gctacttacc agccgcatac atgatggagg 180 gtttttggt cctgatccag tggccacacc tgtctttgaa atgtctcact gaactccagt 240
tttaaaatag attcattgct tcaacacagc aagcccaatg cacccagcta agactggctt 300
gaccgacagc ctggcctttg gtggggggct tcctggggcc tggggaaagc tggccacctt 360
caacagctgg tacctcttca acagtgtggc ctttcaaaat gcagatgcca ccaggagaac 420
atgcccacag ctcaccacct atggatgcca tggctctggg cagctttcaa agcaggttcc 480
tgtggtctcc tcagctgttt gagggggtaa cagcaaatca gcctccattt taaaatgaaa 540
acaccagcct ccagatgtag ggcctgctgg gtgttgctag ccgctggtcc ccaggcacgg 600
tgcactttct ccacctcctg cagcctccct gttgtttcta gactcttgca cctggtgagt 660
gcaaggatag gtgacccagg ggcctgcagc cttgtcctca gctcccatct cctggactgc 720
cagcctcacc ctctgcagtt agcatggttg gcctgatgca gggatcccga gggattactt 780
tttagacctt ctttcacatt cagaaaagta gtatagattc aggagaggca agaaaattat 840
gctgtccata gaagtcaccc atgaagactg atgccaccac ctgaaggctc atgattgtta 900
aaaatgtcca cgggaacctc tcgtccacag gaggtttgtc tcaacacttc ccatttttac 960
ggcattggca ttgccaagca tggggaagta tctgctcttc tcatgttaaa agtggcccag 1020
cttttcttaa ctcagtccaa gctgacttgt ttagctgcac tggaatttct taccaaccaa 1080
atatttgcat cgagcaaagg gggctgtgtg cacctcccta atggcagcga tgatggctgc 1140
tgtcattcaa gcccatcttc agacgtcaca gtctggaagt gaaatgtcca caaacatctg 1200
tggcagaaaa ggctatacgg accacccagt tgtgctgcag ctttacagag caaggaaggg 1260
ttgtggcaaa taaatgatta acctgcctcg actgtgctga gggcaacaaa ggccatctca 1320
ccaaaggatt attcgatgcc attaaatcat cccgtgacct tcctgcttcc gagtccatgg 1380
cctttgccca gggcatgtac tcccctgaga ggccttctgc ctagaaagat ctatgactgg 1440
gttccaaagt tgaggcctag gtttttgctg ggatttagat attttcaggc accattttga 1500
cagcattcag gaaaacggtt attgacccca tagactaggg taagaataaa ggcaataaat 1560
ttggtctgac tcagaatata ggagatccat atatttctct ggaaaccaca gtgtacacta 1620
aaatgtgaaa ttgaaggttt tgttaaaaag aaaaagataa tgagcttcat gctttgttta 1680
attacataat gatttccatt acgctatttc tgtgaaatgc agcaggttct taaacgttat 1740
ttcagtggca tgggctggaa gcttatcaca aaaagccatg tgtgtggcct tatcagaaca 1800
gaaagagaca ggctggtgcc caaggctgct gcctgctcca ccttttgcca gctctggaca 1860
tctgaggacg tcccggcaga tctggaatgg ggccctcaac tgaccatttg cttctcagaa 1920
tttcagtttg agacatgaga ggtataatca gttacttttc tccccccaga gaaacccttt 1980
tgtgagggga gaggagctat ggtatgtggt tcagctgaaa cacatacaac tgcatccttt 2040

-continued

```
tggagtcctt tgccaacaaa aacagaccaa cagaccagat ggtgtccatg ttcaatatca   2100

tgtcttgatg gacgcagctg atgacctcaa atacttgagt ggtctcatgg ctgttagatg   2160

gattatttga aaaaaaaaaa aaaaaaggcc acatgtgctc gagctgcag               2209
```

```
<210> SEQ ID NO 46
<211> LENGTH: 1741
<212> TYPE: DNA
<213> ORGANISM: Homo sapiens
<220> FEATURE:
<223> OTHER INFORMATION: hmft-1638

<400> SEQUENCE: 46

taggcctgta cggaagtgtt acttctgctc taaaagctgc ggaattcctc gagcactgtt     60

ggcctactgg agcgcggccc ctgggttcga acacggcacc cgcactgcgc gtcatggtgc    120

aggcctggta tatggacgac gccccgggcg acccgcggca accccaccgc cccgaccccg    180

gccgcccagt gggcctggag cagctgcggc ggctcggggt gctctactgg aagctggatg    240

ctgacaaata tgagaatgat ccagaattag aaaagatccg aagagagagg aactactcct    300

ggatggacat cataaccata tgcaaagata aactaccaaa ttatgaagaa aagattaaga    360

tgttctacga ggagcatttg cacttggacg atgagatccg ctacatcctg gatggcagtg    420

ggtacttcga cgtgagggac aaggaggacc agtggatccg gatcttcatg gagaagggag    480

acatggtgac gctccccgcg gggatctatc accgcttcac ggtggacgag aagaactaca    540

cgaaggccat gcggctgttt gtgggagaac cggtgtggac agcgtacaac cggcccgctg    600

accatttga agcccgcggg cagtacgtga aatttctggc acagaccgcc tagcagtgct    660

gcctgggaac taacacgtgc ctcgtaaagg tccccaatgt aatgactgag cagaaaatca    720

atcactttct ctttgctttt agaggatagc cttgaggcta gattatcttt cctttgtaag    780

attatttgat cagaatattt tgtaatgaaa ggatctagaa agcaacttgg aagtgtaaag    840

agtcaccttc attttctgta actcaatcaa gactggtggg tccatggccc tgtgttagtt    900

catgcattca gttgagtccc aaatgaaagt ttcatctccc gaaatgcagt tccttagatg    960

cccatctgga cgtgatgccg cgcctgccgt gtaagaaggt gcaatcctag ataacacagc   1020

tagccagata gaagacactt ttttctccaa aatgatgcct tggggtgggg agtggtagtg   1080

ggaagagctc ccaccctaag ggcacacac tgagttgctt atgccacttc cttgttcaaa   1140

ataaagtaac tgccttaatc ttatactcat ggcttggagt taccttatat tcaggtatat   1200

gtgatatttt gcctggtttg ttaaaattgc cccatttaga ttccttctat aattgttctt   1260

atagataagt aatttatata tgagctgtgt tagtattttt tcagtgtgag atctctggat   1320

tctttcacaa taaagctgtt gaattttaac aggagtatta gtacataaat tttctactca   1380

acaattccga gataggatta tgcctagttt gtcatatcac agaaaaactc caagttaact   1440

tcatgttttg gaagggcagg tcgtttttaa agtatttctt tttttaactg gatgaaaaat   1500

cttcatgtta ggattaattt tcttaatcac ctccacactg tacagaggaa actcaagcct   1560

taaatgttta agtaaactct gtctcagttt taggattaaa atacccaccg gtggtgtgat   1620

gatgccatat accgcagggc ttgcttctgt caagtgtgac tctatctcag taattaaaat   1680

aagtgctgat ctactgaaaa aaaaaaaaaa aaaaaaaagg ccacatgtgc tcgagctgca   1740

g                                                                   1741

<210> SEQ ID NO 47
```

<211> LENGTH: 2323
<212> TYPE: DNA
<213> ORGANISM: Homo sapiens
<220> FEATURE:
<223> OTHER INFORMATION: hmft-1716

<400> SEQUENCE: 47

```
taggcctgta cggaagtgtt acttctgctc taaaagctgc ggaattcctc gagcactgtt     60

ggcctactgg agtgctcatg gggcatggag gagaaggcgg cggccagcgc cagctgccgg    120

gagccgccgg gccccccgag ggccgccgcc gtcgcgtact tcggcatttc cgtggacccg    180

gacgacatcc ttcccggggc cctgcgcctc atccaggagc tgcggccgca ttggaaaccc    240

gagcaagttc ggaccaagcg cttcacggat ggcatcacca acaagctggt ggcctgctat    300

gtggaggagg acatgcagga ctgcgtgctg gtccgggtgt atggggagcg gacggagctg    360

ctggtggacc gggagaatga ggtcagaaac ttccagctgc tgcgagcaca cagctgtgcc    420

cccaaactct actgcacctt ccagaatggg ctgtgctatg agtacatgca gggtgtggcc    480

ctggagcctg agcacatccg tgagccccgg cttttcaggt taatcgcctt agaaatggca    540

aagattcata ctatccacgc caacggcagc ctgcccaagc ccatcctctg gcacaagatg    600

cacaattatt tcacgcttgt gaagaacgag atcaacccca gcctttctgc agatgtccct    660

aaggtagagg tgttggaaca ggagctggcc tggctgaagg agcatctgtc ccagctggag    720

tcccctgtgg tgttttgtca caatgacctg ctctgcaaga atatcatcta tgacagcatc    780

aaaggtcacg tgcggttcat tgactatgaa tatgctggct acaactacca agcttttgac    840

attggcaacc atttcaatga gtttgcaggc gtgaatgagg tggattactg cctgtacccg    900

gcgcgggaga cccagctgca gtggctgcac tactacctgc aggcacaaaa ggggatggcc    960

gtgaccccca gggaggtgca aaggctctac gtgcaagtca acaagtttgc cctggcgtct   1020

cacttcttct gggctctctg ggccctcatc cagaaccagt actccaccat cgactttgat   1080

ttcctcaggt acgcagtgat ccgattcaac cagtacttca aggtgaagcc tcaagcgtca   1140

gccttggaga tgccaaagtg accagccacc ccatccctcc cctacccatc tgtctggcca   1200

gacctgttct ccagagctca attctgcact ctgggatcca cacccttgga cagggtggga   1260

gaggggacac atgggtgtcc agggagaagg ctctgtccct gccgccagac cccagtggtt   1320

gccactgaag acctcattct cctgtctgga ggggctgata ggaccccctt ccgggggtcc   1380

ccttcacccc accaggcttg ggaggaagtg cctgcagcca ggtcctgaac cataaccacc   1440

cctgggaaac acatcattcc cagcctcagg ccctgctgga attggggctg ccttatatgt   1500

gtgtttaccc cttcctggcc tggggaagga ggcggggagg gctcctttct acctccagtg   1560

ccctgagcct ccagtccgtc tccccctgca tgccccatgt gggaggtgct gagctccaaa   1620

ccagcatcac accaactctg acacatggat gtacctatct tggtgatggg tgggggccaa   1680

gaattgagca tgacatcttc cccagcagcc acctcctctg agatccctca ccttctccaa   1740

accagatcca atcaaacctc agcccgagga aacatgctcc ccaacgtgct ctcctgtgct   1800

tctgttttgt ccccctgctg gggggacagg agagggagtg gtgaggccct gggcctccag   1860

agcctggctc tgctttgtgc tgtggcttag ccggagggga cgtggccaag ggtgaggtgg   1920

ccaaaaccag aaccagcagt ctcctgcctt gttccctccc tggccctcag gccctccttc   1980

cagggatgtc tctccagctc tactttatgt cctgaagctg acccgaggtc ttcctatctg   2040

gaatgactag agggagccaa gaggatgggg tgggggccag ggccccccag ggcctatcgt   2100

gggagagcct gggcaggatc ccatcagaaa ggtgctgact aaactggttg cccggacact   2160
```

```
caacagcctc cacctccctt tctaccctca cagctcctgg ggccttcctg gctctggccc   2220

agaaagtgat tcatttgtaa attatcatgg ttttctttct gcattaaaat gctcatttcc   2280

ggaaaaaaaa aaaaaaaaaa ggccacatgt gctcgagctg cag                     2323


<210> SEQ ID NO 48
<211> LENGTH: 1905
<212> TYPE: DNA
<213> ORGANISM: Homo sapiens
<220> FEATURE:
<223> OTHER INFORMATION: hmft-1766

<400> SEQUENCE: 48

taggcctgta cggaagtgtt acttctgctc taaaagctgc ggaattcctc gagcactgtt     60

ggcctactgg agaagcaaaa gagcagagct accatgtcct cttggagcag acagcgacca    120

aaaagcccag ggggcattca accccatgtt tctagaactc tgttcctgct gctgctgttg    180

gcagcctcag cctggggggt caccctgagc cccaaagact gccaggtgtt ccgctcagac    240

catggcagct ccatctcctg tcaaccacct gccgaaatcc ccggctacct gccagccgac    300

accgtgcacc tggccgtgga attcttcaac ctgacccacc tgccagccaa cctcctccag    360

ggcgcctcta agctccaaga attgcacctc tccagcaatg ggctggaaag cctctcgccc    420

gaattcctgc ggccagtgcc gcagctgagg gtgctggatc taacccgaaa cgccctgacc    480

gggctgccct cgggcctctt ccaggcctca gccaccctgg acaccctggt attgaaagaa    540

aaccagctgg aggtcctgga ggtctcgtgg ctacacggcc tgaaagctct ggggcatctg    600

gacctgtctg ggaaccgcct ccggaaactg ccccccgggc tgctggccaa cttcaccctc    660

ctgcgcaccc ttgaccttgg ggagaaccag ttggagacct tgccacctga cctcctgagg    720

ggtccgctgc aattagaacg gctacatcta gaaggcaaca aattgcaagt actgggaaaa    780

gatctcctct tgccgcagcc ggacctgcgc tacctcttcc tgaacggcaa caagctggcc    840

agggtggcag ccggtgcctt ccagggcctg cggcagctgg acatgctgga cctctccaat    900

aactcactgg ccagcgtgcc cgaggggctc tgggcatccc tagggcagcc aaactgggac    960

atgcgggatg gcttcgacat ctccggcaac ccctggatct gtgaccagaa cctgagcgac   1020

ctctatcgtt ggcttcaggc ccaaaaagac aagatgtttt cccagaatga cacgcgctgt   1080

gctgggcctg aagccgtgaa gggccagacg ctcctggcag tggccaagtc ccagtgagac   1140

caggggcttg ggttgagggt ggggggtctg gtagaacact gcaacccgct taacaaataa   1200

tcctgccttt ggccgggtgc gggggctcac gcctgtaatc ccagcacttt gggaggccca   1260

ggtgggcgga tcacgaggtc aggagatcga gaccatcttg gctaacatgg tgaaaccctg   1320

tctctactaa aaatataaaa aattagccag gcgtggtggt gggcacctgt agtcccagca   1380

actcgggagg ctgaggcagg agaatggcgt gaacttggga ggcggagctt gcggtgagcc   1440

aagatcgtgc cactgcactc tagcctgggc gacagagcaa gactgtctca aaaaaattaa   1500

aattaaaatt aaaaacaaat aatcctgcct tttacaggtg aaactcgggg ctgtccatag   1560

cggctgggac cccgtttcat ccatccatgc ttcctagaac acacgatggg ctttccttac   1620

ccatgcccaa ggtgtgccct ccgtctggaa tgccgttccc tgtttcccag atctcttgaa   1680

ctctgggttc tcccagcccc ttgtccttcc ttccagctga gccctggcca cactggggct   1740

gcctttctct gactctgtct tccccaagtc agggggctct ctgagtgcag ggtctgatgc   1800

tgagtcccac ttagcttggg gtcagaacca aggggtttaa taaataaccc ttgaaaactg   1860
```

-continued

```
gaaaaaaaaa aaaaaaaaaa aaggccacat gtgctcgagc tgcag                1905


<210> SEQ ID NO 49
<211> LENGTH: 582
<212> TYPE: DNA
<213> ORGANISM: Homo sapiens
<220> FEATURE:
<223> OTHER INFORMATION: hmft-2263-f

<400> SEQUENCE: 49

tggatgttga tgatggccta gcagctgttg gttactccaa agctgatatc cccgcactag     60

tgaaaggaac gctgccccag gaaagggtca ccaagcttgc accccgtccc cagtcagaag    120

aggatctggc tgctctgttt gaagcttcaa tgaaactgta ttaattgtca ttttaactga    180

aagaattacc gctggccatt gtactgctga gagcaagagc tgatctagct agggctttgt    240

cttttcatct ttgtgcataa cttacctgtt accagtatag gtgggatata catttatctt    300

gcaggaaatt ccccaaagct cagagtccag ttccttccat aaaacaggct ggacaaatga    360

ccactatgtt agacccccag gctcgacttc aggggtcagt gttcctgtcc caaaccccac    420

acagaatact ctgcctctgc ttcatgtagc aaatgagcaa aaactcagta tctatcaaaa    480

gtgtaaatta tatttcctat gcctagtaat tcacttcatg tctaaaaatt tatctgatag    540

aaacactagc accagtacat acagaagcat ggcaaggatg tt                       582


<210> SEQ ID NO 50
<211> LENGTH: 423
<212> TYPE: DNA
<213> ORGANISM: Homo sapiens
<220> FEATURE:
<223> OTHER INFORMATION: hmft-2263-r

<400> SEQUENCE: 50

tgtggccttt tttttttttt tttttttttt tttgtttcaa atcttttatt attagaaaag     60

tgctgccaga aacatccttg ccatgcttct gtatgtactg gtgctagtgt ttctatcaga    120

taaattttta gacatgaagt gaattactag gcataggaaa tataatttac acttttgata    180

gatactgagt tttgctcat ttgctacatg aagcagaggc agagtattct gtgtggggtt    240

tgggacagga acactgaccc ctgaagtcga gcctgggggt ctaacatagt ggtcatttgt    300

ccagcctgtt ttatggaagg aactggactc tgagctttgg ggaatttcct gcaagataaa    360

tgtatatccc acctatactg gtaacaggta agttatgcac aaagatgaaa agacaaagcc    420

cta                                                                  423


<210> SEQ ID NO 51
<211> LENGTH: 618
<212> TYPE: DNA
<213> ORGANISM: Homo sapiens
<220> FEATURE:
<223> OTHER INFORMATION: hmft-2489-f

<400> SEQUENCE: 51

attttacccg acccgacgcc ggcgtgatgt ggcttccgct ggtgctgctc ctggctgtgc     60

tgctgctggc cgtcctctgc aaagtttact tgggactatt ctctggcagc tccccgaatc    120

ctttctccga agatgtcaaa cggcccccag cgcccctggt aactgacaag gaggccagga    180

agaaggttct caaacaagct ttttcagcca accaagtgcc ggagaagctg gatgtggtgg    240

taattggcag tggctttggg ggcctggctg cagctgcaat tctagctaaa gctggcaagc    300

gagtcctggt gctggaacaa cataccaagg caggggggctg ctgtcatacc tttggaaaga    360
```

atggccttga atttgacaca ggaatccatt acattgggcg tatggaagag ggcagcattg 420
gccgttttat cttggaccag atcactgaag ggcagctgga ctgggctccc ctgtcctctc 480
cttttgacat catggtactg gaagggccca atggccgaaa ggagtacccc atgtacagtg 540
gagagaaagc ctacattcag ggcctcaagg agaagtttcc acaggaggaa gctatcattg 600
acaagtatat aaagctgg 618

<210> SEQ ID NO 52
<211> LENGTH: 586
<212> TYPE: DNA
<213> ORGANISM: Homo sapiens
<220> FEATURE:
<223> OTHER INFORMATION: hmft-2489-r

<400> SEQUENCE: 52
tgtggccttt tttttttttt tttttaacat ttggagatat tttatttctg tgataaggaa 60
atctcacata aaagtcttta tcatttcatt aattcacaaa aagtgttaaa tcagttaaaa 120
ttaaagagaa aagttcacac cgaatgaaag actcgttttg tcttctcttc ccctgaagta 180
atttaaactc ccaaagcagc acgagttttt gaaatcagtt tttgtccctc ttcagcaaag 240
cagacttcct gttcctggcc ttggcagcat ttctccaaca ggcctgagaa atctgcaatg 300
acagcctcaa gttgttcctc tgttatttgt ggcttttgct tcacaaggtt aatgagaaac 360
tcttgcttca tcgtttgcag cgctacaccc tgagcttggc acagatcctt atggaaaatg 420
aacttgtcat cagagaatgc aggagggaca tatgtttcat ccaccaccaa gctgctgaag 480
catggcctcc tgttggcata tgaagaagtg cagcactggc caacaccagg gtttactgga 540
gtcatttcat gtctgataca taagtgtccg ataataatgt cagccg 586

<210> SEQ ID NO 53
<211> LENGTH: 472
<212> TYPE: DNA
<213> ORGANISM: Homo sapiens
<220> FEATURE:
<223> OTHER INFORMATION: hyst-0269-f

<400> SEQUENCE: 53
atgacttgga tcaaacagcc taaatgggaa gaaggacatt tttgctgcat caaggaagcc 60
gttaaactcc tgctaagcta actagctctt ttttatgggt ccatgcacac gaccgaactc 120
ctctttcact gaccagagat tatttctgac aacccaggat atcccgaaag cttggaggca 180
tatggctgga aaatgaaacg acccaggaca tcgtttctgg ctgcatcatt attttgtgtc 240
gcgtagtacc agatgggcag tcagtgagcg gcgcagggat gtgaacggac ggttttataa 300
tgtgaaaatt ttcccttggt aaagctaaaa cagatttaat ttccctctct tttctttcac 360
tacttccccc tctttattcc ccctctgtct gcaatatcag tgaactcaac tttgcagtga 420
ggtggccaaa aagagagaga atgaggagat cttgatcatc ttagtgtcgg ag 472

<210> SEQ ID NO 54
<211> LENGTH: 584
<212> TYPE: DNA
<213> ORGANISM: Homo sapiens
<220> FEATURE:
<223> OTHER INFORMATION: hyst-0269-r

<400> SEQUENCE: 54
tgtggccttt tttttttttt ttttatgttt caacaagatt tatttattag attaagtgaa 60

-continued

```
tatattaaca ttccatgggt aaaattacag aagacatggt taggaataaa atttcctcat    120

ctccttgatg tcttcgtccc tcatattaag tccttaattt gcagagttag caacattctt    180

aattccttgt acaagaaatt ttcttgtgga aaatagtttt acctgttagt ctccacacgt    240

atgtctgatc tttgtgatac ggtatcaggc atcccctgac ctgttggttt gtcatctttt    300

ccatttatc ttttcatcta ttttgcaaac tcatcaagat gacttccact ttccagcttc    360

tccattatgt acctaagggt tgtccttaaa tttttgtcca acctaaaaaa taacaatcac    420

taaatgatag aactctataa taactaaacg atagaatgat agaaataatt tccagcattc    480

ctgtcggagt gatagaaatc tcctagccta ctttgaagca aatcaaaagc aactgtgaag    540

ttaatttaat gaaattattt tctctttttg aggcccactg ttgc                     584
```

<210> SEQ ID NO 55
<211> LENGTH: 461
<212> TYPE: DNA
<213> ORGANISM: Homo sapiens
<220> FEATURE:
<223> OTHER INFORMATION: hyst-0281-f

<400> SEQUENCE: 55

```
ctgggagctg ccgccagggc caggagggga gcggcacctg gaagatgcgc ccattggctg     60

gtggcctgct caaggtggtg ttcgtggtct tcgcctcctt gtgtgcctgg tattcggggt    120

acctgctcgc agagctcatt ccagatgcac ccctgtccag tgctgcctat agcatccgca    180

gcatcgggga gaggcctgtc ctcaaagctc cagtccccaa aaggcaaaaa tgtgaccact    240

ggactccctg cccatctgac acctatgcct acaggttact cagcggaggt ggcagaagca    300

agtacgccaa aatctgcttt gaggataacc tacttatggg agaacagctg ggaaatgttg    360

ccagaggaat aaacattgcc attgtcaact atgtaactgg gaatgtgaca gcaacacgat    420

gttttgatat gtatgaaggc gataactctg gaccgatgac a                        461
```

<210> SEQ ID NO 56
<211> LENGTH: 571
<212> TYPE: DNA
<213> ORGANISM: Homo sapiens
<220> FEATURE:
<223> OTHER INFORMATION: hyst-0281-r

<400> SEQUENCE: 56

```
tgtggccttt tttttttttt tttttgatac aactagcaaa tgttcattgg tttacaacaa     60

acccaaaata ctcatcaaat atgggctgtt ggatttagaa aaataagatt cttgagcgat    120

tccagctgca tttgtttata cagaacacat ttactcagga ccctgcagtg tcagcttcgt    180

tctttgggta tgcagccttc tatctggatc tctgcaggcc agccagaata tctgttgttc    240

ttagcatcag agtggttgat cttttctctc tgaatttcgg aagggagttc caagcctttt    300

gctgcaataa atacccagct agacctgaat ttcatgttcc tgatttcttt acttccaagt    360

gcttctatgg cattcttggc atcgttattc agtcttgtgc ttccgtcgtc ataggtcacc    420

atgaagagca gggattttgg agcagcactc tgaataaact ttgtcatcgg tccagagtta    480

tcgccttcat acatatcaaa acatcgtgtt gctgtcacat tcccagttac atagttgaca    540

atggcaatgt ttattcctct ggcaacattt c                                   571
```

<210> SEQ ID NO 57
<211> LENGTH: 431
<212> TYPE: DNA
<213> ORGANISM: Homo sapiens -continued
<220> FEATURE:
<223> OTHER INFORMATION: hyst-1031-f

<400> SEQUENCE: 57
gtcttgcatt actattgtgc ggctgcagga ggtgtcgagc ggcgttattt ttttttgcgg 60
tttgcctttt ttttcttttt ttttttttgg aaccgcggtt gtttaaaagc ctgagggaac 120
ctggaggggg gctcccactc tctaccttct ttcctccgag tttgtgactc cgagatggac 180
aaagtgtgtg ctgtttttgg aggctcccga ggcattggca gagctgtggc ccagttaatg 240
gcccggaaag gctaccgact ggcggtcatt gccagaaacc tggaaggggc caaagccgcc 300
gccggtgacc tcggcggtag gtaccaaact ggagttgtcc agttgtatgg ccgcggtcca 360
ggcgcctaaa gaaaatctcc tttgtaaaaa gagcgggtct ggcctttagg gctctagggt 420
tactcgatgt a 431

<210> SEQ ID NO 58
<211> LENGTH: 594
<212> TYPE: DNA
<213> ORGANISM: Homo sapiens
<220> FEATURE:
<223> OTHER INFORMATION: hyst-1031-r
<220> FEATURE:
<221> NAME/KEY: modified_base
<222> LOCATION: (54)..(54)
<223> OTHER INFORMATION: a, t, c, g, unknown or other
<220> FEATURE:
<221> NAME/KEY: modified_base
<222> LOCATION: (122)..(122)
<223> OTHER INFORMATION: a, t, c, g, unknown or other
<220> FEATURE:
<221> NAME/KEY: modified_base
<222> LOCATION: (129)..(129)
<223> OTHER INFORMATION: a, t, c, g, unknown or other
<220> FEATURE:
<221> NAME/KEY: modified_base
<222> LOCATION: (139)..(139)
<223> OTHER INFORMATION: a, t, c, g, unknown or other
<220> FEATURE:
<221> NAME/KEY: modified_base
<222> LOCATION: (141)..(141)
<223> OTHER INFORMATION: a, t, c, g, unknown or other
<220> FEATURE:
<221> NAME/KEY: modified_base
<222> LOCATION: (161)..(161)
<223> OTHER INFORMATION: a, t, c, g, unknown or other
<220> FEATURE:
<221> NAME/KEY: modified_base
<222> LOCATION: (212)..(212)
<223> OTHER INFORMATION: a, t, c, g, unknown or other
<220> FEATURE:
<221> NAME/KEY: modified_base
<222> LOCATION: (233)..(233)
<223> OTHER INFORMATION: a, t, c, g, unknown or other
<220> FEATURE:
<221> NAME/KEY: modified_base
<222> LOCATION: (239)..(239)
<223> OTHER INFORMATION: a, t, c, g, unknown or other
<220> FEATURE:
<221> NAME/KEY: modified_base
<222> LOCATION: (266)..(266)
<223> OTHER INFORMATION: a, t, c, g, unknown or other
<220> FEATURE:
<221> NAME/KEY: modified_base
<222> LOCATION: (272)..(272)
<223> OTHER INFORMATION: a, t, c, g, unknown or other
<220> FEATURE:
<221> NAME/KEY: modified_base
<222> LOCATION: (284)..(284)
<223> OTHER INFORMATION: a, t, c, g, unknown or other
<220> FEATURE:
<221> NAME/KEY: modified_base
<222> LOCATION: (288)..(288)

<223> OTHER INFORMATION: a, t, c, g, unknown or other
<220> FEATURE:
<221> NAME/KEY: modified_base
<222> LOCATION: (305)..(305)
<223> OTHER INFORMATION: a, t, c, g, unknown or other
<220> FEATURE:
<221> NAME/KEY: modified_base
<222> LOCATION: (333)..(333)
<223> OTHER INFORMATION: a, t, c, g, unknown or other
<220> FEATURE:
<221> NAME/KEY: modified_base
<222> LOCATION: (342)..(342)
<223> OTHER INFORMATION: a, t, c, g, unknown or other
<220> FEATURE:
<221> NAME/KEY: modified_base
<222> LOCATION: (347)..(347)
<223> OTHER INFORMATION: a, t, c, g, unknown or other
<220> FEATURE:
<221> NAME/KEY: modified_base
<222> LOCATION: (356)..(356)
<223> OTHER INFORMATION: a, t, c, g, unknown or other
<220> FEATURE:
<221> NAME/KEY: modified_base
<222> LOCATION: (368)..(368)
<223> OTHER INFORMATION: a, t, c, g, unknown or other
<220> FEATURE:
<221> NAME/KEY: modified_base
<222> LOCATION: (373)..(373)
<223> OTHER INFORMATION: a, t, c, g, unknown or other
<220> FEATURE:
<221> NAME/KEY: modified_base
<222> LOCATION: (376)..(376)
<223> OTHER INFORMATION: a, t, c, g, unknown or other
<220> FEATURE:
<221> NAME/KEY: modified_base
<222> LOCATION: (412)..(412)
<223> OTHER INFORMATION: a, t, c, g, unknown or other
<220> FEATURE:
<221> NAME/KEY: modified_base
<222> LOCATION: (435)..(435)
<223> OTHER INFORMATION: a, t, c, g, unknown or other
<220> FEATURE:
<221> NAME/KEY: modified_base
<222> LOCATION: (437)..(437)
<223> OTHER INFORMATION: a, t, c, g, unknown or other
<220> FEATURE:
<221> NAME/KEY: modified_base
<222> LOCATION: (464)..(464)
<223> OTHER INFORMATION: a, t, c, g, unknown or other
<220> FEATURE:
<221> NAME/KEY: modified_base
<222> LOCATION: (495)..(495)
<223> OTHER INFORMATION: a, t, c, g, unknown or other
<220> FEATURE:
<221> NAME/KEY: modified_base
<222> LOCATION: (522)..(522)
<223> OTHER INFORMATION: a, t, c, g, unknown or other
<220> FEATURE:
<221> NAME/KEY: modified_base
<222> LOCATION: (559)..(559)
<223> OTHER INFORMATION: a, t, c, g, unknown or other
<220> FEATURE:
<221> NAME/KEY: modified_base
<222> LOCATION: (574)..(574)
<223> OTHER INFORMATION: a, t, c, g, unknown or other

<400> SEQUENCE: 58
tgtggccttt tttttttttt tttttttttt tttttttttt tttttttttc tttngagcac 60 atattttat aaagacagaa attaacattt gtagcatcag caggtttgat tagcacatgt 120
tncccatgna ggtataatng nctaatcagt agccaaaggg ngcccttgat gctaatcacc 180
cctataactg aataatctgc aaattacaaa angagttgta atcccccatc cantaccana 240
acatgccctg taatatacgg ggattntaaa anaaacacaa ccgnatgngc cacctcaata 300
gtttntccaa acctcccaag aggaatattt ttntttaaag gntcttnttt caagtntttc 360

```
gtcatatntg ggngtncaaa tcctttgaag cctttgcagt tccagtccca anattacact    420

catatacttg caaangngca aaataaactc catacaagta ttgncactgg ggcaactaca    480

ttcactctaa ttttntttct tgctacctct ttagcaagag cncgtgaaaa tccaactaat    540

cctcctttac tggcactgna aacggactgg ccanagttgc cttttaagcc aaca          594
```

<210> SEQ ID NO 59
<211> LENGTH: 2117
<212> TYPE: DNA
<213> ORGANISM: Homo sapiens
<220> FEATURE:
<223> OTHER INFORMATION: hyst-1046

<400> SEQUENCE: 59

```
ttctaggcct gtacggaagt gttacttctg ctctaaaagc tgcggaattc ctcgagcact     60

gttggcctac tgggtgctct cttccaaggc tgtaggagtt ctggagctgc tggctggaga    120

ggagggtgga cgaagctctc tccagaaaga catcctgaga ggacttggca gcctgcagat    180

ggcctattgt gggaccttgt gatcatgcct gaacatgcat tggctgcgaa aagttcaggg    240

actttgcacc ctgtggggta ctcagatgtc cagccgcact ctctacatta atagtaggca    300

actggtgtcc ctgcagtggg gccaccagga agttccggcc aagtttaact ttgctagtga    360

tgtgttggat cactgggctg acatggagaa ggctggcaag cgactcccaa gcccagccct    420

gtggtgggtg aatgggaagg ggaaggaatt aatgtggaat ttcagagaac tgagtgaaaa    480

cagccagcag gcagccaacg tcctctcggg agcctgtggc ctgcagcgtg ggatcgtgt     540

ggcagtgatg ctgccccgag tgcctgagtg gtggctggtg atcctgggct gcattcgagc    600

aggtctcatc tttatgcctg gaaccatcca gatgaaatcc actgacatac tgtataggtt    660

gcagatgtct aaggccaagg ctattgttgc tggggatgaa gtcatccaag aagtggacac    720

agtggcatct gaatgtcctt ctctgagaat taagctactg gtgtctgaga aaagctgcga    780

tgggtggctg aacttcaaga aactactaaa tgaggcatcc accactcatc actgtgtgga    840

gactggaagc caggaagcat ctgccatcta cttcactagt gggaccagtg gtcttcccaa    900

gatggcagaa cattcctact cgagcctggg cctcaaggcc aagatggatg ctggttggac    960

aggcctgcaa gcctctgata taatgtggac catatcagac acaggttgga tactgaacat   1020

cttgggctca cttttggaat cttggacatt aggagcatgc acatttgttc atctcttgcc   1080

aaagtttgac ccactggtta ttctaaagac actctccagt tatccaatca agagtatgat   1140

gggtgcccct attgtttacc ggatgttgct acagcaggat ctttccagtt acaagttccc   1200

ccatctacag aactgcctcg ctggagggga gtcccttctt ccagaaactc tggagaactg   1260

gagggcccag acaggactgg acatccgaga attctatggc cagacagaaa cgggattaac   1320

ttgcatggtt tccaagacaa tgaaaatcaa accaggatac atgggaacgg ctgcttcctg   1380

ttatgatgta caggttatag atgataaggg caacgtcctg ccccccggca cagaaggaga   1440

cattggcatc agggtcaaac ccatcaggcc tataggcatc ttctctggct atgtggaaaa   1500

tcccgacaag acagcagcca acattcgagg agacttttgg ctccttggag accggggaat   1560

caaagatgaa gatgggtatt tccagtttat gggacgggca gatgatatca ttaactccag   1620

cgggtaccgg attggaccct cggaggtaga gaatgcactg atgaagcacc ctgctgtggt   1680

tgagacggct gtgatcagca gcccagaccc cgtccgagga gaggtggtga aggcatttgt   1740

gatcctggcc tcgcagttcc tatcccatga cccagaacag ctcaccaagg agctgcagca   1800
```

```
gcatgtgaag tcagtgacag ccccatacaa gtacccaaga aagatagagt ttgtcttgaa   1860

cctgcccaag actgtcacag ggaaaattca acgaaccaaa cttcgagaca aggagtggaa   1920

gatgtccgga aaagcccgtg cgcagtgagg cgtctaggag acattcattt ggattcccct   1980

cttctttctc tttcttttcc ctttgggccc ttggccttac tatgatgata tgagattctt   2040

tatgaaagaa catgaatgta aaaaaaaaaa aaaaaaaagg ccacatgtgc tcgagctgca   2100

ggtcgcggcc gctagac                                                  2117
```

<210> SEQ ID NO 60
<211> LENGTH: 416
<212> TYPE: DNA
<213> ORGANISM: Homo sapiens
<220> FEATURE:
<223> OTHER INFORMATION: hyst-1888-f

<400> SEQUENCE: 60

```
aaggtggaag gaggggccgt gaggtgagag agtccgggag cccgaccttg agatggcctg     60

atatgaagga gtcacgcctc ccgcctcccg gagctgccca gtggctgcct tgtccttcaa    120

gtgcaggagc tggttcaaat gtcaggaatg gaagccactg tgaccatccc aatctggcaa    180

aacaagccac atggggctgc tcgaagtgta gtaagaagaa ttgggaccaa cctacccttg    240

aagccgtgtg cccgggcgtc ctttgagacc ctgcccaaca tctctgacct gtgtttgaga    300

gatgtgcccc cagtccctac cctggctgac atcgactgga ttgctgcgga tgaagaggag    360

acatatgccc gggtcaggag tgatacgcgc cccctgaggc acacctggaa acccag        416
```

<210> SEQ ID NO 61
<211> LENGTH: 686
<212> TYPE: DNA
<213> ORGANISM: Homo sapiens
<220> FEATURE:
<223> OTHER INFORMATION: hyst-1888-r
<220> FEATURE:
<221> NAME/KEY: modified_base
<222> LOCATION: (31)..(33)
<223> OTHER INFORMATION: a, t, c, g, unknown or other
<220> FEATURE:
<221> NAME/KEY: modified_base
<222> LOCATION: (35)..(36)
<223> OTHER INFORMATION: a, t, c, g, unknown or other
<220> FEATURE:
<221> NAME/KEY: modified_base
<222> LOCATION: (49)..(51)
<223> OTHER INFORMATION: a, t, c, g, unknown or other
<220> FEATURE:
<221> NAME/KEY: modified_base
<222> LOCATION: (59)..(59)
<223> OTHER INFORMATION: a, t, c, g, unknown or other
<220> FEATURE:
<221> NAME/KEY: modified_base
<222> LOCATION: (70)..(71)
<223> OTHER INFORMATION: a, t, c, g, unknown or other
<220> FEATURE:
<221> NAME/KEY: modified_base
<222> LOCATION: (73)..(73)
<223> OTHER INFORMATION: a, t, c, g, unknown or other
<220> FEATURE:
<221> NAME/KEY: modified_base
<222> LOCATION: (79)..(79)
<223> OTHER INFORMATION: a, t, c, g, unknown or other
<220> FEATURE:
<221> NAME/KEY: modified_base
<222> LOCATION: (81)..(81)
<223> OTHER INFORMATION: a, t, c, g, unknown or other
<220> FEATURE:
<221> NAME/KEY: modified_base
<222> LOCATION: (86)..(86)
<223> OTHER INFORMATION: a, t, c, g, unknown or other
<220> FEATURE:
<221> NAME/KEY: modified_base
<222> LOCATION: (110)..(110)
<223> OTHER INFORMATION: a, t, c, g, unknown or other
<220> FEATURE:
<221> NAME/KEY: modified_base
<222> LOCATION: (113)..(113)
<223> OTHER INFORMATION: a, t, c, g, unknown or other
<220> FEATURE:
<221> NAME/KEY: modified_base
<222> LOCATION: (144)..(144)
<223> OTHER INFORMATION: a, t, c, g, unknown or other
<220> FEATURE:
<221> NAME/KEY: modified_base
<222> LOCATION: (146)..(146)
<223> OTHER INFORMATION: a, t, c, g, unknown or other
<220> FEATURE:
<221> NAME/KEY: modified_base
<222> LOCATION: (148)..(148)
<223> OTHER INFORMATION: a, t, c, g, unknown or other
<220> FEATURE:
<221> NAME/KEY: modified_base
<222> LOCATION: (150)..(151)
<223> OTHER INFORMATION: a, t, c, g, unknown or other
<220> FEATURE:
<221> NAME/KEY: modified_base
<222> LOCATION: (153)..(155)
<223> OTHER INFORMATION: a, t, c, g, unknown or other
<220> FEATURE:
<221> NAME/KEY: modified_base
<222> LOCATION: (157)..(157)
<223> OTHER INFORMATION: a, t, c, g, unknown or other
<220> FEATURE:
<221> NAME/KEY: modified_base
<222> LOCATION: (170)..(170)
<223> OTHER INFORMATION: a, t, c, g, unknown or other
<220> FEATURE:
<221> NAME/KEY: modified_base
<222> LOCATION: (172)..(173)
<223> OTHER INFORMATION: a, t, c, g, unknown or other
<220> FEATURE:
<221> NAME/KEY: modified_base
<222> LOCATION: (187)..(187)
<223> OTHER INFORMATION: a, t, c, g, unknown or other
<220> FEATURE:
<221> NAME/KEY: modified_base
<222> LOCATION: (192)..(192)
<223> OTHER INFORMATION: a, t, c, g, unknown or other
<220> FEATURE:
<221> NAME/KEY: modified_base
<222> LOCATION: (195)..(195)
<223> OTHER INFORMATION: a, t, c, g, unknown or other
<220> FEATURE:
<221> NAME/KEY: modified_base
<222> LOCATION: (202)..(202)
<223> OTHER INFORMATION: a, t, c, g, unknown or other
<220> FEATURE:
<221> NAME/KEY: modified_base
<222> LOCATION: (211)..(211)
<223> OTHER INFORMATION: a, t, c, g, unknown or other
<220> FEATURE:
<221> NAME/KEY: modified_base
<222> LOCATION: (220)..(220)
<223> OTHER INFORMATION: a, t, c, g, unknown or other
<220> FEATURE:
<221> NAME/KEY: modified_base
<222> LOCATION: (225)..(225)
<223> OTHER INFORMATION: a, t, c, g, unknown or other
<220> FEATURE:
<221> NAME/KEY: modified_base
<222> LOCATION: (227)..(227)
<223> OTHER INFORMATION: a, t, c, g, unknown or other
<220> FEATURE:
<221> NAME/KEY: modified_base
<222> LOCATION: (241)..(243)
<223> OTHER INFORMATION: a, t, c, g, unknown or other
<220> FEATURE:
<221> NAME/KEY: modified_base
<222> LOCATION: (245)..(245)

<223> OTHER INFORMATION: a, t, c, g, unknown or other
<220> FEATURE:
<221> NAME/KEY: modified_base
<222> LOCATION: (254)..(254)
<223> OTHER INFORMATION: a, t, c, g, unknown or other
<220> FEATURE:
<221> NAME/KEY: modified_base
<222> LOCATION: (296)..(296)
<223> OTHER INFORMATION: a, t, c, g, unknown or other
<220> FEATURE:
<221> NAME/KEY: modified_base
<222> LOCATION: (304)..(305)
<223> OTHER INFORMATION: a, t, c, g, unknown or other
<220> FEATURE:
<221> NAME/KEY: modified_base
<222> LOCATION: (314)..(314)
<223> OTHER INFORMATION: a, t, c, g, unknown or other
<220> FEATURE:
<221> NAME/KEY: modified_base
<222> LOCATION: (316)..(316)
<223> OTHER INFORMATION: a, t, c, g, unknown or other
<220> FEATURE:
<221> NAME/KEY: modified_base
<222> LOCATION: (324)..(324)
<223> OTHER INFORMATION: a, t, c, g, unknown or other
<220> FEATURE:
<221> NAME/KEY: modified_base
<222> LOCATION: (326)..(326)
<223> OTHER INFORMATION: a, t, c, g, unknown or other
<220> FEATURE:
<221> NAME/KEY: modified_base
<222> LOCATION: (333)..(333)
<223> OTHER INFORMATION: a, t, c, g, unknown or other
<220> FEATURE:
<221> NAME/KEY: modified_base
<222> LOCATION: (335)..(336)
<223> OTHER INFORMATION: a, t, c, g, unknown or other
<220> FEATURE:
<221> NAME/KEY: modified_base
<222> LOCATION: (346)..(346)
<223> OTHER INFORMATION: a, t, c, g, unknown or other
<220> FEATURE:
<221> NAME/KEY: modified_base
<222> LOCATION: (358)..(358)
<223> OTHER INFORMATION: a, t, c, g, unknown or other
<220> FEATURE:
<221> NAME/KEY: modified_base
<222> LOCATION: (364)..(364)
<223> OTHER INFORMATION: a, t, c, g, unknown or other
<220> FEATURE:
<221> NAME/KEY: modified_base
<222> LOCATION: (373)..(373)
<223> OTHER INFORMATION: a, t, c, g, unknown or other
<220> FEATURE:
<221> NAME/KEY: modified_base
<222> LOCATION: (378)..(378)
<223> OTHER INFORMATION: a, t, c, g, unknown or other
<220> FEATURE:
<221> NAME/KEY: modified_base
<222> LOCATION: (380)..(382)
<223> OTHER INFORMATION: a, t, c, g, unknown or other
<220> FEATURE:
<221> NAME/KEY: modified_base
<222> LOCATION: (387)..(388)
<223> OTHER INFORMATION: a, t, c, g, unknown or other
<220> FEATURE:
<221> NAME/KEY: modified_base
<222> LOCATION: (398)..(399)
<223> OTHER INFORMATION: a, t, c, g, unknown or other
<220> FEATURE:
<221> NAME/KEY: modified_base
<222> LOCATION: (406)..(407)
<223> OTHER INFORMATION: a, t, c, g, unknown or other
<220> FEATURE:
<221> NAME/KEY: modified_base
<222> LOCATION: (410)..(411)
<223> OTHER INFORMATION: a, t, c, g, unknown or other
<220> FEATURE:
<221> NAME/KEY: modified_base -continued
<222> LOCATION: (414)..(414)
<223> OTHER INFORMATION: a, t, c, g, unknown or other
<220> FEATURE:
<221> NAME/KEY: modified_base
<222> LOCATION: (421)..(422)
<223> OTHER INFORMATION: a, t, c, g, unknown or other
<220> FEATURE:
<221> NAME/KEY: modified_base
<222> LOCATION: (424)..(424)
<223> OTHER INFORMATION: a, t, c, g, unknown or other
<220> FEATURE:
<221> NAME/KEY: modified_base
<222> LOCATION: (426)..(426)
<223> OTHER INFORMATION: a, t, c, g, unknown or other
<220> FEATURE:
<221> NAME/KEY: modified_base
<222> LOCATION: (429)..(429)
<223> OTHER INFORMATION: a, t, c, g, unknown or other
<220> FEATURE:
<221> NAME/KEY: modified_base
<222> LOCATION: (433)..(433)
<223> OTHER INFORMATION: a, t, c, g, unknown or other
<220> FEATURE:
<221> NAME/KEY: modified_base
<222> LOCATION: (440)..(440)
<223> OTHER INFORMATION: a, t, c, g, unknown or other
<220> FEATURE:
<221> NAME/KEY: modified_base
<222> LOCATION: (444)..(444)
<223> OTHER INFORMATION: a, t, c, g, unknown or other
<220> FEATURE:
<221> NAME/KEY: modified_base
<222> LOCATION: (448)..(448)
<223> OTHER INFORMATION: a, t, c, g, unknown or other
<220> FEATURE:
<221> NAME/KEY: modified_base
<222> LOCATION: (450)..(451)
<223> OTHER INFORMATION: a, t, c, g, unknown or other
<220> FEATURE:
<221> NAME/KEY: modified_base
<222> LOCATION: (457)..(458)
<223> OTHER INFORMATION: a, t, c, g, unknown or other
<220> FEATURE:
<221> NAME/KEY: modified_base
<222> LOCATION: (461)..(461)
<223> OTHER INFORMATION: a, t, c, g, unknown or other
<220> FEATURE:
<221> NAME/KEY: modified_base
<222> LOCATION: (464)..(465)
<223> OTHER INFORMATION: a, t, c, g, unknown or other
<220> FEATURE:
<221> NAME/KEY: modified_base
<222> LOCATION: (467)..(467)
<223> OTHER INFORMATION: a, t, c, g, unknown or other
<220> FEATURE:
<221> NAME/KEY: modified_base
<222> LOCATION: (471)..(471)
<223> OTHER INFORMATION: a, t, c, g, unknown or other
<220> FEATURE:
<221> NAME/KEY: modified_base
<222> LOCATION: (475)..(475)
<223> OTHER INFORMATION: a, t, c, g, unknown or other
<220> FEATURE:
<221> NAME/KEY: modified_base
<222> LOCATION: (479)..(479)
<223> OTHER INFORMATION: a, t, c, g, unknown or other
<220> FEATURE:
<221> NAME/KEY: modified_base
<222> LOCATION: (484)..(486)
<223> OTHER INFORMATION: a, t, c, g, unknown or other
<220> FEATURE:
<221> NAME/KEY: modified_base
<222> LOCATION: (490)..(490)
<223> OTHER INFORMATION: a, t, c, g, unknown or other
<220> FEATURE:
<221> NAME/KEY: modified_base
<222> LOCATION: (492)..(492)
<223> OTHER INFORMATION: a, t, c, g, unknown or other
<220> FEATURE:

<221> NAME/KEY: modified_base
<222> LOCATION: (499)..(500)
<223> OTHER INFORMATION: a, t, c, g, unknown or other
<220> FEATURE:
<221> NAME/KEY: modified_base
<222> LOCATION: (502)..(502)
<223> OTHER INFORMATION: a, t, c, g, unknown or other
<220> FEATURE:
<221> NAME/KEY: modified_base
<222> LOCATION: (506)..(506)
<223> OTHER INFORMATION: a, t, c, g, unknown or other
<220> FEATURE:
<221> NAME/KEY: modified_base
<222> LOCATION: (511)..(511)
<223> OTHER INFORMATION: a, t, c, g, unknown or other
<220> FEATURE:
<221> NAME/KEY: modified_base
<222> LOCATION: (513)..(513)
<223> OTHER INFORMATION: a, t, c, g, unknown or other
<220> FEATURE:
<221> NAME/KEY: modified_base
<222> LOCATION: (517)..(517)
<223> OTHER INFORMATION: a, t, c, g, unknown or other
<220> FEATURE:
<221> NAME/KEY: modified_base
<222> LOCATION: (519)..(521)
<223> OTHER INFORMATION: a, t, c, g, unknown or other
<220> FEATURE:
<221> NAME/KEY: modified_base
<222> LOCATION: (526)..(526)
<223> OTHER INFORMATION: a, t, c, g, unknown or other
<220> FEATURE:
<221> NAME/KEY: modified_base
<222> LOCATION: (529)..(529)
<223> OTHER INFORMATION: a, t, c, g, unknown or other
<220> FEATURE:
<221> NAME/KEY: modified_base
<222> LOCATION: (531)..(531)
<223> OTHER INFORMATION: a, t, c, g, unknown or other
<220> FEATURE:
<221> NAME/KEY: modified_base
<222> LOCATION: (534)..(537)
<223> OTHER INFORMATION: a, t, c, g, unknown or other
<220> FEATURE:
<221> NAME/KEY: modified_base
<222> LOCATION: (539)..(539)
<223> OTHER INFORMATION: a, t, c, g, unknown or other
<220> FEATURE:
<221> NAME/KEY: modified_base
<222> LOCATION: (541)..(543)
<223> OTHER INFORMATION: a, t, c, g, unknown or other
<220> FEATURE:
<221> NAME/KEY: modified_base
<222> LOCATION: (545)..(546)
<223> OTHER INFORMATION: a, t, c, g, unknown or other
<220> FEATURE:
<221> NAME/KEY: modified_base
<222> LOCATION: (549)..(552)
<223> OTHER INFORMATION: a, t, c, g, unknown or other
<220> FEATURE:
<221> NAME/KEY: modified_base
<222> LOCATION: (554)..(554)
<223> OTHER INFORMATION: a, t, c, g, unknown or other
<220> FEATURE:
<221> NAME/KEY: modified_base
<222> LOCATION: (557)..(557)
<223> OTHER INFORMATION: a, t, c, g, unknown or other
<220> FEATURE:
<221> NAME/KEY: modified_base
<222> LOCATION: (561)..(562)
<223> OTHER INFORMATION: a, t, c, g, unknown or other
<220> FEATURE:
<221> NAME/KEY: modified_base
<222> LOCATION: (567)..(568)
<223> OTHER INFORMATION: a, t, c, g, unknown or other
<220> FEATURE:
<221> NAME/KEY: modified_base
<222> LOCATION: (575)..(575)
<223> OTHER INFORMATION: a, t, c, g, unknown or other
<220> FEATURE:
<221> NAME/KEY: modified_base
<222> LOCATION: (579)..(579)
<223> OTHER INFORMATION: a, t, c, g, unknown or other
<220> FEATURE:
<221> NAME/KEY: modified_base
<222> LOCATION: (582)..(582)
<223> OTHER INFORMATION: a, t, c, g, unknown or other
<220> FEATURE:
<221> NAME/KEY: modified_base
<222> LOCATION: (585)..(585)
<223> OTHER INFORMATION: a, t, c, g, unknown or other
<220> FEATURE:
<221> NAME/KEY: modified_base
<222> LOCATION: (593)..(593)
<223> OTHER INFORMATION: a, t, c, g, unknown or other
<220> FEATURE:
<221> NAME/KEY: modified_base
<222> LOCATION: (601)..(601)
<223> OTHER INFORMATION: a, t, c, g, unknown or other
<220> FEATURE:
<221> NAME/KEY: modified_base
<222> LOCATION: (603)..(603)
<223> OTHER INFORMATION: a, t, c, g, unknown or other
<220> FEATURE:
<221> NAME/KEY: modified_base
<222> LOCATION: (605)..(606)
<223> OTHER INFORMATION: a, t, c, g, unknown or other
<220> FEATURE:
<221> NAME/KEY: modified_base
<222> LOCATION: (608)..(608)
<223> OTHER INFORMATION: a, t, c, g, unknown or other
<220> FEATURE:
<221> NAME/KEY: modified_base
<222> LOCATION: (613)..(614)
<223> OTHER INFORMATION: a, t, c, g, unknown or other
<220> FEATURE:
<221> NAME/KEY: modified_base
<222> LOCATION: (616)..(616)
<223> OTHER INFORMATION: a, t, c, g, unknown or other
<220> FEATURE:
<221> NAME/KEY: modified_base
<222> LOCATION: (621)..(621)
<223> OTHER INFORMATION: a, t, c, g, unknown or other
<220> FEATURE:
<221> NAME/KEY: modified_base
<222> LOCATION: (623)..(623)
<223> OTHER INFORMATION: a, t, c, g, unknown or other
<220> FEATURE:
<221> NAME/KEY: modified_base
<222> LOCATION: (626)..(626)
<223> OTHER INFORMATION: a, t, c, g, unknown or other
<220> FEATURE:
<221> NAME/KEY: modified_base
<222> LOCATION: (629)..(629)
<223> OTHER INFORMATION: a, t, c, g, unknown or other
<220> FEATURE:
<221> NAME/KEY: modified_base
<222> LOCATION: (631)..(631)
<223> OTHER INFORMATION: a, t, c, g, unknown or other
<220> FEATURE:
<221> NAME/KEY: modified_base
<222> LOCATION: (634)..(635)
<223> OTHER INFORMATION: a, t, c, g, unknown or other
<220> FEATURE:
<221> NAME/KEY: modified_base
<222> LOCATION: (644)..(644)
<223> OTHER INFORMATION: a, t, c, g, unknown or other
<220> FEATURE:
<221> NAME/KEY: modified_base
<222> LOCATION: (646)..(646)
<223> OTHER INFORMATION: a, t, c, g, unknown or other
<220> FEATURE:
<221> NAME/KEY: modified_base
<222> LOCATION: (651)..(652)
<223> OTHER INFORMATION: a, t, c, g, unknown or other
<220> FEATURE:
<221> NAME/KEY: modified_base
<222> LOCATION: (656)..(656)

-continued

<223> OTHER INFORMATION: a, t, c, g, unknown or other
<220> FEATURE:
<221> NAME/KEY: modified_base
<222> LOCATION: (658)..(659)
<223> OTHER INFORMATION: a, t, c, g, unknown or other
<220> FEATURE:
<221> NAME/KEY: modified_base
<222> LOCATION: (663)..(663)
<223> OTHER INFORMATION: a, t, c, g, unknown or other
<220> FEATURE:
<221> NAME/KEY: modified_base
<222> LOCATION: (668)..(668)
<223> OTHER INFORMATION: a, t, c, g, unknown or other
<220> FEATURE:
<221> NAME/KEY: modified_base
<222> LOCATION: (670)..(671)
<223> OTHER INFORMATION: a, t, c, g, unknown or other
<220> FEATURE:
<221> NAME/KEY: modified_base
<222> LOCATION: (673)..(673)
<223> OTHER INFORMATION: a, t, c, g, unknown or other
<220> FEATURE:
<221> NAME/KEY: modified_base
<222> LOCATION: (675)..(676)
<223> OTHER INFORMATION: a, t, c, g, unknown or other
<220> FEATURE:
<221> NAME/KEY: modified_base
<222> LOCATION: (678)..(678)
<223> OTHER INFORMATION: a, t, c, g, unknown or other

<400> SEQUENCE: 61

```
tgtggccttt tttttttttt tttttttttt nnntnngggg tttttttttnn naaactctnt     60
ccaagtcccn ncntttaang ncaggnaggg cttcaaccca aacacaagcn gtntacatac    120
cataaaaaaa gggacctgag ggcntntnan ncnnncntgg gggggtacan annaaccttg    180
gcccaancca anggnggggt tnagggcctg naaaaaaaan ggttngnttt ttccccctcc    240
nnntnttttt ttcntcccgg gctttaaagt ccggggaaaa aaaagttttt aattanggga    300
actnntaagg cctnangggc cgcngngggt aananntggt tgaccnaatt aattaaanat    360
gtcncttaat aanaaaanan nncccanntt tcccaagnna aacccnnctn nggngggcct    420
nncncnccnc ccncccactn cttnacancn naaacannta nttnnangcc nggcncatng    480
cccnnncccn tnatcctcnn cntcaaatc nancccncnn ntaatntcnc ncannnncng    540
nnnanncccnn nntnaanacc nncttanncc ccttncccnt cngcncctcc cgngttatat    600
ngnanngntc ctnnanattt ntntgnatna nccnngcccc aacncnctct nnccanannt    660
ttnttccncn ncncnncntc cccccc                                          686
```

<210> SEQ ID NO 62
<211> LENGTH: 420
<212> TYPE: DNA
<213> ORGANISM: Homo sapiens
<220> FEATURE:
<223> OTHER INFORMATION: hyst-2056-f

<400> SEQUENCE: 62

```
gtaaccagcc ctgggaagcc cgcaagaggc ctcagcggtg gccgtccgag agccgagagg     60
tgagggtgcc cccgcctcac ctgcagaggg gccgttccgg gctcgaaccc ggcaccttcc    120
ggaaaatggc ggctgccagg cccagcctgg gccgagtcct cccaggatcc tctgtcctgt    180
tcctgtgtga catgcaggag aagttccgcc acaacatcgc ctacttccca cagatcgtct    240
cagtggctgc ccgcatgctc aaggtggccc ggctgcttga ggtgccagtc atgctgacgg    300
agcagtaccc acaaggcctg ggccccacgg tgcccgagct ggggactgag ggccttcggc    360
cgctggccaa gacctgcttc agcatggtgc ctgccctgca gcaggagctg gacagtcggc    420
```

<210> SEQ ID NO 63
<211> LENGTH: 605
<212> TYPE: DNA
<213> ORGANISM: Homo sapiens
<220> FEATURE:
<223> OTHER INFORMATION: hyst-2056-r
<220> FEATURE:
<221> NAME/KEY: modified_base
<222> LOCATION: (62)..(62)
<223> OTHER INFORMATION: a, t, c, g, unknown or other
<220> FEATURE:
<221> NAME/KEY: modified_base
<222> LOCATION: (65)..(65)
<223> OTHER INFORMATION: a, t, c, g, unknown or other
<220> FEATURE:
<221> NAME/KEY: modified_base
<222> LOCATION: (68)..(68)
<223> OTHER INFORMATION: a, t, c, g, unknown or other
<220> FEATURE:
<221> NAME/KEY: modified_base
<222> LOCATION: (72)..(72)
<223> OTHER INFORMATION: a, t, c, g, unknown or other
<220> FEATURE:
<221> NAME/KEY: modified_base
<222> LOCATION: (98)..(98)
<223> OTHER INFORMATION: a, t, c, g, unknown or other
<220> FEATURE:
<221> NAME/KEY: modified_base
<222> LOCATION: (103)..(103)
<223> OTHER INFORMATION: a, t, c, g, unknown or other
<220> FEATURE:
<221> NAME/KEY: modified_base
<222> LOCATION: (109)..(109)
<223> OTHER INFORMATION: a, t, c, g, unknown or other
<220> FEATURE:
<221> NAME/KEY: modified_base
<222> LOCATION: (112)..(112)
<223> OTHER INFORMATION: a, t, c, g, unknown or other
<220> FEATURE:
<221> NAME/KEY: modified_base
<222> LOCATION: (135)..(135)
<223> OTHER INFORMATION: a, t, c, g, unknown or other
<220> FEATURE:
<221> NAME/KEY: modified_base
<222> LOCATION: (142)..(142)
<223> OTHER INFORMATION: a, t, c, g, unknown or other
<220> FEATURE:
<221> NAME/KEY: modified_base
<222> LOCATION: (146)..(146)
<223> OTHER INFORMATION: a, t, c, g, unknown or other
<220> FEATURE:
<221> NAME/KEY: modified_base
<222> LOCATION: (155)..(155)
<223> OTHER INFORMATION: a, t, c, g, unknown or other
<220> FEATURE:
<221> NAME/KEY: modified_base
<222> LOCATION: (157)..(157)
<223> OTHER INFORMATION: a, t, c, g, unknown or other
<220> FEATURE:
<221> NAME/KEY: modified_base
<222> LOCATION: (174)..(174)
<223> OTHER INFORMATION: a, t, c, g, unknown or other
<220> FEATURE:
<221> NAME/KEY: modified_base
<222> LOCATION: (181)..(181)
<223> OTHER INFORMATION: a, t, c, g, unknown or other
<220> FEATURE:
<221> NAME/KEY: modified_base
<222> LOCATION: (184)..(184)
<223> OTHER INFORMATION: a, t, c, g, unknown or other
<220> FEATURE:
<221> NAME/KEY: modified_base
<222> LOCATION: (186)..(186)
<223> OTHER INFORMATION: a, t, c, g, unknown or other
<220> FEATURE:
<221> NAME/KEY: modified_base
<222> LOCATION: (188)..(188)

-continued

<223> OTHER INFORMATION: a, t, c, g, unknown or other
<220> FEATURE:
<221> NAME/KEY: modified_base
<222> LOCATION: (199)..(199)
<223> OTHER INFORMATION: a, t, c, g, unknown or other
<220> FEATURE:
<221> NAME/KEY: modified_base
<222> LOCATION: (205)..(205)
<223> OTHER INFORMATION: a, t, c, g, unknown or other
<220> FEATURE:
<221> NAME/KEY: modified_base
<222> LOCATION: (208)..(208)
<223> OTHER INFORMATION: a, t, c, g, unknown or other
<220> FEATURE:
<221> NAME/KEY: modified_base
<222> LOCATION: (223)..(223)
<223> OTHER INFORMATION: a, t, c, g, unknown or other
<220> FEATURE:
<221> NAME/KEY: modified_base
<222> LOCATION: (225)..(225)
<223> OTHER INFORMATION: a, t, c, g, unknown or other
<220> FEATURE:
<221> NAME/KEY: modified_base
<222> LOCATION: (227)..(227)
<223> OTHER INFORMATION: a, t, c, g, unknown or other
<220> FEATURE:
<221> NAME/KEY: modified_base
<222> LOCATION: (234)..(234)
<223> OTHER INFORMATION: a, t, c, g, unknown or other
<220> FEATURE:
<221> NAME/KEY: modified_base
<222> LOCATION: (248)..(248)
<223> OTHER INFORMATION: a, t, c, g, unknown or other
<220> FEATURE:
<221> NAME/KEY: modified_base
<222> LOCATION: (256)..(256)
<223> OTHER INFORMATION: a, t, c, g, unknown or other
<220> FEATURE:
<221> NAME/KEY: modified_base
<222> LOCATION: (260)..(260)
<223> OTHER INFORMATION: a, t, c, g, unknown or other
<220> FEATURE:
<221> NAME/KEY: modified_base
<222> LOCATION: (265)..(265)
<223> OTHER INFORMATION: a, t, c, g, unknown or other
<220> FEATURE:
<221> NAME/KEY: modified_base
<222> LOCATION: (271)..(271)
<223> OTHER INFORMATION: a, t, c, g, unknown or other
<220> FEATURE:
<221> NAME/KEY: modified_base
<222> LOCATION: (279)..(279)
<223> OTHER INFORMATION: a, t, c, g, unknown or other
<220> FEATURE:
<221> NAME/KEY: modified_base
<222> LOCATION: (290)..(290)
<223> OTHER INFORMATION: a, t, c, g, unknown or other
<220> FEATURE:
<221> NAME/KEY: modified_base
<222> LOCATION: (304)..(304)
<223> OTHER INFORMATION: a, t, c, g, unknown or other
<220> FEATURE:
<221> NAME/KEY: modified_base
<222> LOCATION: (310)..(310)
<223> OTHER INFORMATION: a, t, c, g, unknown or other
<220> FEATURE:
<221> NAME/KEY: modified_base
<222> LOCATION: (317)..(317)
<223> OTHER INFORMATION: a, t, c, g, unknown or other
<220> FEATURE:
<221> NAME/KEY: modified_base
<222> LOCATION: (319)..(319)
<223> OTHER INFORMATION: a, t, c, g, unknown or other
<220> FEATURE:
<221> NAME/KEY: modified_base
<222> LOCATION: (322)..(322)
<223> OTHER INFORMATION: a, t, c, g, unknown or other
<220> FEATURE:
<221> NAME/KEY: modified_base
<222> LOCATION: (330)..(330)
<223> OTHER INFORMATION: a, t, c, g, unknown or other
<220> FEATURE:
<221> NAME/KEY: modified_base
<222> LOCATION: (333)..(333)
<223> OTHER INFORMATION: a, t, c, g, unknown or other
<220> FEATURE:
<221> NAME/KEY: modified_base
<222> LOCATION: (336)..(336)
<223> OTHER INFORMATION: a, t, c, g, unknown or other
<220> FEATURE:
<221> NAME/KEY: modified_base
<222> LOCATION: (347)..(347)
<223> OTHER INFORMATION: a, t, c, g, unknown or other
<220> FEATURE:
<221> NAME/KEY: modified_base
<222> LOCATION: (350)..(350)
<223> OTHER INFORMATION: a, t, c, g, unknown or other
<220> FEATURE:
<221> NAME/KEY: modified_base
<222> LOCATION: (352)..(352)
<223> OTHER INFORMATION: a, t, c, g, unknown or other
<220> FEATURE:
<221> NAME/KEY: modified_base
<222> LOCATION: (354)..(354)
<223> OTHER INFORMATION: a, t, c, g, unknown or other
<220> FEATURE:
<221> NAME/KEY: modified_base
<222> LOCATION: (362)..(362)
<223> OTHER INFORMATION: a, t, c, g, unknown or other
<220> FEATURE:
<221> NAME/KEY: modified_base
<222> LOCATION: (372)..(372)
<223> OTHER INFORMATION: a, t, c, g, unknown or other
<220> FEATURE:
<221> NAME/KEY: modified_base
<222> LOCATION: (394)..(394)
<223> OTHER INFORMATION: a, t, c, g, unknown or other
<220> FEATURE:
<221> NAME/KEY: modified_base
<222> LOCATION: (435)..(435)
<223> OTHER INFORMATION: a, t, c, g, unknown or other
<220> FEATURE:
<221> NAME/KEY: modified_base
<222> LOCATION: (461)..(461)
<223> OTHER INFORMATION: a, t, c, g, unknown or other
<220> FEATURE:
<221> NAME/KEY: modified_base
<222> LOCATION: (468)..(468)
<223> OTHER INFORMATION: a, t, c, g, unknown or other
<220> FEATURE:
<221> NAME/KEY: modified_base
<222> LOCATION: (471)..(471)
<223> OTHER INFORMATION: a, t, c, g, unknown or other
<220> FEATURE:
<221> NAME/KEY: modified_base
<222> LOCATION: (480)..(480)
<223> OTHER INFORMATION: a, t, c, g, unknown or other
<220> FEATURE:
<221> NAME/KEY: modified_base
<222> LOCATION: (486)..(486)
<223> OTHER INFORMATION: a, t, c, g, unknown or other
<220> FEATURE:
<221> NAME/KEY: modified_base
<222> LOCATION: (492)..(492)
<223> OTHER INFORMATION: a, t, c, g, unknown or other
<220> FEATURE:
<221> NAME/KEY: modified_base
<222> LOCATION: (508)..(508)
<223> OTHER INFORMATION: a, t, c, g, unknown or other
<220> FEATURE:
<221> NAME/KEY: modified_base
<222> LOCATION: (516)..(516)
<223> OTHER INFORMATION: a, t, c, g, unknown or other
<220> FEATURE:
<221> NAME/KEY: modified_base
<222> LOCATION: (523)..(523)
<223> OTHER INFORMATION: a, t, c, g, unknown or other
<220> FEATURE:

<221> NAME/KEY: modified_base
<222> LOCATION: (525)..(525)
<223> OTHER INFORMATION: a, t, c, g, unknown or other
<220> FEATURE:
<221> NAME/KEY: modified_base
<222> LOCATION: (527)..(527)
<223> OTHER INFORMATION: a, t, c, g, unknown or other
<220> FEATURE:
<221> NAME/KEY: modified_base
<222> LOCATION: (529)..(529)
<223> OTHER INFORMATION: a, t, c, g, unknown or other
<220> FEATURE:
<221> NAME/KEY: modified_base
<222> LOCATION: (534)..(534)
<223> OTHER INFORMATION: a, t, c, g, unknown or other
<220> FEATURE:
<221> NAME/KEY: modified_base
<222> LOCATION: (542)..(542)
<223> OTHER INFORMATION: a, t, c, g, unknown or other
<220> FEATURE:
<221> NAME/KEY: modified_base
<222> LOCATION: (549)..(549)
<223> OTHER INFORMATION: a, t, c, g, unknown or other
<220> FEATURE:
<221> NAME/KEY: modified_base
<222> LOCATION: (566)..(566)
<223> OTHER INFORMATION: a, t, c, g, unknown or other
<220> FEATURE:
<221> NAME/KEY: modified_base
<222> LOCATION: (574)..(574)
<223> OTHER INFORMATION: a, t, c, g, unknown or other

<400> SEQUENCE: 63
tgtggccttt ttttttttt ttttttttt ttttttttt tttgccacat atatgtttat 60
tntgngantc cntgtcccac aatctgaaac tttttttncc ctnccettnc cnccccgtga 120 aatggcccgg ggccnaaccc cncctncatt ttggntnaac caattcccac ccantttcca 180
ngantntnat ttgcatttnc gggancanct gtccaatggg aangnancac cctnecccce 240 cccacaangg ggcggnactn ctggnggatc ncaccactnt tgggatccan ggatgggggg 300
aacnggcttn cactgangnc cnggtgacan ganggnggtc ttccctnaan gnanggttgg 360
anttcaatgg angagggagt tctggccttg gaanaaagccc aacagtccgc tgtctggggc 420
gggctccttg atgantttct ggatctcctt gaactggggg nggacggnat ngcccacaan 480
ctgcanaatg anccccttcgc tggtggganaa gaaagnacca ctntntntna tgcnggccaa 540
anccaccanc cggtccacct ggctgngtga ggancaagcg ttcaccacca catggacctg 600
caacc 605

<210> SEQ ID NO 64
<211> LENGTH: 1842
<212> TYPE: DNA
<213> ORGANISM: Homo sapiens
<220> FEATURE:
<223> OTHER INFORMATION: hyst-2477

<400> SEQUENCE: 64
ttctaggcct gtacggaagt gttacttctg ctctaaaagc tgcggaattc ctcgagcact 60
gttggcctac tggattgctg cagacgctca ccccagacac tcactgcacc ggagtgagcg 120
cgaccatcat gtccatgctc gtggtctttc tcttgctgtg gggtgtcacc tggggcccag 180
tgacagaagc agccatattt tatgagacgc agcccagcct gtgggcagag tccgaatcac 240
tgctgaaacc cttggccaat gtgacgctga cgtgccaggc ccacctggag actccagact 300
tccagctgtt caagaatggg gtggcccagg agcctgtgca ccttgactca cctgccatca 360
agcaccagtt cctgctgacg ggtgacaccc agggccgcta ccgctgccgc tcgggcttgt 420

```
ccacaggatg gacccagctg agcaagctcc tggagctgac agggccaaag tccttgcctg    480

ctccctggct ctcgatggcg ccagtgtcct ggatcacccc cggcctgaaa acaacagcag    540

tgtgccgagg tgtgctgcgg ggtgtgactt ttctgctgag gcgggagggc gaccatgagt    600

ttctggaggt gcctgaggcc caggaggatg tggaggccac ctttccagtc catcagcctg    660

gcaactacag ctgcagctac cggaccgatg ggaaggcgc cctctctgag cccagcgcta     720

ctgtgaccat tgaggagctc gctgcaccac caccgcctgt gctgatgcac catggagagt    780

cctcccaggt cctgcaccct ggcaacaagg tgaccctcac ctgcgtggct cccctgagtg    840

gagtggactt ccagctacgg cgcggggaga aagagctgct ggtacccagg agcagcacca    900

gcccagatcg catcttcttt cacctgaacg cggtggccct gggggatgga ggtcactaca    960

cctgccgcta ccggctgcat gacaaccaaa acggctggtc cggggacagc gcgccggtcg   1020

agctgattct gagcgatgag acgctgcccg cgccggagtt ctccccggag ccggagtccg   1080

gcagggcctt gcggctgcgg tgcctggcgc ccctggaggg cgcgcgcttc gccctggtgc   1140

gcgaggacag gggcgggcgc cgcgtgcacc gtttccagag ccccgctggg accgaggcgc   1200

tcttcgagct gcacaacatt tccgtggctg actccgccaa ctacagctgc gtctacgtgg   1260

acctgaagcc gcctttcggg ggctccgcgc ccagcgagcg cttggagctg cacgtggacg   1320

gaccccctcc caggcctcag ctccgggcga cgtggagtgg ggcggtcctg gcgggccgag   1380

atgccgtcct gcgctgcgag ggacccatcc ccgacgtcac cttcgagctg ctgcgcgagg   1440

gcgagacgaa ggccgtgaag acggtccgca cccccggggc cgcggcgaac ctcgagctga   1500

tcttcgtggg gccccagcac gccggcaact acaggtgccg ctaccgctcc tgggtgcccc   1560

acaccttcga atcggagctc agcgaccctg tggagctcct ggtggcagaa agctgatgca   1620

gccgcgggcc cagggtgctg ttggtgtcct cagaagtgcc ggggattctg gactggctcc   1680

ctcccctcct gttgcagcac aaggccgggg tctctggggg gctggagaag cctccctcat   1740

tcctcccagg aattaataaa tgtgaagaga ggctctgttt aaaatgtcaa aaaaaaaaaa   1800

aaaggccaca tgtgctcgag ctgcaggtcg cggccgctag ac                      1842
```

<210> SEQ ID NO 65
<211> LENGTH: 498
<212> TYPE: DNA
<213> ORGANISM: Homo sapiens
<220> FEATURE:
<223> OTHER INFORMATION: hyst-2623-f

<400> SEQUENCE: 65

```
caggaaaata aaaatgttca aactccttgg atgttgggat aaactcacct gaacccactt     60

gggttcgggc tgcctccttc tcttccttca ttgccacctt tcctctgtgt ggctcccggg    120

agtgtgcggt taagtcatca gactcgaagt gcctagagat ccggaggaag ccgcgccggt    180

cttcccctga catgcgtggc atgccggggc tccgtaggag gtttgctata cctgggagga    240

ccctggcatt ctaaatttca gctccgggaa agagaagggg ctttttgcct tttatctttt    300

tttttctttt ctttaagtag taattttttta actgattcat tgtttggaaa gcgcatattg   360

cttccctctt ccccgaattc tggcaactct tcctcctgct atgatgggcc cttgggcatc    420

atgaacttca ttactcctca ctggctggaa ttcaaactgc ccatctgtag tggtcccgtg    480

cgttgaccat gcacctga                                                  498
```

<210> SEQ ID NO 66

-continued

<211> LENGTH: 585
<212> TYPE: DNA
<213> ORGANISM: Homo sapiens
<220> FEATURE:
<223> OTHER INFORMATION: hyst-2623-r
<220> FEATURE:
<221> NAME/KEY: modified_base
<222> LOCATION: (47)..(47)
<223> OTHER INFORMATION: a, t, c, g, unknown or other
<220> FEATURE:
<221> NAME/KEY: modified_base
<222> LOCATION: (52)..(53)
<223> OTHER INFORMATION: a, t, c, g, unknown or other
<220> FEATURE:
<221> NAME/KEY: modified_base
<222> LOCATION: (55)..(55)
<223> OTHER INFORMATION: a, t, c, g, unknown or other
<220> FEATURE:
<221> NAME/KEY: modified_base
<222> LOCATION: (75)..(75)
<223> OTHER INFORMATION: a, t, c, g, unknown or other
<220> FEATURE:
<221> NAME/KEY: modified_base
<222> LOCATION: (91)..(91)
<223> OTHER INFORMATION: a, t, c, g, unknown or other
<220> FEATURE:
<221> NAME/KEY: modified_base
<222> LOCATION: (103)..(104)
<223> OTHER INFORMATION: a, t, c, g, unknown or other
<220> FEATURE:
<221> NAME/KEY: modified_base
<222> LOCATION: (114)..(114)
<223> OTHER INFORMATION: a, t, c, g, unknown or other
<220> FEATURE:
<221> NAME/KEY: modified_base
<222> LOCATION: (128)..(128)
<223> OTHER INFORMATION: a, t, c, g, unknown or other
<220> FEATURE:
<221> NAME/KEY: modified_base
<222> LOCATION: (137)..(137)
<223> OTHER INFORMATION: a, t, c, g, unknown or other
<220> FEATURE:
<221> NAME/KEY: modified_base
<222> LOCATION: (152)..(152)
<223> OTHER INFORMATION: a, t, c, g, unknown or other
<220> FEATURE:
<221> NAME/KEY: modified_base
<222> LOCATION: (154)..(154)
<223> OTHER INFORMATION: a, t, c, g, unknown or other
<220> FEATURE:
<221> NAME/KEY: modified_base
<222> LOCATION: (163)..(163)
<223> OTHER INFORMATION: a, t, c, g, unknown or other
<220> FEATURE:
<221> NAME/KEY: modified_base
<222> LOCATION: (166)..(166)
<223> OTHER INFORMATION: a, t, c, g, unknown or other
<220> FEATURE:
<221> NAME/KEY: modified_base
<222> LOCATION: (215)..(215)
<223> OTHER INFORMATION: a, t, c, g, unknown or other
<220> FEATURE:
<221> NAME/KEY: modified_base
<222> LOCATION: (223)..(223)
<223> OTHER INFORMATION: a, t, c, g, unknown or other
<220> FEATURE:
<221> NAME/KEY: modified_base
<222> LOCATION: (226)..(226)
<223> OTHER INFORMATION: a, t, c, g, unknown or other
<220> FEATURE:
<221> NAME/KEY: modified_base
<222> LOCATION: (249)..(249)
<223> OTHER INFORMATION: a, t, c, g, unknown or other
<220> FEATURE:
<221> NAME/KEY: modified_base
<222> LOCATION: (252)..(252)
<223> OTHER INFORMATION: a, t, c, g, unknown or other
<220> FEATURE:
<221> NAME/KEY: modified_base -continued
<222> LOCATION: (254)..(254)
<223> OTHER INFORMATION: a, t, c, g, unknown or other
<220> FEATURE:
<221> NAME/KEY: modified_base
<222> LOCATION: (265)..(266)
<223> OTHER INFORMATION: a, t, c, g, unknown or other
<220> FEATURE:
<221> NAME/KEY: modified_base
<222> LOCATION: (272)..(272)
<223> OTHER INFORMATION: a, t, c, g, unknown or other
<220> FEATURE:
<221> NAME/KEY: modified_base
<222> LOCATION: (283)..(283)
<223> OTHER INFORMATION: a, t, c, g, unknown or other
<220> FEATURE:
<221> NAME/KEY: modified_base
<222> LOCATION: (288)..(288)
<223> OTHER INFORMATION: a, t, c, g, unknown or other
<220> FEATURE:
<221> NAME/KEY: modified_base
<222> LOCATION: (316)..(316)
<223> OTHER INFORMATION: a, t, c, g, unknown or other
<220> FEATURE:
<221> NAME/KEY: modified_base
<222> LOCATION: (318)..(318)
<223> OTHER INFORMATION: a, t, c, g, unknown or other
<220> FEATURE:
<221> NAME/KEY: modified_base
<222> LOCATION: (330)..(330)
<223> OTHER INFORMATION: a, t, c, g, unknown or other
<220> FEATURE:
<221> NAME/KEY: modified_base
<222> LOCATION: (340)..(340)
<223> OTHER INFORMATION: a, t, c, g, unknown or other
<220> FEATURE:
<221> NAME/KEY: modified_base
<222> LOCATION: (346)..(346)
<223> OTHER INFORMATION: a, t, c, g, unknown or other
<220> FEATURE:
<221> NAME/KEY: modified_base
<222> LOCATION: (350)..(350)
<223> OTHER INFORMATION: a, t, c, g, unknown or other
<220> FEATURE:
<221> NAME/KEY: modified_base
<222> LOCATION: (352)..(352)
<223> OTHER INFORMATION: a, t, c, g, unknown or other
<220> FEATURE:
<221> NAME/KEY: modified_base
<222> LOCATION: (363)..(363)
<223> OTHER INFORMATION: a, t, c, g, unknown or other
<220> FEATURE:
<221> NAME/KEY: modified_base
<222> LOCATION: (365)..(365)
<223> OTHER INFORMATION: a, t, c, g, unknown or other
<220> FEATURE:
<221> NAME/KEY: modified_base
<222> LOCATION: (385)..(385)
<223> OTHER INFORMATION: a, t, c, g, unknown or other
<220> FEATURE:
<221> NAME/KEY: modified_base
<222> LOCATION: (420)..(420)
<223> OTHER INFORMATION: a, t, c, g, unknown or other
<220> FEATURE:
<221> NAME/KEY: modified_base
<222> LOCATION: (431)..(431)
<223> OTHER INFORMATION: a, t, c, g, unknown or other
<220> FEATURE:
<221> NAME/KEY: modified_base
<222> LOCATION: (437)..(437)
<223> OTHER INFORMATION: a, t, c, g, unknown or other
<220> FEATURE:
<221> NAME/KEY: modified_base
<222> LOCATION: (441)..(441)
<223> OTHER INFORMATION: a, t, c, g, unknown or other
<220> FEATURE:
<221> NAME/KEY: modified_base
<222> LOCATION: (457)..(457)
<223> OTHER INFORMATION: a, t, c, g, unknown or other
<220> FEATURE:

-continued

<221> NAME/KEY: modified_base
<222> LOCATION: (468)..(468)
<223> OTHER INFORMATION: a, t, c, g, unknown or other
<220> FEATURE:
<221> NAME/KEY: modified_base
<222> LOCATION: (470)..(470)
<223> OTHER INFORMATION: a, t, c, g, unknown or other
<220> FEATURE:
<221> NAME/KEY: modified_base
<222> LOCATION: (488)..(488)
<223> OTHER INFORMATION: a, t, c, g, unknown or other
<220> FEATURE:
<221> NAME/KEY: modified_base
<222> LOCATION: (495)..(496)
<223> OTHER INFORMATION: a, t, c, g, unknown or other
<220> FEATURE:
<221> NAME/KEY: modified_base
<222> LOCATION: (538)..(538)
<223> OTHER INFORMATION: a, t, c, g, unknown or other
<220> FEATURE:
<221> NAME/KEY: modified_base
<222> LOCATION: (557)..(557)
<223> OTHER INFORMATION: a, t, c, g, unknown or other
<220> FEATURE:
<221> NAME/KEY: modified_base
<222> LOCATION: (563)..(563)
<223> OTHER INFORMATION: a, t, c, g, unknown or other
<220> FEATURE:
<221> NAME/KEY: modified_base
<222> LOCATION: (567)..(567)
<223> OTHER INFORMATION: a, t, c, g, unknown or other

<400> SEQUENCE: 66
tgtggccttt tttttttttt tttttttttt tttttttttt ttttttnttt tnnanaggaa 60
agcagtattt attgnataaa agttatactt nttaatcaaa ggnncaaacg aaanctaaaa 120
cttaaagntg accatantat tgacaagtca tntnaacctg gtnccngcta aatttaatga 180
aaataagttc cactgaattc ctaaggaaaa tacancaatt ccnacnccat ttaataatta 240
aaaactttna ancnagaggg aaagnntgaa cntcataata aangcctnaa tttggaggca 300
aaaaaatgta agttgngngc tgaaacctgn tgtatcacan aacatnagtn gncccttcca 360
gtngnggatg ccttaaaccc aaggncttac actgttatca ccatttggca accctgatgn 420
gggatgccat ntattgnctg nctgaaatta aattacncaa tgggactntn tgcctgtcag 480
caaaacanag agtcnnaaaa cattttaact tcttggggca aattatacaa ttcaaccnaa 540
taaccttgac tgggaangaa ccngttnaaa ggggtgaatt ttttt 585

<210> SEQ ID NO 67
<211> LENGTH: 510
<212> TYPE: DNA
<213> ORGANISM: Homo sapiens
<220> FEATURE:
<223> OTHER INFORMATION: hmfn-0217-f

<400> SEQUENCE: 67
ataaaccagg tgcctgctga cacgaaggaa gattccgggg cattttgatc ctagtcacac 60
agtgtttcta agtgggcatt actcctgtca atccacagtc ttaaagatgt tcctcagaca 120
aaagataatt agtgacaaga aggcccacta gattccatgt catatcttag ttggcgggcc 180
agagaaggac agggtctctg gttggggccg tgtctcccat cgcattctcc ctttgcaggt 240
gctgaagtga ggaaggccca cagctcagcc aagcacatgg ggtgcctccc tcctgggcca 300
ctagcccact ggccagtaag agaaccaggg agcctttact tagagactca aggttcagaa 360
gagggaaatg ggaagtcact gggaaatggc ccagcttgga ggaggtgacc ctgctgccga 420
atctgacccc ttatcctatt acctaagttc ctttcttgtt tactggccct gaaatcaccc 480
gctttggaga ttgccttgca aggcagcata 510

<210> SEQ ID NO 68
<211> LENGTH: 666
<212> TYPE: DNA
<213> ORGANISM: Homo sapiens
<220> FEATURE:
<223> OTHER INFORMATION: hkmt-0668-f

<400> SEQUENCE: 68
atgcgaactg gggccacggc agccatcgcg ctttgcagtt cggtctcctg gtgtacggcc 60
aacgccaagt aggggattgc gttccctcca gtcgcagagt ttccctcttg tcgcccaggc 120
tggagtgaag tggcacgatc tcggcttact gcaagctccg cctcccgggt tcacgccatt 180
ctcctgcctc agcctcccga gtagctggga ctacagaccc tatcagattt ggatatgtcc 240
ttcatatttg attggattta cagtggtttc agcagtgtgc tacagttttt aggattatat 300
aagaaaactg gtaaactggt atttcttgga ttggataatg caggaaaaac aacattgcta 360
cacatactaa aagatgacag acttggacaa catgtcccaa cattacatcc cacttccgaa 420
gaactgacca ttgctggcat gacgtttaca actttgatc tgggtggaca tgttcaagct 480
cgaagagtgt ggaaaaacta ccttcctgct atcaatggca ttgtatttct ggtggattgt 540
gcagaccacg aaaggctgtt agagtcaaaa gaagaacttg attcactaat gacagatgaa 600
accattgcta atgtgcctat actgattctt gggaataaga tcgacagacc tgaagccatc 660
agtgaa 666

<210> SEQ ID NO 69
<211> LENGTH: 597
<212> TYPE: DNA
<213> ORGANISM: Homo sapiens
<220> FEATURE:
<223> OTHER INFORMATION: hmfn-0668-r
<220> FEATURE:
<221> NAME/KEY: modified_base
<222> LOCATION: (53)..(54)
<223> OTHER INFORMATION: a, t, c, g, unknown or other
<220> FEATURE:
<221> NAME/KEY: modified_base
<222> LOCATION: (89)..(89)
<223> OTHER INFORMATION: a, t, c, g, unknown or other
<220> FEATURE:
<221> NAME/KEY: modified_base
<222> LOCATION: (112)..(112)
<223> OTHER INFORMATION: a, t, c, g, unknown or other
<220> FEATURE:
<221> NAME/KEY: modified_base
<222> LOCATION: (124)..(124)
<223> OTHER INFORMATION: a, t, c, g, unknown or other
<220> FEATURE:
<221> NAME/KEY: modified_base
<222> LOCATION: (133)..(133)
<223> OTHER INFORMATION: a, t, c, g, unknown or other
<220> FEATURE:
<221> NAME/KEY: modified_base
<222> LOCATION: (168)..(168)
<223> OTHER INFORMATION: a, t, c, g, unknown or other
<220> FEATURE:
<221> NAME/KEY: modified_base
<222> LOCATION: (170)..(170)
<223> OTHER INFORMATION: a, t, c, g, unknown or other
<220> FEATURE:
<221> NAME/KEY: modified_base
<222> LOCATION: (177)..(177)
<223> OTHER INFORMATION: a, t, c, g, unknown or other
<220> FEATURE:
<221> NAME/KEY: modified_base
<222> LOCATION: (189)..(189)

<223> OTHER INFORMATION: a, t, c, g, unknown or other
<220> FEATURE:
<221> NAME/KEY: modified_base
<222> LOCATION: (212)..(212)
<223> OTHER INFORMATION: a, t, c, g, unknown or other
<220> FEATURE:
<221> NAME/KEY: modified_base
<222> LOCATION: (220)..(220)
<223> OTHER INFORMATION: a, t, c, g, unknown or other
<220> FEATURE:
<221> NAME/KEY: modified_base
<222> LOCATION: (244)..(244)
<223> OTHER INFORMATION: a, t, c, g, unknown or other
<220> FEATURE:
<221> NAME/KEY: modified_base
<222> LOCATION: (265)..(265)
<223> OTHER INFORMATION: a, t, c, g, unknown or other
<220> FEATURE:
<221> NAME/KEY: modified_base
<222> LOCATION: (285)..(285)
<223> OTHER INFORMATION: a, t, c, g, unknown or other
<220> FEATURE:
<221> NAME/KEY: modified_base
<222> LOCATION: (314)..(314)
<223> OTHER INFORMATION: a, t, c, g, unknown or other
<220> FEATURE:
<221> NAME/KEY: modified_base
<222> LOCATION: (327)..(327)
<223> OTHER INFORMATION: a, t, c, g, unknown or other
<220> FEATURE:
<221> NAME/KEY: modified_base
<222> LOCATION: (334)..(334)
<223> OTHER INFORMATION: a, t, c, g, unknown or other
<220> FEATURE:
<221> NAME/KEY: modified_base
<222> LOCATION: (337)..(337)
<223> OTHER INFORMATION: a, t, c, g, unknown or other
<220> FEATURE:
<221> NAME/KEY: modified_base
<222> LOCATION: (339)..(339)
<223> OTHER INFORMATION: a, t, c, g, unknown or other
<220> FEATURE:
<221> NAME/KEY: modified_base
<222> LOCATION: (344)..(344)
<223> OTHER INFORMATION: a, t, c, g, unknown or other
<220> FEATURE:
<221> NAME/KEY: modified_base
<222> LOCATION: (389)..(389)
<223> OTHER INFORMATION: a, t, c, g, unknown or other
<220> FEATURE:
<221> NAME/KEY: modified_base
<222> LOCATION: (460)..(460)
<223> OTHER INFORMATION: a, t, c, g, unknown or other
<220> FEATURE:
<221> NAME/KEY: modified_base
<222> LOCATION: (502)..(502)
<223> OTHER INFORMATION: a, t, c, g, unknown or other
<220> FEATURE:
<221> NAME/KEY: modified_base
<222> LOCATION: (516)..(516)
<223> OTHER INFORMATION: a, t, c, g, unknown or other
<220> FEATURE:
<221> NAME/KEY: modified_base
<222> LOCATION: (551)..(551)
<223> OTHER INFORMATION: a, t, c, g, unknown or other
<220> FEATURE:
<221> NAME/KEY: modified_base
<222> LOCATION: (593)..(593)
<223> OTHER INFORMATION: a, t, c, g, unknown or other
<220> FEATURE:
<221> NAME/KEY: modified_base
<222> LOCATION: (596)..(596)
<223> OTHER INFORMATION: a, t, c, g, unknown or other

<400> SEQUENCE: 69
tgtggccttt tttttttttt tttttttttt tttttttttt ttgactgaca cannaacaag 60
ctgttttatt cctcaaatat acatgtctnt acaatgaaac tgcacacaag gncctactta 120

```
ttgnttgccc canagagtac tgttaaatgt acagagactg ggaatatntn taaatgngga    180

gacactggng cctgtcattg cttttgggga anaggcacan attaccccat tgggcaccaa    240

taanactgga gcacttcaaa attanacagc tgggatggaa ctatngagcc taccaaactg    300

agaatcaacc ttgngtacca taaatgngct tttnttnana aggncaatcc cacagggact    360

aggacacaga ccccatcagc aatggtagng gctgcattac taataaaaat acacatgatt    420

cagggataca tggtatcagg tgcaactgac cacaaccatn ttatggtaaa tacctaagcc    480

ttgagagcct taaacgctat tntaaatatt ctgaangaat cttcttttcc aacaaccact    540

tcatatgcct natattaaat actcaaattt ttaaagtata ctagctagat aanacnc       597
```

```
<210> SEQ ID NO 70
<211> LENGTH: 1929
<212> TYPE: DNA
<213> ORGANISM: Homo sapiens
<220> FEATURE:
<223> OTHER INFORMATION: hmfn-0839

<400> SEQUENCE: 70

ttgggatcag tttgctggtt ataggaacta cactggttgg gcagctgcca gacagcagcc     60

tcaaaaactg gctgagtgaa ctggtccatc tgacttgctg ccggatctgt gtgcgagccc    120

tctctggtac cattcattat cataacaagc agtacagacc ccagaaggga ggcatttgtg    180

ttgccaacca tacttccccc attgatgttt taatcttgac aacggatgga tgttatgcta    240

tggttggcca ggttcatggc ggcttgatgg gaattattca gagagctatg gtcaaggctt    300

gtcctcatgt ctggtttgaa cgctcagaaa tgaaggatcg acacctggtt actaagagac    360

taaaagaaca tattgctgat aagaagaaac tacccatact aatttttcct gaaggaactt    420

gcatcaacaa tacttcagtc atgatgttta aaaaggggag ctttgaaatt ggaggaacca    480

tacatccagt tgcaattaag tataaccctc agttcggtga tgcattttgg aacagtagta    540

aatacaacat ggtgagctac ctgcttcgaa tgatgaccag ctgggccatc gtctgtgacg    600

tgtggtacat gccccccatg accagagagg aaggagaaga tgcagtccag tttgctaaca    660

gggttaagtc tgctattgct atacaaggag gcctgactga acttccctgg gatggaggac    720

taaagagagc aaaggtgaag gacatcttta aggaagagca gcagaaaaat tacagcaaga    780

tgattgtggg caatggatct ctcagctaag aggacggatg acagccttta gatctagaac    840

tagcccttag aaatggaatg gctttttgt tttgttttgt tttattgttt tgtttttatt     900

attgttaatc ttttctacag aatgattgtc tctacctctt tatgccagag gcagaaccta    960

caggtgccct ttttggcttt tgttgttgtt gtaacattag ccccatggat tgtaaggtgg   1020

tttactgagt taaaacagat tctgcttttg taaaatgatg gcatcactgt ggactgaatg   1080

aaatatttgt atagaaaaaa gtgcttgaaa agtgtgtttg gaactcatcg atagggtaat   1140

tctccaaaaa tgcccaaact ctttttctgt aattagcctt gccactttct tcagtcactt   1200

aaatggtgag attacacatc agtgcaagat gaccattatg gttatggtct actgcaaggt   1260

tgaaaggaaa aatggaggat tgtatttagg aaaagggaca actttgtggc cacctgctct   1320

gaaagtcaaa aggaaatgta aattagtgtc attagtgtgt tggaagagaa atactattca   1380

gtaagcttcg ccaaagaaaa gtgagtcaaa gttaatgtgt gtgcgcattt atatgtaggc   1440

agctcgtaga ccacatttta accagcaact ggtaacaaag agcttagttt tccttgtttg   1500

aatgctgtag atctgtacct agtacccctc ccatctactg atttgtttgt ttttgtaacc   1560
```

-continued

```
aaacacattt tcagatagaa ggagccttaa aaaaaaaaat cacattgagt aacttcagta   1620

tgaatgaatg agagtgtgtg gagctacccc tcaccctcca cccctttgtg ctttttattc   1680

ccgaattttc ccagtctctt aaacagaaaa atgactgata taattatctt ttggaaactg   1740

agccttaatt ttttttagag ggggaaataa gttttcccca actcacacag cataagcaat   1800

gtttgacagc aatataatgc cgttgtaaac tactgagagt attgtatctg ttctggtaac   1860

catgtacaga atgtgaaact gtcttatgaa tataaataaa ttctatattt ctaaaaaaaa   1920

aaaaaaaaa                                                           1929
```

<210> SEQ ID NO 71
<211> LENGTH: 429
<212> TYPE: DNA
<213> ORGANISM: Homo sapiens
<220> FEATURE:
<223> OTHER INFORMATION: hmfn-2700-f

<400> SEQUENCE: 71

```
agagcagacc aggcccggtg gagaattagg tgctgctggg agctcctgcc tcccacagga     60

ttccagctgc agggagcctc agggactctg ggccgcacgg agttgggggc attccccaga    120

gagcgtcgcc atggtctgca gggagcagtt atcaaagaat caggtcaagt gggtgtttgc    180

cggcattacc tgtgtgtctg tggtggtcat tgccgcaata gtccttgcca tcaccctgcg    240

gcggccaggc tgtgagctgg aggcctgcag ccctgatgcc gacatgctgg actacctgct    300

gagcctgggc cagatcagcc ggcgagatgc cttggaggtc acctggtacc acgcagccaa    360

cagcaagaaa gccatgacag ctgccctgaa cagcaacatc acagtcctgg aggctgacgt    420

caatgtaga                                                            429
```

<210> SEQ ID NO 72
<211> LENGTH: 420
<212> TYPE: DNA
<213> ORGANISM: Homo sapiens
<220> FEATURE:
<223> OTHER INFORMATION: hkmt-2698-f

<400> SEQUENCE: 72

```
ttgcttataa atttttacc actcccacat aaaatgctca tagtttggga gaggaaagag      60

ggaagattct ctcttctttt aacagagaga tgattgctct gtatacccat tgcttcctcc    120

ctgaggctgt cccaaagtga acactgatgg agtggtcaaa atcataagat tgtagcaagc    180

caaagatacg tatgtgacgg aagcacataa gcaataagca gaaaaccaga agtgcatgct    240

gtgatgcctg tgactccttc atcccgctca gtgccatgtc ctcttttgtg atcttccaga    300

aagctccagg attcatttga gttccacatc caagtaacag atgaattata ttcatgttgt    360

aatgcatttt gtggagttta caaaaccagt gtctgttaaa actttggaaa atgtcttaga    420
```

<210> SEQ ID NO 73
<211> LENGTH: 517
<212> TYPE: DNA
<213> ORGANISM: Homo sapiens
<220> FEATURE:
<223> OTHER INFORMATION: hkmt-2698-r

<400> SEQUENCE: 73

```
tgtggccttt tttttttttt tttttaaaaa caatttccaa atacaaaaca tggattattc     60

aaagtggatt tttcctatac atatatataa ttctgctgca aacagtggat caaaaagcag    120

aagtgttctt agcatgattc atctttgaaa acccatagaa ctattcataa atccaattag    180
```

```
aaagaacatg tgcaaaacca ccaacaatgt cagcaaaacc tcaaagatct gattttggtt    240

gaagtagaga gaaaataaac ataaagcagt acctgtttac agtaattaaa tatgtttttt    300

ctttatcttt ctttcttaaa tatgtctttt tttaaatgtt tgcaagaaac tctaagggct    360

aaggaaatgc actgcattat gatctgggct ccttagagta caaacctcac caggcttaag    420

catcatccat aagaaatggt ggattactta atgacttata agtaaaacag tcattaaatg    480

atcctttcat actttaatcc tcttatgcag agactga                             517


<210> SEQ ID NO 74
<211> LENGTH: 484
<212> TYPE: DNA
<213> ORGANISM: Homo sapiens
<220> FEATURE:
<223> OTHER INFORMATION: hyst-2198-f

<400> SEQUENCE: 74

gtgcagcggc cgcagtgctg cgtccgtgcg ccgcgggctg gggcggtctc aggtgtgccg     60

aagctctggt cagtgccatg atccggcagg agcgctccac atcctaccag gagctgagtg    120

aggagttggt ccaggtggtt gagaactcag agctggcaga cgagcaggac aaggagaact    180

cagagtccaa ggtccgggta tcttaccagg cctggacagc gagtccgcct ccagcagcat    240

ccgcttcagc aaggcctgcc tgaagaacgt cttctcggtc ctactcatct tcatctacct    300

gctgctcatg gctgtggccg tcttcctggt ctaccggacc atcacagact ttcgtgagaa    360

actcaagcac cctgtcatgt ctgtgtctta caaggaagtg gatcgctatg atgccccagg    420

tattgccttg taccccggtc aggcccagtt gctcagctgt aagcaccatt acgaggtcat    480

tcct                                                                 484


<210> SEQ ID NO 75
<211> LENGTH: 629
<212> TYPE: DNA
<213> ORGANISM: Homo sapiens
<220> FEATURE:
<223> OTHER INFORMATION: hyst-2198-r
<220> FEATURE:
<221> NAME/KEY: modified_base
<222> LOCATION: (46)..(46)
<223> OTHER INFORMATION: a, t, c, g, unknown or other
<220> FEATURE:
<221> NAME/KEY: modified_base
<222> LOCATION: (48)..(48)
<223> OTHER INFORMATION: a, t, c, g, unknown or other
<220> FEATURE:
<221> NAME/KEY: modified_base
<222> LOCATION: (72)..(72)
<223> OTHER INFORMATION: a, t, c, g, unknown or other
<220> FEATURE:
<221> NAME/KEY: modified_base
<222> LOCATION: (100)..(100)
<223> OTHER INFORMATION: a, t, c, g, unknown or other
<220> FEATURE:
<221> NAME/KEY: modified_base
<222> LOCATION: (105)..(105)
<223> OTHER INFORMATION: a, t, c, g, unknown or other
<220> FEATURE:
<221> NAME/KEY: modified_base
<222> LOCATION: (115)..(115)
<223> OTHER INFORMATION: a, t, c, g, unknown or other
<220> FEATURE:
<221> NAME/KEY: modified_base
<222> LOCATION: (124)..(124)
<223> OTHER INFORMATION: a, t, c, g, unknown or other
<220> FEATURE:
<221> NAME/KEY: modified_base
<222> LOCATION: (134)..(134)
```

<223> OTHER INFORMATION: a, t, c, g, unknown or other
<220> FEATURE:
<221> NAME/KEY: modified_base
<222> LOCATION: (166)..(166)
<223> OTHER INFORMATION: a, t, c, g, unknown or other
<220> FEATURE:
<221> NAME/KEY: modified_base
<222> LOCATION: (202)..(202)
<223> OTHER INFORMATION: a, t, c, g, unknown or other
<220> FEATURE:
<221> NAME/KEY: modified_base
<222> LOCATION: (227)..(227)
<223> OTHER INFORMATION: a, t, c, g, unknown or other
<220> FEATURE:
<221> NAME/KEY: modified_base
<222> LOCATION: (272)..(272)
<223> OTHER INFORMATION: a, t, c, g, unknown or other
<220> FEATURE:
<221> NAME/KEY: modified_base
<222> LOCATION: (292)..(292)
<223> OTHER INFORMATION: a, t, c, g, unknown or other
<220> FEATURE:
<221> NAME/KEY: modified_base
<222> LOCATION: (324)..(324)
<223> OTHER INFORMATION: a, t, c, g, unknown or other
<220> FEATURE:
<221> NAME/KEY: modified_base
<222> LOCATION: (361)..(361)
<223> OTHER INFORMATION: a, t, c, g, unknown or other
<220> FEATURE:
<221> NAME/KEY: modified_base
<222> LOCATION: (388)..(388)
<223> OTHER INFORMATION: a, t, c, g, unknown or other
<220> FEATURE:
<221> NAME/KEY: modified_base
<222> LOCATION: (400)..(400)
<223> OTHER INFORMATION: a, t, c, g, unknown or other
<220> FEATURE:
<221> NAME/KEY: modified_base
<222> LOCATION: (421)..(421)
<223> OTHER INFORMATION: a, t, c, g, unknown or other
<220> FEATURE:
<221> NAME/KEY: modified_base
<222> LOCATION: (430)..(430)
<223> OTHER INFORMATION: a, t, c, g, unknown or other
<220> FEATURE:
<221> NAME/KEY: modified_base
<222> LOCATION: (464)..(464)
<223> OTHER INFORMATION: a, t, c, g, unknown or other
<220> FEATURE:
<221> NAME/KEY: modified_base
<222> LOCATION: (488)..(488)
<223> OTHER INFORMATION: a, t, c, g, unknown or other
<220> FEATURE:
<221> NAME/KEY: modified_base
<222> LOCATION: (603)..(603)
<223> OTHER INFORMATION: a, t, c, g, unknown or other
<220> FEATURE:
<221> NAME/KEY: modified_base
<222> LOCATION: (618)..(618)
<223> OTHER INFORMATION: a, t, c, g, unknown or other
<220> FEATURE:
<221> NAME/KEY: modified_base
<222> LOCATION: (628)..(628)
<223> OTHER INFORMATION: a, t, c, g, unknown or other

<400> SEQUENCE: 75
tgtggccttt tttttttttt tttttttttt tttttttttt cctttngnat aaacttttat 60
ttacctgtta angaaatcat caaaatacaa tgagtaggcn ccttntatgt acatntgtcc 120
tagngctttt gagngttaat ctaaactcat acatcaacaa acattntagc cggacaagta 180
gggggctact cagtccatta anaaacttaa ttactagttt ctagtancct taaagtctca 240
tttaacattt aacaaatcaa agagcatgtc anaggctgga catcaatggc anatgatgcc 300
aaagtcatag ggttttgcct ttgngtacag ggcataggct ccaaagcatg acctgcacgt 360

```
nttgatactc aggaattttt ggaaaaanaa aatcacactn ttttgtccac ttttaaaaag    420

ngaaaagtan agccttcatt accctagtag agcttaacct aatncaatac aatgaaccaa    480

acaggaanaa aggcatcttc tacaaaccct attcaaaagt cattggccag ctctttaaaa    540

agtttattaa taatttaaat atttaaataa cttggaggtt tatccattag tctcttctat    600

tangctctac accgcctntt ttgggacng                                      629


<210> SEQ ID NO 76
<211> LENGTH: 564
<212> TYPE: DNA
<213> ORGANISM: Homo sapiens
<220> FEATURE:
<223> OTHER INFORMATION: hyst-2935-f

<400> SEQUENCE: 76

ctggagggct tttaaggagt cacagtgcca tcacatgctc aaacatctcc acaatggtgc     60

aaggatcaca gtgcagatgc cacctacaat cgagggccac tgggtctcca caggctgtga    120

agtaaggtca ggcccagagt tcatcacaag gtcctacaga ttctaccaca ataacacctt    180

caaggcctac caattttatt atggcagcaa ccggtgcaca aatcccactt atactctcat    240

catccggggc aagatccgcc tccgccaggc ctcctggatc atccgagggg gcacggaagc    300

cgactaccag ctgcacaaca tccaggtgat ctgccacaca gaggcggtgg ctgagaagct    360

gggccagcag gtgaaccgca catgcccggg cttcctcgca gacgggggtc cctgggtgca    420

ggacgtggcc tatgacctct ggcgagagga gaacggctgt gagtgcacca aggccgtgaa    480

ctttgccatg catgaacttc agctcatccg ggtggagaag cagtaccttc accacaacct    540

cgaccacctg gtcgaggagc tctt                                           564


<210> SEQ ID NO 77
<211> LENGTH: 533
<212> TYPE: DNA
<213> ORGANISM: Homo sapiens
<220> FEATURE:
<223> OTHER INFORMATION: hyst-2935-r

<400> SEQUENCE: 77

tgtggccttt tttttttttt tttaaattac ttcgaaactt taattacaga tacttttcca     60

cgcaacattt ctgaaatgaa agctttgatt ctccccttttt cttgcataaa ggctgggaag   120

gtggtttggc cagaccgtac atctttttgt atatacatat ctacacctgt gtctcttctt    180

tattaataaa aggtgtcttg atcacagtcc caaaccaact ctgcattgga ttccagcata    240

taaaactcag agagtaaaac aattttaaag gaagacaggc tgcaaccaca ggaaaatggc    300

aggaaaagtt gtagcttgat agttgtttct tctaagttta actcagaaat ataataataa    360

ttaagagaaa aaaataagag gccctagctt tcatccctgc taccaaacac gctcgtccag    420

aactctaggc tgtcttaaag tgcaattact gttgtgaagt tgctcaggcc agggatcagg    480

ctggacggag ttcaaagcag aaacttcaaa cactccttgc tgttcatgac tca           533


<210> SEQ ID NO 78
<211> LENGTH: 401
<212> TYPE: DNA
<213> ORGANISM: Homo sapiens
<220> FEATURE:
<223> OTHER INFORMATION: hmft-1511-f

<400> SEQUENCE: 78
```

-continued

```
gtggagactc gagcctgggg tcggcggaga cagctggtgt ctgaagccgc tcgcgcccag     60

ggtgaccctg tttgcagcac gatgtctgaa gaagaggcgg ctcagatccc cagatccagt    120

gtgtgggagc aggaccagca gaacgtggtg cagcgtgtgg tggctctgcc cctggtcagg    180

gccacgtgca ccgcggtctg cgatgtttac agtgcagcca aggacaggca cccgctgctg    240

ggctccgcct gccgcctggc tgagaactgc gtgtgcggcc tgaccacccg tgccctggac    300

cacgcccagc cgctgctcga gcacctgcag ccccagctgg ccactatgaa cagcctcgcc    360

tgcaggggcc tggacaagct ggaagagaag cttccctttc t                        401
```

<210> SEQ ID NO 79
<211> LENGTH: 466
<212> TYPE: DNA
<213> ORGANISM: Homo sapiens
<220> FEATURE:
<223> OTHER INFORMATION: hmft-1511-r

<400> SEQUENCE: 79

```
tgtggccttt tttttttttt ttttgaaacg gagtctcgca ctgtggcctg ggctggagtg     60

caatagcgcg atctcagctc attgcaacct ccacctccca ggctcaagtg attctcctgc    120

ctcagcctcc cgagtatctg ggaatacagg cacacgccac cacgcctggc taattttttg    180

tatttttagt agagacggga tttcactatg ttggccaggc tgggctcgaa ctcctgacct    240

catgatctgc ccaccttggc ctcccaaagt gctgagatta caggcgtgag ccactgtgcc    300

tggcagtgtg tctggttttt caaaacaagc caagaatcgg gacatgtaat gcaaaatctg    360

gttgttaaat gcatgcaaag aatgaaaata tttaaaacac gctgcacagg catttggggg    420

ccaccagttt gggacctcaa gtctaaaagc cctatatgcc cttagg                   466
```

<210> SEQ ID NO 80
<211> LENGTH: 1656
<212> TYPE: DNA
<213> ORGANISM: Homo sapiens
<220> FEATURE:
<223> OTHER INFORMATION: hkmt-0020

<400> SEQUENCE: 80

```
cgcccctgct ctcgcgccgg cgtcggctgc gtctccggcg tttgaattgc gcttccgcca     60

tctttccagc ctcagtcgga cgggcgcgga ggcgcttctg gaaggaacgc cgcgatggct    120

gcgcagggag agccccaggt ccagttcaaa cttgtattgg ttggtgatgg tggtactgga    180

aaaacgacct tcgtgaaacg tcatttgact ggtgaatttg agaagaagta tgtagccacc    240

ttgggtgttg aggttcatcc cctagtgttc cacaccaaca gaggacctat taagttcaat    300

gtatgggaca cagccggcca ggagaaattc ggtggactga gagatggcta ttatatccaa    360

gcccagtgtg ccatcataat gtttgatgta acatcgagag ttacttacaa gaatgtgcct    420

aactggcata gagatctggt acgagtgtgt gaaaacatcc ccattgtgtt gtgtggcaac    480

aaagtggata ttaaggacag gaaagtgaag gcgaaatcca ttgtcttcca ccgaaagaag    540

aatcttcagt actacgacat ttctgccaaa agtaactaca actttgaaaa gcccttcctc    600

tggcttgcta ggaagctcat tggagaccct aacttggaat ttgttgccat gcctgctctc    660

gccccaccag aagttgtcat ggacccagct ttggcagcac agtatgagca cgacttagag    720

gttgctcaga caactgctct cccggatgag gatgatgacc tgtgagaatg aagctggagc    780

ccagcgtcag aagtctagtt ttataggcag ctgtcctgtg atgtcagcgg tgcagcgtgt    840

gtgccacctc attattatct agctaagcgg aacatgtgct ttatctgtgg gatgctgaag    900
```

```
gagatgagtg ggcttcggag tgaatgtggc agtttaaaaa ataacttcat tgtttggacc    960

tgcatattta gctgtttgga cgcagttgat tccttgagtt tcatatataa gactgctgca   1020

gtcacatcac aatattcagt ggtgaaatct tgtttgttac tgtcattccc attccttttc   1080

tttagaatca gaataaagtt gtatttcaaa tatctaagca agtgaactca tcccttgttt   1140

ataaatagca tttggaaacc actaaagtag ggaagtttta tgccatgtta atatttgaat   1200

tgccttgctt ttatcactta atttgaaatc tattgggtta atttctccct atgtttattt   1260

ttgtacattt gagccatgtc acacaaactg atgatgacag gtcagcagta ttctatttgg   1320

ttagaagggt tacatggtgt aaatattagt gcagttaagc taaagcagtg tttgctccac   1380

cttcatattg gctaggtagg gtcacctagg gaagcacttg ctcaaaatct gtgacctgtc   1440

agaataaaaa tgtggtttgt acatatcaaa tagatatttt aagggtaata ttttctttta   1500

tggcaaaagt aatcatgttt taatgtagaa cctcaaacag gatggaacat cagtggatgg   1560

caggaggttg ggaattcttg ctgttaaaaa taattacaaa ttttgcactt tttgtttgaa   1620

tgttagatgc ttagtgtgaa gttgatacgc aagccg                             1656
```

```
<210> SEQ ID NO 81
<211> LENGTH: 3247
<212> TYPE: DNA
<213> ORGANISM: Homo sapiens
<220> FEATURE:
<223> OTHER INFORMATION: hkmt-0359

<400> SEQUENCE: 81
```

```
gaggagctct gcgcggcgcg gcgggcgatc cgagccggga cgggctgcag gcgggggtgc     60

tgcagaggac acgaggcggc gggctggaga catggaccgc ggcgagcaag gtctgctgag    120

aacagaccca gtccctgagg aaggagaaga tgttgctgcc acgatcagtg ccacagagac    180

cctctcggaa gaggagcagg aagagctaag aagagaactt gcaaaggtag aagaagaaat    240

ccagactctg tctcaagtgt tagcagcaaa agagaagcat ctagcagaga tcaagcggaa    300

acttggaatc aattctctac aggaactaaa acagaacatt gccaaagggt ggcaagacgt    360

gacagcaaca tctgcttaca agaagacatc tgaaacctta tcccaggctg gacagaaggc    420

ctcagctgct tttttcgtctg ttggctcagt catcaccaaa aagctggaag atgtaaaaaa    480

ctccccaact tttaaatcat ttgaagaaaa ggtcgaaaac ttaaagtcta aagtaggggg    540

aaccaagcct gctggtggtg attttggaga agtcttgaat tcggctgcaa atgctagtgc    600

caccaccacg gagcctcttc cagaaaagac acaggagagc ctgtgagatt cctacctttg    660

ttctgctacc cactgccaga tgctgcaagc gaggtccaag cacatcttgt caacatgcat    720

tgccatgaat ttctaccaga tgtgctttta tttagcttta catattcctt tgaccaaata    780

gtttgtgggt taaacaaaat gaaaatatct tcacctctat tcttgggaaa caccctttag    840

tgtacattta tgttccttta tttaggaaac accattataa aaacacttat agtaaatggg    900

gacattcact ataatgatct aagaagctac agattgtcat agttgttttc ctgctttaca    960

aaattgctcc agatctggaa tgccagtttg acctttgtct tctataatat ttcctttttt   1020

tcccctcttt gaatctctgt atatttgatt cttaactaaa attgttctct taaatattct   1080

gaatcctggt aattaaaagt ttgggtgtat tttctttacc tccaaggaaa gaactactag   1140

ctacaaaaaa tattttggaa taagcattgt tttggtataa ggtacatatt ttggttgaag   1200

acaccagact gaagtaaaca gctgtgcatc caatttatta tagttttgta agtaacaata   1260
```

-continued

```
tgtaatcaaa cttctaggtg acttgagagt ggaacctcct atatcattat ttagcaccgt   1320
ttgtgacagt aaccatttca gtgtattgtt tattatacca cttatatcaa cttatttttc   1380
accaggttaa aattttaatt tctacaaaat aacattctga atcaagcaca ctgtatgttc   1440
agtaggttga actatgaaca ctgtcatcaa tgttcagttc aaaagcctga aagtttagat   1500
ctagaagctg gtaaaaatga caatatcaat cacattaggg gaaccattgt tgtcttcact   1560
taatccattt agcactattt aaaataagca caccaagtta tatgactaat ataacttgaa   1620
aatttttat actgaggggt tggtgataac tcttgaggat gtaatgcatt aataaaaatc    1680
aactcatcat tttctacttg ttttcaatgt gttggaaact gtaaaatgat actgtagaac   1740
ctgtctccta ctttgaaaac tgaatgtcag ggctgagtga atcaaagtgt ctagacatat   1800
ttgcatagag gccaaggtat tctattctaa taactgctta ctcaacacta ccaccttttc   1860
cttatactgt atatgattat ggcctacaat gttgtatttg ttatttatta aattgtgatt   1920
gttttattat tgtttatgcc aaatgttaac tgccaagctt ggagtgacct aaagcatttt   1980
ttaaaagcat ggctagattt acttcagtat aaattatctt atgaaaacca aattttaaaa   2040
gccacaggtg ttgattgtta taaaataaca tgctgccatt cttgattgct agagtttttg   2100
ttagtacttt ggatgcaatt aaaactatgt gctatcacat gtgaaaagct taataaattc   2160
catctatcag tagtataggt ctcaatattt attatgagac cagtggtctg gaaacagctt   2220
gttgtaccga atcaactgga gtctatgctt aaaaaaaaaa attttttttt aaccatcctt   2280
aaattattgc ttaatggtat catattaaca tattctaaat aagggcttta aggcacaggc   2340
tgttgaagca ttttctcaga ggagtggatc tgtagaagtc tgtctttcta tagaaatatt   2400
gtgcttactc aagtgttaaa ttattttttc tatgaactag tctacttctt aaaattcaaa   2460
catattcttt tgatcacatt gtttcttgag catcctgccc tgctactaac ttttcaacaa   2520
ggcaaaatgg agtaaagtgg caatttcttt agatgagtga aataccctca agtctctttt   2580
ctgcccaaaa agggaaaagt gatagaaatg ggggtggcaa gtggggtgag tggatgaagg   2640
tgggtattgg gggtggctgt gaaagaaaat aatggagaat cacttttcta gacatctacc   2700
tatacttaat ctaagaaaca aagtaatcta ctgtaaagta ctctgcccct tgaaagaagt   2760
attaaaaaga gtgaggatgg atttagaaaa aaacatgaat ttagaaatat tcaaaatggt   2820
ttttgtggca gattcaatat tatgaattca cagatattta aagaatgaga aacatagtaa   2880
ttagtagaaa tgccagaaac agttcctggt tcctcttgtg tttgacacta agaaaatagc   2940
aagagtgtga aatctcagat acttatgaaa tctcacagat gtaaggactc aagtgtagaa   3000
gaaaatatcc ccttcttaca aaaagaaatg tcaatttatg gagtttgtgg gaaatagggc   3060
aagaattctt atgcttatga gagccaagta gtcagtggaa gagagtagag ctcaaaactg   3120
gattatcacc ttagcaactt agaatagttt gaaatagaaa aaaagtattt aatttggatc   3180
tggatctgtt aagatatgca cagtctattt tttgtatagt attggaaaat aaaaatgcta   3240
taatttg                                                             3247
```

<210> SEQ ID NO 82
<211> LENGTH: 2506
<212> TYPE: DNA
<213> ORGANISM: Homo sapiens
<220> FEATURE:
<223> OTHER INFORMATION: hkmt-1013

<400> SEQUENCE: 82

```
ggcacgaggc acagcttcgc gccgtgtact gtcgccccat ccctgcgcgc ccagcctgcc     60
```

-continued

```
aagcagcgtg ccccggttgc aggcgtcatg cagcgggcgc gacccacgct ctgggccgct    120
gcgctgactc tgctggtgct gctccgcggg ccgccggtgg cgcgggctgg cgcgagctcg    180
gggggcttgg gtcccgtggt gcgctgcgag ccgtgcgacg cgcgtgcact ggcccagtgc    240
gcgcctccgc ccgccgtgtg cgcggagctg gtgcgcgagc cgggctgcgg ctgctgcctg    300
acgtgcgcac tgagcgaggg ccagccgtgc ggcatctaca ccgagcgctg tggctccggc    360
cttcgctgcc agccgtcgcc cgacgaggcg cgaccgctgc aggcgctgct ggacggccgc    420
gggctctgcg tcaacgctag tgccgtcagc cgcctgcgcg cctacctgct gccagcgccg    480
ccagctccag gaaatgctag tgagtcggag gaagaccgca gcgccggcag tgtggagagc    540
ccgtccgtct ccagcacgca ccgggtgtct gatcccaagt tccacccccct ccattcaaag    600
ataatcatca tcaagaaagg gcatgctaaa gacagccagc gctacaaagt tgactacgag    660
tctcagagca cagataccca gaacttctcc tccgagtcca agcgggagac agaatatggt    720
ccctgccgta gagaaatgga agacacactg aatcacctga agttcctcaa tgtgctgagt    780
cccaggggtg tacacattcc caactgtgac aagaagggat tttataagaa aaagcagtgt    840
cgcccttcca aaggcaggaa gcggggcttc tgctggtgtg tggataagta tgggcagcct    900
ctcccaggct acaccaccaa ggggaaggag gacgtgcact gctacagcat gcagagcaag    960
tagacgcctg ccgcaaggtt aatgtggagc tcaaatatgc cttattttgc acaaaagact   1020
gccaaggaca tgaccagcag ctggctacag cctcgattta tatttctgtt tgtggtgaac   1080
tgattttttt taaaccaaag tttagaaaga ggtttttgaa atgcctatgg tttctttgaa   1140
tggtaaactt gagcatcttt tcactttcca gtagtcagca aagagcagtt tgaattttct   1200
tgtcgcttcc tatcaaaata ttcagagact cgagcacagc acccagactt catgcgcccg   1260
tggaatgctc accacatgtt ggtcgaagcg gccgaccact gactttgtga cttaggcggc   1320
tgtgttgcct atgtagagaa cacgcttcac cccccactccc cgtacagtgc gcacaggctt   1380
tatcgagaat aggaaaacct ttaaaccccg gtcatccgga catcccaacg catgctcctg   1440
gagctcacag ccttctgtgg tgtcatttct gaaacaaggg cgtggatccc tcaaccaaga   1500
agaatgttta tgtcttcaag tgacctgtac tgcttgggga ctattggaga aaataaggtg   1560
gagtcctact tgtttaaaaa atatgtatct aagaatgttc tagggcactc tgggaaccta   1620
taaaggcagg tatttcgggc cctcctcttc aggaatcttc ctgaagacat ggcccagtcg   1680
aaggcccagg atggcttttg ctgcggcccc gtggggtagg agggacagag agacagggag   1740
agtcagcctc cacattcaga ggcatcacaa gtaatgtcac aattcttcgg atgactgcag   1800
aaaatagtgt tttgtagttc aacaactcaa gacgaagctt atttctgagg ataagctctt   1860
taaaggcaaa gctttatttt catctctcat cttttgtcct ccttagcaca atgtaaaaaa   1920
gaatagtaat atcagaacag gaaggaggaa tggcttgctg gggagcccat ccaggacact   1980
gggagcacat agagattcac ccatgtttgt tgaacttaga gtcattctca tgcttttctt   2040
tataattcac acatatatgc agagaagata tgttcttgtt aacattgtat acaacatagc   2100
cccaaatata gtaagatcta tactagataa tcctagatga aatgttagag atgctatttg   2160
atacaactgt ggccatgact gaggaaagga gctcacgccc agagactggg ctgctctccc   2220
ggaggccaaa cccaagaagg tctggcaaag tcaggctcag ggagactctg ccctgctgca   2280
gacctcggtg tggacacacg ctgcatagag ctctccttga aaacagaggg gtctcaagac   2340
attctgccta cctattagct tttctttatt tttttaactt tttgggggga aaagtatttt   2400
```

-continued

```
tgagaagttt gtcttgcaat gtatttataa atagtaaata aagtttttac cattaaaaaa   2460

ataaaaaaaa aaaaaaaaaa aaaaaaaaaa aaaaaaaaaa aaaaaa                  2506


<210> SEQ ID NO 83
<211> LENGTH: 1776
<212> TYPE: DNA
<213> ORGANISM: Homo sapiens
<220> FEATURE:
<223> OTHER INFORMATION: hfmn-0043

<400> SEQUENCE: 83

tttaataata attctgtgtt gcttctgaga ttaataattg attaattcat agtcaggaat     60

ctttgtaaaa aggaaaccaa ttacttttgg ctaccacttt tacatggtca cctacaggag    120

agaggaggtg ctgcaagact ctctggtaga aaaatgaaga gggtcctggt actactgctt    180

gctgtggcat ttggacatgc tttagagaga ggccgggatt atgaaaagaa taaagtctgc    240

aaggaattct cccatctggg aaaggaggac ttcacatctc tgtcactagt cctgtacagt    300

agaaaatttc ccagtggcac gtttgaacag gtcagccaac ttgtgaagga agttgtctcc    360

ttgaccgaag cctgctgtgc ggaaggggct gaccctgact gctatgacac caggacctca    420

gcactgtctg ccaagtcctg tgaaagtaat tctccattcc ccgttcaccc aggcactgct    480

gagtgctgca ccaaagaggg cctggaacga aagctctgca tggctgctct gaaacaccag    540

ccacaggaat tccctaccta cgtggaaccc acaaatgatg aaatctgtga ggcgttcagg    600

aaagatccaa aggaatatgc taatcaattt atgtgggaat attccactaa ttacggacaa    660

gctcctctgt cacttttagt cagttacacc aagagttatc tttctatggt agggtcctgc    720

tgtacctctg caagcccaac tgtatgcttt ttgaaagaga gactccagct taaacattta    780

tcacttctca ccactctgtc aaatagagtc tgctcacaat atgctgctta tggggagaag    840

aaatcaaggc tcagcaatct cataaagtta gcccaaaaag tgcctactgc tgatctggag    900

gatgttttgc cactagctga agatattact aacatcctct ccaaatgctg tgagtctgcc    960

tctgaagatt gcatggccaa agagctgcct gaacacacag taaaactctg tgacaattta   1020

tccacaaaga attctaagtt tgaagactgt tgtcaagaaa aaacagccat ggacgttttt   1080

gtgtgcactt acttcatgcc agctgcccaa ctccccgagc ttccagatgt agagttgccc   1140

acaaacaaag atgtgtgtga tccaggaaac accaaagtca tggataagta tacatttgaa   1200

ctaagcagaa ggactcatct tccggaagta ttcctcagta aggtacttga gccaacccta   1260

aaaagccttg gtgaatgctg tgatgttgaa gactcaacta cctgttttaa tgctaagggc   1320

cctctactaa agaaggaact atcttctttc attgacaagg gacaagaact atgtgcagat   1380

tattcagaaa atacatttac tgagtacaag aaaaaactgg cagagcgact aaaagcaaaa   1440

ttgcctgatg ccacacccaa ggaactggca aagctggtta acaagcgctc agactttgcc   1500

tccaactgct gttccataaa ctcacctcct ctttactgtg attcagagat tgatgctgaa   1560

ttgaagaata tcctgtagtc ctgaagcatg tttattaact ttgaccagag ttggagccac   1620

ccaggggaat gatctctgat gacctaacct aagcaaaacc actgagcttc tgggaagaca   1680

actaggatac tttctacttt ttctagctac aatatcttca tacaatgaca agtatgatga   1740

tttgctatca aaataaattg aaatataatg caaacc                              1776


<210> SEQ ID NO 84
<211> LENGTH: 1234
<212> TYPE: DNA
<213> ORGANISM: Homo sapiens
```

<220> FEATURE:
<223> OTHER INFORMATION: hmfn-0077

<400> SEQUENCE: 84

```
ctcttccaga ggcaagacca accaagatga gtgccttggg agctgtcatt gccctcctgc     60
tctggggaca gctttttgca gtggactcag gcaatgatgt cacggatatc gcagatgacg    120
gctgcccgaa gccccccgag attgcacatg gctatgtgga gcactcggtt cgctaccagt    180
gtaagaacta ctacaaactg cgcacagaag gagatggagt gtacacctta aacaatgaga    240
agcagtggat aaataaggct gttggagata aacttcctga atgtgaagca gtatgtggga    300
agcccaagaa tccggcaaac ccagtgcagc ggatcctggg tggacacctg gatgccaaag    360
gcagctttcc ctggcaggct aagatggttt cccaccataa tctcaccaca ggtgccacgc    420
tgatcaatga acaatggctg ctgaccacgg ctaaaaatct cttcctgaac cattcagaaa    480
atgcaacagc gaaagacatt gcccccactt taacactcta tgtggggaaa aagcagcttg    540
tagagattga gaaggttgtt ctacacccta actactccca agtagatatt gggctcatca    600
aactcaaaca gaaggtgtct gttaatgaga gagtgatgcc catctgccta ccatccaagg    660
attatgcaga agtagggcgt gtgggttatg tttctggctg gggggcgaaat gccaatttta    720
aatttactga ccatctgaag tatgtcatgc tgcctgtggc tgaccaagac caatgcataa    780
ggcattatga aggcagcaca gtccccgaaa agaagacacc gaagagccct gtaggggtgc    840
agcccatact gaatgaacac accttctgtg ctggcatgtc taagtaccaa gaagacacct    900
gctatggcga tgcgggcagt gcctttgccg ttcacgacct ggaggaggac acctggtatg    960
cgactgggat cttaagcttt gataagagct gtgctgtggc tgagtatggt gtgtatgtga   1020
aggtgacttc catccaggac tgggttcaga agaccatagc tgagaactaa tgcaaggctg   1080
gccggaagcc cttgcctgaa agcaagattt cagcctggaa gagggcaaag tggacgggag   1140
tggacaggag tggatgcgat aagatgtggt ttgaagctga tgggtgccag ccctgcattg   1200
ctgagtcaat caataaagag ctttcttttg accc                               1234
```

<210> SEQ ID NO 85
<211> LENGTH: 4080
<212> TYPE: DNA
<213> ORGANISM: Homo sapiens
<220> FEATURE:
<223> OTHER INFORMATION: hmfn-0722

<400> SEQUENCE: 85

```
gcactcaagc agagaagaaa tccacaaaga ctcacagtct gctggtgggc agagaagaca     60
gaaacgacat gagcacagca ggaaaagtaa tcaaatgcaa agcagctgtg ctatgggagg    120
taaagaaacc cttttccatt gaggatgtgg aggttgcacc tcctaaggct tatgaagttc    180
gcattaagat ggtggctgta ggaatctgtc acacagatga ccacgtggtt agtggcaacc    240
tggtgacccc ccttcctgtg attttaggcc atgaggcagc cggcatcgtg gagagtgttg    300
gagaaggggt gactacagtc aaaccaggtg ataaagtcat cccgctcttt actcctcagt    360
gtggaaaatg cagagtttgt aaaaacccgg agagcaacta ctgcttgaaa aatgatctag    420
gcaatcctcg gggggaccctg caggatggca ccaggaggtt cacctgcagg gggaagccca    480
ttcaccactt ccttggcacc agcaccttct cccagtacac ggtggtggat gagaatgcag    540
tggccaaaat tgatgcagcc tcgcccctgg agaaagtctg cctcattggc tgtggattct    600
cgactggtta tgggtctgca gttaacgttg ccaaggtcac cccaggctct acctgtgctg    660
```

-continued

```
tgtttggcct gggaggggtc ggcctatctg ctgttatggg ctgtaaagca gctggagcag    720
ccagaatcat tgcggtggac atcaacaagg acaaatttgc aaaggccaaa gagttgggtg    780
ccactgaatg catcaaccct caagactaca agaaacccat ccaggaagtg ctaaaggaaa    840
tgactgatgg aggtgtggat ttttcgtttg aagtcatcgg tcggcttgac accatgatgg    900
cttccctgtt atgttgtcat gaggcatgtg gcacaagcgt catcgtaggg gtacctcctg    960
cttcccagaa cctctcaata aaccctatgc tgctactgac tggacgcacc tggaaggggg   1020
ctgtttatgg tggctttaag agtaaagaag gtatcccaaa acttgtggct gattttatgg   1080
ctaagaagtt ttcactggat gcgttaataa cccatgtttt accttttgaa aaaataaatg   1140
aaggatttga cctgcttcac tctgggaaaa gtatccgtac cgtcctgacg ttttgaggca   1200
atagagatgc cttcccctgt agcagtcttc agcctcctct accctacaag atctggagca   1260
acagctagga aatatcatta attcagctct tcagagatgt tatcaataaa ttacacatgg   1320
gggctttcca aagaaatgga aattgatggg aaattatttt tcaggaaaat ttaaaattca   1380
agtgagaagt aaataaagtg ttgaacatca gctggggaat tgaagccaac aaaccttcct   1440
tcttaaccat tctactgtgt cacctttgcc attgaggaaa aatattcctg tgacttcttg   1500
catttttggt atcttcataa tctttagtca tcgaatccca gtggagggga cccttttact   1560
tgccctgaac atacacatgc tgggccattg tgattgaagt cttctaactc tgtctcagtt   1620
ttcactgtcg acattttcct ttttctaata aaaatgtacc aaatccctgg ggtaaaagct   1680
agggtaaggt aaaggataga ctcacattta caagtagtga aggtccgaga gttctaaata   1740
caggaaattt cttaggaact caaataaaat gccccacatt ttactacagt aaatggcagt   1800
gtttttatga cttttatact atttctttat ggtcgatata caattgattt tttaaaataa   1860
tagcagattt cttgcttcat atgacaaagc ctcaattact aattgtaaaa actgaactat   1920
tcccagaatc atgttcaaaa aatctgtaat ttttgctgat gaaagtgctt cattgactaa   1980
acagtattag tttgtggcta taaatgatta tttagatgat gactgaaaat gtgtataaag   2040
taattaaaag taatatggtg gctttaagtg tagagatggg atggcaaatg ctgtgaatgc   2100
agaatgtaaa attggtaact aagaaatggc acaaacacct taagcaatat attttcctag   2160
tagatatata tatacacata catatataca catatacaaa tgtatatttt tgcaaaattg   2220
ttttcaatct agaacttttc tattaactac catgtcttaa aatcaagtct ataatcctag   2280
cattagttta atattttgaa tatgtaaaga cctgtgttaa tgctttgtta atgcttttcc   2340
cactctcatt tgttaatgct ttcccactct caggggaagg atttgcattt tgagctttat   2400
ctctaaatgt gacatgcaaa gattattcct ggtaaaggag gtagctgtct ccaaaaatgc   2460
tattgttgca atatctacat tctatttcat attatgaaag accttagaca taaagtaaaa   2520
tagtttatca tttactgtgt gatcttcagt aagtctctca ggctctctga gcttgttcat   2580
cctttgtttt gaaaaaatta ctcaaccaat ccattacagc ttaaccaaga ttaaatggga   2640
tgatgttaat gaaagagctt cgccaattaa gaagggccat gtaaatgtgg gtaacctgat   2700
tgttttgtca aaaatgctaa agcggggtgg ggggtggcgc agtggcttat ccctgtaatc   2760
ccagcacttt gggaggtcaa gacgggtgga tgacctgagg tcaggagttt gagaccagcc   2820
tggtcaacat ggtgaaaccc catctctact aaaaatacaa aaatttgcca ggcatggtgg   2880
caggtggctg taatcccagc tactcaggag gctgaggcaa gagaatcgct ggagcctggg   2940
aggcggaggt tgcagtgagc agaaatcttg ccactgcaca ccagcctagg cgacaagagc   3000
aaaactctgt caaaagaaaa gaaaagaaaa tgctgaagga gttactcagg gtcaagaaag   3060
```

-continued

```
ttttcagaat gtccgtaaga taacatcatc atgggacact acctgttgct gggtgctctg   3120

cggcttttac actgatgctg attgtgtgag atccagaaaa agaaaatgga gttctacatg   3180

cccatctcac agcagggtca tcaaatcctg ctagtgacac agaagctgac atccagctcc   3240

cacccgcctt cctcccaggt tcggggagca ggtagagtgg gagccattag gtgggctctg   3300

ccagtgttgt catagagtgg caagtcctcc atgggatggg agtggcatgt gggagccttc   3360

tgcatcatgc actatgaaaa aagaaaattt actatggggc aagtggttca tatagttaag   3420

tgattgtata tatatatata tatatatata tatatatata cactatgggg caagtggttc   3480

atatagttaa gttgattgta tatatatata tatatatata tgtattccag tgtagaaagt   3540

attggctggg tctgtaatca agtattccac agaagtgcct tcataggtgc tgaaacagga   3600

ttatgagagt gacagacaca ggactgaaga cagggagaaa atgtgcatgg ctgtgagaat   3660

atattgcttt gattctttga cttctcatga tatatgaaaa caaataaagt ggggggggt   3720

gacttcaata atatcacgaa catatttaaa atgaaattct gagcatggag aaaaatttca   3780

aattctggta taaacaaata atctaaaaat atagataagg aaaaaatgtt ttcatttttt   3840

tggtcatatt gatttgggtc atatatgatt gaccaaaaaa aaagatattt ctaaaatcct   3900

ggtgcttttt catttaaaaa tagacaacca aagaggaaaa tgaacaatga tggaaattcg   3960

tggaagagga aactaaaatg gcaaaatagc atattaaatg gcactgagcc ttggtgtgat   4020

caaaaaaaaa aaaataaagc aaaatgagat attactgctt aaaaaaaaaa aaattaaaaa   4080
```

```
<210> SEQ ID NO 86
<211> LENGTH: 423
<212> TYPE: DNA
<213> ORGANISM: Homo sapiens
<220> FEATURE:
<223> OTHER INFORMATION: hmfn-1050

<400> SEQUENCE: 86

gcaatagaat gagagatttt taaacatata aaaagcagaa aaatataaat gaatcaggag     60

taaagtaaca ttaaaaattg gaatacattt aaagaaccat ctactaattt ctaaccatat    120

attattttta ataatggtct taaaatttct ttttctatag acaccaaatc tggctgaatg    180

aaataaattg gtgataagtg gaaaaaagag aaaaaccaat gattcataac aatgtatgtg    240

aaagtgtaaa atagaatgtt actttggaat gactataaac attaaaagaa gactggaagc    300

atacaacttt gtacatttgt gggggaaaac tattaatttt gcccaaatgg aaagatcaac    360

agactatata atgatacatg actgacactt gtacactagg taataaaact gattcataca    420

gtc                                                                  423
```

```
<210> SEQ ID NO 87
<211> LENGTH: 2405
<212> TYPE: DNA
<213> ORGANISM: Homo sapiens
<220> FEATURE:
<223> OTHER INFORMATION: hmfn-2802

<400> SEQUENCE: 87

atcacccatt ttctgcatca gtcacactgg gagctgcaga ccggagctgt tcctatttgc     60

ccatcctctc cctgctttct ttacctctga ggttggattc tccctgtggg atcctgcaat    120

ccttctgccc caaaaaacta ttatagcagg agggaacctg ttcctgctca ctctttgcct    180

tctccttctc atcctagaca gcctgaccgt gccctagttt tcagaggagt gattgattct    240
```

```
ggggtgcgga gcaggatgag gaaactcagg ctcagagagg gatttccacc taatgtgcct    300

ggaaaccatg ggtagctacc caataaggcc tttctatgtt cagaaggtca tggaccagga    360

gtgttggtat cggagctttg tagagacagt tttgacccct gtacttagag cagaggggtg    420

tgtttgccat ggagagtgtg tgtgggcagc tgtgtgtaag cctgtgtgag ttctgtgtat    480

gttcctgtgt gaatatatgt gtgtgctcct tcatggacac agcatgcatg tagtgggcat    540

agcaaggcag agagaaatca ggagactagg ggcacattgc ccagtaggaa gatagtatct    600

tcctactggg caggacttga ggtgtgcaaa ggtgtgcatg agtactgcaa aagcagttca    660

aagagcagag aggtggggcc agaataaata tgttgcagaa aggcagtcat cagggaggaa    720

agtgaggatt ccctgccaaa atgcctgagg gcttccctgc ctaccacagc cctctgtgtt    780

cttaaatcct cctgtctgaa cagaggccag actctggttt cccccacagc ctgtctgtgt    840

ctgtcctctg caaagccatg tggctctacc tggcggtttt cgtgggcctg tactaccttc    900

tgcactggta ccgggagagg caggtgctga gccacctgag agataagtat gtgttcatca    960

cgggctgtga ctctggcttc gggaaactgc tggccagaca gctggatgca cgaggcttgc   1020

gggtgctggc tgcatgtctg acggagaaag gagccgagca gctgaggggc cagacttcag   1080

acaggctgga gacggtgacc ctggatgtta ccaagacaga gagcgttgct gcagccgccc   1140

agtgggtgaa ggagtgcgtg agagacaaag gactctgggg cctggtgaat aatgctggca   1200

tctccttgcc cacggctccc aatgagttgc tcaccaagca ggacttcgtg accatactgg   1260

acgtgaactt gttgggggtg attgatgtga ctctgagcct gctgccctta gtgaggaggg   1320

ccaggggccg tgtggtcaac gtctccagtg tcatgggccg ggtgtcactt tttggtggag   1380

gctactgcat ctccaagtat ggcgtggaag ccttctctga ctccctcagg agggaactct   1440

cctactttgg ggtgaaggtg gctatgattg aacctggcta tttcaagact gctgtgacca   1500

gtaaggagag attcttaaag agcttcctgg agatttggga ccggtccagt ccagaggtca   1560

aggaggccta tggcgagaag tttgttgcag actataagaa atcagctgaa caaatggagc   1620

agaagtgcac acaggatctg tcgttggtga ccaactgcat ggagcatgcg ctgattgcct   1680

gccacccccg tactcgctac tcagctggct gggatgccaa gcttctctac ctccccatga   1740

gctacatgcc caccttcctg gtggatgcca ttatgtactg ggtctctcca agcccggcca   1800

aggctctatg aagctaaggt tggatgcatg gttgcatgga tttggggtgt gctatgaggg   1860

gtggtgtatc cttgggagag atataaagtg gagggaggga gccgtccggt cagtagggca   1920

ccaatcccac ctccttcatt acctcctggc catgattctc ctgggagata attctgctct   1980

ctggagatgt tggtaggaaa gtttcaagtt acgcagctga gaaacaggga ccaaatagtg   2040

ctcctgggtg cattgtcacc gtgggtggcc actcaagggt ccaagcctct agggccatcc   2100

ttgggctaac aactggggtg ggtgtgagca ggtggaagga gcctcagccc atgccattac   2160

ctcctgcttc cttatcaggc tgtgtgttaa ttctgggcca gtctacaccc tcccacgggg   2220

tggaaatggc ctggaggatg tgagggcacc cctcctctga agatccctgt acacgtggtg   2280

ttgggactgg aaccattatg cggccccata ggcctcagga gtcatcccag aagcagtggc   2340

tgggaggtgg tgtcctaagt aaggatctgt gcagaggaca aataaatcag tttttgattt   2400

gtctt                                                               2405
```

<210> SEQ ID NO 88
<211> LENGTH: 2137
<212> TYPE: DNA
<213> ORGANISM: Homo sapiens
<220> FEATURE:
<223> OTHER INFORMATION: hmft-0048

<400> SEQUENCE: 88

```
ctcgagagtt gccggggagg agcggagcgg tgcggaggct ctgctcggat cgaggtctgc     60

agcgcagctt cgggagcatg agtgctgcag tgactgcagg gaagctggca cgggcaccgg    120

ccgaccctgg gaaagccggg gtccccggag ttgcagctcc cggagctccg gcggcggctc    180

caccggcgaa agagatcccg gaggtcctag tggacccacg cagccggcgg cgctatgtgc    240

ggggccgctt tttgggcaag ggcggctttg ccaagtgctt cgagatctcg gacgcggaca    300

ccaaggaggt gttcgcgggc aagattgtgc ctaagtctct gctgctcaag ccgcaccaga    360

gggagaagat gtccatggaa atatccattc accgcagcct cgcccaccag cacgtcgtag    420

gattccacgg ctttttcgag gacaacgact tcgtgttcgt ggtgttggag ctctgccgcc    480

ggaggtctct cctggagctg cacaagagga ggaaagccct gactgagcct gaggcccgat    540

actacctacg gcaaattgtg cttggctgcc agtacctgca ccgaaaccga gttattcatc    600

gagacctcaa gctgggcaac cttttcctga atgaagatct ggaggtgaaa ataggggatt    660

ttggactggc aaccaaagtc gaatatgacg gggagaggaa gaagaccctg tgtgggactc    720

ctaattacat agctcccgag gtgctgagca agaaagggca cagtttcgag gtggatgtgt    780

ggtccattgg gtgtatcatg tataccttgt tagtgggcaa accacctttt gagacttctt    840

gcctaaaaga gacctacctc cggatcaaga agaatgaata cagtattccc aagcacatca    900

accccgtggc cgcctccctc atccagaaga tgcttcagac agatcccact gcccgcccaa    960

ccattaacga gctgcttaat gacgagttct ttacttctgg ctatatccct gcccgtctcc   1020

ccatcacctg cctgaccatt ccaccaaggt tttcgattgc tcccagcagc ctggacccca   1080

gcaaccggaa gcccctcaca gtcctcaata aaggcttgga gaacccccctg cctgagcgtc   1140

cccgggaaaa agaagaacca gtggttcgag agacaggtga ggtggtcgac tgccacctca   1200

gtgacatgct gcagcagctg cacagtgtca atgcctccaa gccctcggag cgtgggctgg   1260

tcaggcaaga ggaggctgag gatcctgcct gcatccccat cttctgggtc agcaagtggg   1320

tggactattc ggacaagtac ggccttgggt atcagctctg tgataacagc gtgggggtgc   1380

tcttcaatga ctcaacacgc ctcatcctct acaatgatgg tgacagcctg cagtacatag   1440

agcgtgacgg cactgagtcc tacctcaccg tgagttccca tcccaactcc ttgatgaaga   1500

agatcaccct ccttaaatat ttccgcaatt acatgagcga gcacttgctg aaggcaggtg   1560

ccaacatcac gccgcgcgaa ggtgatgagc tcgcccggct gccctaccta cggacctggt   1620

tccgcacccg cagcgccatc atcctgcacc tcagcaacgg cagcgtgcag atcaacttct   1680

tccaggatca caccaagctc atcttgtgcc cactgatggc agccgtgacc tacatcgacg   1740

agaagcggga cttccgcaca taccgcctga gtctcctgga ggagtacggc tgctgcaagg   1800

agctggccag ccggctccgc tacgcccgca ctatggtgga caagctgctg agctcacgct   1860

cggccagcaa ccgtctcaag gcctcctaat agctgccctc cctccggac tggtgccctc   1920

ctcactccca cctgcatctg gggcccatac tggttggctc ccgcggtgcc atgtctgcag   1980

tgtgcccccc agccccggtg gctgggcaga gctgcatcat ccttgcaggt gggggttgct   2040

gtataagtta tttttgtaca tgttcgggtg tgggttctac agccttgtcc ccctccccct   2100

caaccccacc atatgaattg tacagaatat ttctatt                            2137
```

<210> SEQ ID NO 89

-continued

<211> LENGTH: 3008
<212> TYPE: DNA
<213> ORGANISM: Homo sapiens
<220> FEATURE:
<223> OTHER INFORMATION: hmft-0306

<400> SEQUENCE: 89

```
cctgaatcct tggagactga catttttccc ccctaaaggc atagacaaca aaagaaattt     60

tattgagagg aaaacacaag tccttaaact gcaaagatgt ttgccaggat gtctgatctc    120

catgttctgc tgttaatggc tctggtggga aagacagcct gtgggttctc cctgatgtct    180

ttattggaaa gcctggaccc agactggacc cctgaccagt atgattacag ctacgaggat    240

tataatcagg aagagaacac cagtagcaca cttacccatg ctgagaatcc tgactggtac    300

tacactgagg accaagctga tccatgccag cccaacccct gtgaacacgg tggggactgc    360

ctcgtccatg ggagcacctt cacatgcagc tgcctggctc ctttctctgg gaataagtgt    420

cagaaagtgc aaaatacgtg caaggacaac ccatgtggcc ggggccaatg tctcattacc    480

cagagtcctc cctactaccg ctgtgtctgt aaacaccctt acacaggtcc cagctgctcc    540

caagtggttc ctgtatgcag gccaaacccc tgccagaatg gggctacctg ctcccggcat    600

aagcggagat ccaagttcac ctgtgcctgt cccgaccagt tcaaggggaa attctgtgaa    660

ataggttctg atgactgcta tgttggcgat ggctactctt accgagggaa aatgaatagg    720

acagtcaacc agcatgcgtg cctttactgg aactcccacc tcctcttgca ggagaattac    780

aacatgttta tggaggatgc tgaaacccat gggattgggg aacacaattt ctgcagaaac    840

ccagatgcgg acgaaaagcc ctggtgcttt attaaagtta ccaatgacaa ggtgaaatgg    900

gaatactgtg atgtctcagc ctgctcagcc caggacgttg cctacccaga ggaaagcccc    960

actgagccat caaccaagct tccggggttt gactcctgtg gaaagactga gatagcagag   1020

aggaagatca agagaatcta tggaggcttt aagagcacgg cgggcaagca cccatggcag   1080

gcgtccctcc agtcctcgct gcctctgacc atctccatgc cccagggcca cttctgtggt   1140

ggggcgctga tccacccctg ctgggtgctc actgctgccc actgcaccga cataaaaacc   1200

agacatctaa aggtggtgct aggggaccag gacctgaaga aagaagaatt tcatgagcag   1260

agctttaggg tggagaagat attcaagtac agccactaca atgaaagaga tgagattccc   1320

cacaatgata ttgcattgct caagttaaag ccagtggatg gtcactgtgc tctagaatcc   1380

aaatacgtga agactgtgtg cttgcctgat gggtcctttc cctctgggag tgagtgccac   1440

atctctggct ggggtgttac agaaacagga aaagggtccc gccagctcct ggatgccaaa   1500

gtcaagctga ttgccaacac tttgtgcaac tcccgccaac tctatgacca catgattgat   1560

gacagtatga tctgtgcagg aaatcttcag aaacctgggc aagacacctg ccagggtgac   1620

tctggaggcc ccctgacctg tgagaaggac ggcacctact acgtctatgg gatagtgagc   1680

tggggcctgg agtgtgggaa gaggccaggg gtctacaccc aagttaccaa attcctgaat   1740

tggatcaaag ccaccatcaa aagtgaaagt ggcttctaag gtactgtctt ctggacctca   1800

gagcccactc tccttggcac cctgacaccg ggaggcctca tggccaacaa tggacacctc   1860

cagagcctcc aggggaccac acagtagact atccctactc taagcagaga caactgccac   1920

ccagcctggg ccttcccaga ccagcatttg cacaatatca ccaggcttct tctgcctccc   1980

ttggtaaccc aaggaatgat ggaatcaaca caacatagta tgtttgcttt ccttacccaa   2040

ttgtaccttc tagaaaatca gtgttcacag agactgcctc caccacaggc atcctgcaaa   2100

tgcagactcc agaatcccca gcatcagcgg gaaccaccat cacatcttta ttcctcagcc   2160
```

```
cagacactcg aggcactcaa cagaatcagc catccacgtc taggtatcag agaggaccac   2220
aaatacaaca ttctccatct gctttcagag ttattatttt aataaaggaa gatctgggat   2280
gggctggtgg gccattccag cttgccgaaa tcaaagccat ctgaagcctg tctctggtga   2340
acaaacttcc tctctggcct ctcaggaatc agggtggcat ggctcacaac agcagggcct   2400
tcttcttttt gacgtgcaga atctcagtgg catctgggtt cacctcccca ctctgatgat   2460
ctccagcctc cactgcttct gccccccgct gctgaaatca aacataccccc aagttaaaat  2520
gaagctcccc cacccccact cccggccccg gttcccacag gacacgctaa gaagcacagg   2580
gagcatttaa caggctcacc ctccctttcc ttttcccctc ttctaccctc cccaagaaaa   2640
agggccttca aggcaggaat gagaaagcaa agccaatctc tcatttagac ctggcttctt   2700
tcttctgaac aaagtagggt tcaaaatgca gactgtcata tccagcgagt ccctgaccct   2760
ttctgcgaat gtaacgagca agcagtcagc acagcctggg ctgccctggc ccgggattga   2820
tgtagccccg gtaggtttgc ctctgcagaa ctaatggctg tgacttcaga gaagccctgc   2880
aggaagttta acctacgtgt catctgcctg gtcatctcag acccatgaaa ttaggcgcct   2940
tgtttgagct gcgtttcaca cttctttaga cgctagctga cctttggcca aaaataaact   3000
ttgaaaag                                                            3008
```

<210> SEQ ID NO 90
<211> LENGTH: 1850
<212> TYPE: DNA
<213> ORGANISM: Homo sapiens
<220> FEATURE:
<223> OTHER INFORMATION: hmft-0550

<400> SEQUENCE: 90

```
gccaggccga accgcagctt cttggcttag gtacttctac tcacagcggc cgattccgag     60
gccaactcca gcaatggctt ttgcaaatct gcggaaagtg ctcatcagtg acagcctgga    120
cccttgctgc cggaagatct tgcaagaggg agggctgcag gtggtggaaa agcagaacct    180
tagcaaagag gagctgatag cggagctgca ggactgtgaa ggccttattg ttcgctctgc    240
caccaaggtg accgctgatg tcatcaacgc agctgagaaa ctccaggtgg tgggcagggc    300
tggcacaggt gtggacaatg tggatctgga ggccgcaaca aggaagggca tcttggttat    360
gaacaccccc aatgggaaca gcctcagtgc cgcagaactc acttgtggaa tgatcatgtg    420
cctggccagg cagattcccc aggcgacggc ttcgatgaag gacggcaaat gggagcggaa    480
gaagttcatg ggaacagagc tgaatggaaa gaccctggga attcttggcc tgggcaggat    540
tgggagagag gtagctaccc ggatgcagtc ctttgggatg aagactatag ggtatgaccc    600
catcatttcc ccagaggtct cggcctcctt tggtgttcag cagctgcccc tggaggagat    660
ctggcctctc tgtgatttca tcactgtgca cactcctctc ctgccctcca cgacaggctt    720
gctgaatgac aacacctttg cccagtgcaa gaagggggtg cgtgtggtga actgtgcccg    780
tggagggatc gtggacgaag gcgccctgct ccgggccctg cagtctggcc agtgtgccgg    840
ggctgcactg gacgtgttta cggaagagcc gccacgggac cgggccttgg tggaccatga    900
gaatgtcatc agctgtcccc acctgggtgc cagcaccaag gaggctcaga gccgctgtgg    960
ggaggaaatt gctgttcagt tcgtggacat ggtgaagggg aaatctctca cgggggttgt   1020
gaatgcccag gcccttacca gtgccttctc tccacacacc aagccttgga ttggtctggc   1080
agaagctctg ggacactgat tgcgagcctg ggctgggtcc cccaaaggga ccatccaggt   1140
```

```
gataacacag ggaacatccc tgaagaatgc tgggaactgc ctaagccccg cagtcattgt   1200

cggcctcctg aaagaggctt ccaagcaggc ggatgtgaac ttggtgaacg ctaagctgct   1260

ggtgaaagag gctggcctca atgtcaccac ctcccacagc cctgctgcac caggggagca   1320

aggcttcggg gaatgcctcc tggccgtggc cctggcaggc gcccccttacc aggctgtggg   1380

cttggtccaa ggcactacac ctgtactgca ggggctcaat ggagctgtct tcaggccaga   1440

agtgcctctc cgcagggacc tgcccctgct cctattccgg actcagacct ctgaccctgc   1500

aatgctgcct accatgattg gcctcctggc agaggcaggc gtgcggctgc tgtcctacca   1560

gacttcactg gtgtcagatg gggagacctg gcacgtcatg ggcatctcct ccttgctgcc   1620

cagcctggaa gcgtggaagc agcatgtgac tgaagccttc cagttccact tctaaccttg   1680

gagctcactg gtccctgcct ctggggcttt tctgaagaaa cccacccact gtgatcaata   1740

gggagagaaa atccacattc ttgggctgaa cgcgggcctc tgacactgct tacactgcac   1800

tctgaccctg tagtacagca ataaccgtct aataaagagc ctaccccccaa              1850
```

```
<210> SEQ ID NO 91
<211> LENGTH: 1547
<212> TYPE: DNA
<213> ORGANISM: Homo sapiens
<220> FEATURE:
<223> OTHER INFORMATION: hmft-0609

<400> SEQUENCE: 91

gaaatctctt gattcctagt ctctcgatat ggcacctccg tcagtctttg ccgaggttcc     60

gcaggcccag cctgtcctgg tcttcaagct cactgccgac ttcagggagg atccggaccc    120

ccgcaaggtc aacctgggag tgggagcata tcgcacggat gactgccatc cctgggtttt    180

gccagtagtg aagaaagtgg agcagaagat tgctaatgac aatagcctaa atcacgagta    240

tctgccaatc ctgggcctgg ctgagttccg gagctgtgct tctcgtcttg cccttgggga    300

tgacagccca gcactcaagg agaagcgggt aggaggtgtg caatctttgg ggggaacagg    360

tgcacttcga attggagctg atttcttagc gcgttggtac aatggaacaa acaacaagaa    420

cacacctgtc tatgtgtcct caccaacctg ggagaatcac aatgctgtgt tttccgctgc    480

tggttttaaa gacattcggt cctatcgcta ctgggatgca gagaagagag gattggacct    540

ccagggcttc ctgaatgatc tggagaatgc tcctgagttc tccattgttg tcctccacgc    600

ctgtgcacac aacccaactg ggattgaccc aactccggag cagtggaagc agattgcttc    660

tgtcatgaag caccggtttc tgttcccctt ctttgactca gcctatcagg gcttcgcatc    720

tggaaacctg gagagagatg cctgggccat tcgctatttt gtgtctgaag gcttcgagtt    780

cttctgtgcc cagtccttct ccaagaactt cgggctctac aatgagagag tcgggaatct    840

gactgtggtt ggaaaagaac ctgagagcat cctgcaagtc ctttcccaga tggagaagat    900

cgtgcggatt acttggtcca atcccccgc ccagggagca cgaattgtgg ccagcaccct    960

ctctaaccct gagctctttg aggaatggac aggtaatgtg aagacaatgg ctgaccggat   1020

tctgaccatg agatctgaac tcagggcacg actagaagcc ctcaaaaccc ctgggacctg   1080

gaaccacatc actgatcaaa ttggcatgtt cagcttcact gggttgaacc ccaagcaggt   1140

tgagtatctg gtcaatgaaa agcacatcta cctgctgcca agtggtcgaa tcaacgtgag   1200

tggcttaacc accaaaaatc tagattacgt ggccacctcc atccatgaag cagtcaccaa   1260

aatccagtga agaaacacca cccgtccagt accaccaaag tagttctctg tcatgtgtgt   1320

tccctgcctg cacaaaccta catgtacata ccatggatta gagacacttg caggactgaa   1380
```

```
aggctgctct ggtgaggcag cctctgttta aaccggcccc acatgaagag aacatccctt   1440

gagacgaatt tggagactgg gattagagcc tttggaggtc aaagcaaatt aagattttta   1500

tttaagaata aaagagtact ttgatcatga aaaaaaaaaa aaaaaaa                 1547
```

<210> SEQ ID NO 92
<211> LENGTH: 2339
<212> TYPE: DNA
<213> ORGANISM: Homo sapiens
<220> FEATURE:
<223> OTHER INFORMATION: hmft-0716

<400> SEQUENCE: 92

```
aaaaaaataa tggcattatt tgggccactt ggaaaacccg gtggtattcc atgaagaaaa     60

ccactatgaa gataatccca ttcaccagac tcacaattgg agaaggacag caacaccacc    120

tggggggagc caaacaggct ggagacagaa actcccggtg tggcagctga gatggcccag    180

gaaagaacta tattaccttc aaaaagagag gtacatgcga tgtttgaggt ggcatgaagc    240

tcagtggtgt tatattggaa tgagtgagtg accatcctgg agccttcctg aaagaggatt    300

ggaacatcag ttaacatctg accactgcca gcgcaccccc tcccacccac gtcgattgca    360

tctctgggct ccagggataa agcaggtctt ggggtgcacc atgatttcac cattcttagt    420

actggccatt ggcacctgcc ttactaactc cttagtgcca gagaaagaga aagaccccaa    480

gtactggcga gaccaagcgc aagagacact gaaatatgcc ctggagcttc agaagctcaa    540

caccaacgtg gctaagaatg tcatcatgtt cctgggagat gggatgggtg tctccacagt    600

gacggctgcc cgcatcctca agggtcagct ccaccacaac cctggggagg agaccaggct    660

ggagatggac aagttcccct tcgtggccct ctccaagacg tacaacacca aagcccaggt    720

ccctgacagc gccggcaccg ccaccgccta cctgtgtggg gtgaaggcca atgagggcac    780

cgtgggggta agcgcagcca ctgagcgttc ccggtgcaac accacccagg ggaacgaggt    840

cacctccatc ctgcgctggg ccaaggacgc tgggaaatct gtgggcattg tgaccaccac    900

gagagtgaac catgccaccc ccagcgccgc ctacgcccac tcggctgacc gggactggta    960

ctcagacaac gagatgcccc ctgaggcctt gagccagggc tgtaaggaca tcgcctacca   1020

gctcatgcat aacatcaggg acattgacgt gatcatgggg ggtggccgga aatacatgta   1080

ccccaagaat aaaactgatg tggagtatga gagtgacgag aaagccaggg gcacgaggct   1140

ggacggcctg gacctcgttg acacctggaa gagcttcaaa ccgagacaca agcactccca   1200

cttcatctgg aaccgcacgg aactcctgac ccttgacccc cacaatgtgg actacctatt   1260

gggtctcttc gagccggggg acatgcagta cgagctgaac aggaacaacg tgacggaccc   1320

gtcactctcc gagatggtgg tggtggccat ccagatcctg cggaagaacc ccaaaggctt   1380

cttcttgctg gtggaaggag gcagaattga ccacgggcac catgaaggaa aagccaagca   1440

ggccctgcat gaggcggtgg agatggaccg ggccatcggg caggcaggca gcttgacctc   1500

ctcggaagac actctgaccg tggtcactgc ggaccattcc cacgtcttca catttggtgg   1560

atacaccccc cgtggcaact ctatctttgg tctggccccc atgctgagtg acacagacaa   1620

gaagcccttc actgccatcc tgtatggcaa tgggcctggc tacaaggtgg tgggcggtga   1680

acgagagaat gtctccatgg tggactatgc tcacaacaac taccaggcgc agtctgctgt   1740

gcccctgcgc cacgagaccc acggcgggga ggacgtggcc gtcttctcca agggccccat   1800

ggcgcacctg ctgcacggcg tccacgagca gaactacgtc ccccacgtga tggcgtatgc   1860
```

-continued

```
agcctgcatc ggggccaacc tcggccactg tgctcctgcc agctcggcag gcagccttgc   1920

tgcaggcccc ctgctgctcg cgctggccct ctacccccctg agcgtcctgt tctgagggcc   1980

cagggcccgg gcacccacaa gcccgtgaca gatgccaact tcccacacgg cagccccccc   2040

ctcaaggggc agggaggtgg gggcctcctc agcctctgca actgcaagaa aggggaccca   2100

ggaaaccaaa gtctgccgcc cacctcgctc ccctctggaa tcttccccaa gggccaaacc   2160

cacttctggc ctccagcctt tgctccctcc ccgctgccct ttggccaaca gggtagattt   2220

ctcttgggca ggcagagagt acagactgca gacattctca aagcctctta tttttctagc   2280

gaacgtattt ctccagaccc agaggccctg aagcctccgt ggaacattct ggatctgac    2339
```

```
<210> SEQ ID NO 93
<211> LENGTH: 1944
<212> TYPE: DNA
<213> ORGANISM: Homo sapiens
<220> FEATURE:
<223> OTHER INFORMATION: hmft-0844

<400> SEQUENCE: 93

aggccccgag aactgtcgcc cttcacgatg ttgctccgtg cctttatcct ggccactctc     60

tctgcttccg cggcttgggg gcatccgtcc tcgccacctg tggtggacac cgtgcatggc    120

aaagtgctgg ggaagttcgt cagcttagaa ggatttgcac agcctgtggc cattttcctg    180

ggaatccctt ttgccaagcc gcctcttgga cccctgaggt ttactccacc gcagcctgca    240

gaaccatgga gctttgtgaa gaatgccacc tcgtaccctc ctatgtgcac ccaagatccc    300

aaggcggggc agttactctc agagctattt acaaaccgaa aggagaacat tcctctcaag    360

ctttctgaag actgtcttta cctcaatatt tacactcctg ctgacttgac caagaaaaac    420

aggctgccgg tgatggtgtg gatccacgga gggggggctga tggtgggtgc ggcatcaacc    480

tatgatgggc tggcccttgc tgcccatgaa aacgtggtgg tggtgaccat tcaatatcgc    540

ctgggcatct ggggattctt cagcacaggg gatgaacaca gccgggggaa ctggggtcac    600

ctggaccagg tggctgccct gcgctgggtc caggacaaca ttgccagctt tggagggaac    660

ccaggctctg tgaccatctt tggagagtca gcgggaggag aaagtgtctc tgttcttgtt    720

ttgtctccat tggccaagaa cctcttccac cgggccattt ctgagagtgg cgtggccctc    780

acttctgttc tggtgaagaa aggtgatgtc aagcccttgg ctgagcaaat tgctatcact    840

gctgggtgca aaaccaccac ctctgctgtc atggttcact gcctgcgaca gaagacggaa    900

gaggagctct tggagacgac attgaaaatg aaattcttat ctctggactt acagggagac    960

cccagagaga gtcaacccct tctgggcact gtgattgatg ggatgctgct gctgaaaaca   1020

cctgaagagc ttcaagctga aaggaatttc cacactgtcc cctacatggt cggaattaac   1080

aagcaggagt ttggctggtt gattccaatg cagttgatga gctatccact ctccgaaggg   1140

caactggacc agaagacagc catgtcactc ctgtggaagt cctatcccct tgtttgcatt   1200

gctaaggaac tgattccaga agccactgag aaatacttag gaggaacaga cgacactgtc   1260

aaaaagaaag acctgttcct ggacttgata gcagatgtga tgtttggtgt cccatctgtg   1320

attgtggccc ggaaccacag agatgctgga gcacccacct acatgtatga gtttcagtac   1380

cgtccaagct tctcatcaga catgaaaccc aagacggtga taggagacca cggggatgag   1440

ctcttctccg tctttggggc ccccattttta aaagagggtg cctcagaaga ggagatcaga   1500

cttagcaaga tggtgatgaa attctgggcc aactttgctc gcaatggaaa ccccaatggg   1560

gaagggctgc cccactggcc agagtacaac cagaaggaag ggtatctgca gattggtgcc   1620
```

-continued

```
aacacccagg cggcccagaa gctgaaggac aaagaagtag ctttctggac caacctcttt   1680
gccaagaagg cagtggagaa gccaccccag acagaacaca tagagctgtg aatgaagatc   1740
cagccggcct tgggagcctg gaggagcaaa gactggggtc ttttgcgaaa gggattgcag   1800
gttcagaagg catcttacca tggctgggga attgtctggt ggtgggggc aggggacaga   1860
ggccatgaag gagcaagttt tgtatttgtg acctcagctt tgggaataaa ggatcttttg   1920
aaggccaaaa aaaaaaaaaa aaaa                                          1944
```

<210> SEQ ID NO 94
<211> LENGTH: 2694
<212> TYPE: DNA
<213> ORGANISM: Homo sapiens
<220> FEATURE:
<223> OTHER INFORMATION: hmft-1154

<400> SEQUENCE: 94

```
ccctaggaca cctttctaaa aagactccct gtggtgttca gaatcactcc tacagtcagg     60
ttctccacaa tggatctcag tgctgcaagt caccgcatac ctctaagtga tggaaacagc    120
attcccatca tcggacttgg tacctactca gaacctaaat cgacccctaa gggagcctgt    180
gcaacatcgg tgaaggttgc tattgacaca gggtaccgac atattgatgg ggcctacatc    240
taccaaaatg aacacgaagt tggggaggcc atcagggaga agatagcaga aggaaaggtg    300
cggagggaag atatcttcta ctgtggaaag ctatgggcta caaatcatgt cccagagatg    360
gtccgcccaa ccctggagag gacactcagg gtcctccagc tagattatgt ggatctttac    420
atcattgaag tacccatggc ctttaagcca ggagatgaaa tataccctag agatgagaat    480
ggcaaatggt tatatcacaa gtcaaatctg tgtgccactt gggaggcgat ggaagcttgc    540
aaagacgctg gcttggtgaa atccctggga gtgtccaatt ttaaccgcag gcagctggag    600
ctcatcctga acaagccagg actcaaacac aagccagtca gcaaccaggt tgagtgccat    660
ccgtatttca cccagccaaa actcttgaaa ttttgccaac aacatgacat tgtcattact    720
gcatatagcc ctttggggac cagtaggaat ccaatctggg tgaatgtttc ttctccacct    780
ttgttaaagg atgcacttct aaactcattg gggaaaaggt acaataagac agcagctcaa    840
attgttttgc gtttcaacat ccagcgaggg gtggttgtca ttcctaaaag ctttaatctt    900
gaaaggatca aagaaaattt tcagatcttt gacttttctc tcactgaaga agaaatgaag    960
gacattgaag ccttgaataa aaatgtccgc tttgtagaat tgctcatgtg gcgcgatcat   1020
cctgaatacc catttcatga tgaatactga ctgccgggag ttcctgaaca gatttttcac   1080
tcccatgagt gccaagacgg tgcaatgggt agtcccctag atgtgaaaat gaagagagag   1140
ggttttacca tcctgagaag aaataatgat ggaaacatgt ttaatgtttg tgcagtgtaa   1200
atgactttga ctcagtcaca ttgaagtaaa aatattaaaa tctgttgaaa taactcttag   1260
gaaattatca actaattttt tcagatcagt atcttctaga ttccagacag aaaaaaatta   1320
cacttcagaa aagacatcaa aggcaacata tgacaacaag taatttatga atctgggtag   1380
tagcgttggt aatctgagtt ctttaagggt tcacaggaca acgaagtgca tgtggcagtg   1440
tgctggcagt ggccttgagg ctttggacca ttggttacaa aacagacaca gccaagataa   1500
gatccacaca cacattatta acaaggaagt gatttgctgc accttgagtt gagaggacta   1560
catgtagaaa agtcttaaaa tagagctaaa caccacagtg gtcaacaaag ccatcataat   1620
gttggtgttt gtttccctcc aatgtatgta tgtttagttt ttatccaacc tgaggaatga   1680
```

-continued

```
aaacttaact ggatctctct tgcatcctta aagggcctga gtctcaacat ggctgctgat   1740

ccatacttac acatcttact gtcaatcttg cctacattga ttatagaacc actattacgt   1800

gaaaaggctt gaaacaacca acatatacaa ataaaaccct gccttgtaaa atagtaaaag   1860

agaagccata tattggcttt tcttcttaac ttgggagata tattgaaaca aggtgcttta   1920

taagattatt gtacttaaga ctttaatagt gttacttgga tagcttatat gaattttgag   1980

aattttatat gaattttgag aaagcaagtt caaaagaact ctggtaattt tcctgtatgt   2040

acaatttaaa gagtgaataa gattattaga attcagcaat agagatatat ctattttcaa   2100

ttcaactaca gaaatatatt ttattggccg ggtgcggtgg ctcatgccta taatcccagc   2160

actttgggag gccaaggtgg gcagatcagg aggtcaggag atcgagacca tcttggctaa   2220

caaggtgaaa ccccgtctct actaaaaata caaaaaatta gccaggcgcg gtggcggggg   2280

cctgtaatcc cagctactca ggaggctgag gcagaagaat ggcatgaacc cgggaggagg   2340

agcttgcagt gagccgagat agcgccactg cagtccggcc tgggtgaaag agcgagactc   2400

cgtctcaaaa acaaaaaaaa aaaagaaaag aaatatattt tattcattca cattaggtca   2460

ctgtcatact gtcataggct gagagagttc ttcaaaaatt atgttttccc aagatcagtt   2520

gcttatagat aatgttcaat gacctcaaga catatatttt tgagaaatta tcattttaaa   2580

aaatttggtc tatactgatt gttttcactg attccaatat tattacttat aacactgacc   2640

tctggaaaat attttgttca caagaaataa taaagtataa tgatttgttg catc         2694
```

<210> SEQ ID NO 95
<211> LENGTH: 634
<212> TYPE: DNA
<213> ORGANISM: Homo sapiens
<220> FEATURE:
<223> OTHER INFORMATION: hmft-1198

<400> SEQUENCE: 95

```
cggctgagag gcagcgaact catctttgcc agtacaggag cttgtgccgt ggcccacagc     60

ccacagccca cagccatggg ctgggacctg acggtgaaga tgctggcggg caacgaattc    120

caggtgtccc tgagcagctc catgtcggtg tcagagctga aggcgcagat cacccagaag    180

attggcgtgc acgccttcca gcagcgtctg gctgtccacc cgagcggtgt ggcgctgcag    240

gacagggtcc cccttgccag ccagggcctg ggccctggca gcacggtcct gctggtggtg    300

gacaaatgcg acgaacctct gagcatcctg gtgaggaata acaagggccg cagcagcacc    360

tacgaggtcc ggctgacgca gaccgtggcc cacctgaagc agcaagtgag cgggctggag    420

ggtgtgcagg acgacctgtt ctggctgacc ttcgagggga agcccctgga ggaccagctc    480

ccgctggggg agtacggcct caagcccctg agcaccgtgt tcatgaatct gcgcctgcgg    540

ggaggcggca cagagcctgg cgggcggagc taagggcctc caccagcatc cgagcaggat    600

caagggccgg aaataaaggc tgttgtaaga gaat                                634
```

<210> SEQ ID NO 96
<211> LENGTH: 614
<212> TYPE: DNA
<213> ORGANISM: Homo sapiens
<220> FEATURE:
<223> OTHER INFORMATION: hmft-1264

<400> SEQUENCE: 96

```
tatagctcca cggccagaag ataccagcag ctctgccttt actgaaattt cagctggaga     60

aaggtccaca gcacaatgag gcttttcaca ggcattgttt tctgctcctt ggtcatggga    120
```

```
gtcaccagtg aaagctggcg ttcgtttttc aaggaggctc tccaaggggt tggggacatg    180

ggcagagcct attgggacat aatgatatcc aatcaccaaa attcaaacag atatctctat    240

gctcggggaa actatgatgc tgcccaaaga ggacctgggg gtgtctgggc tgctaaactc    300

atcagccgtt ccagggtcta tcttcaggga ttaatagact actatttatt tggaaacagc    360

agcactgtat tggaggactc gaagtccaac gagaaagctg aggaatgggg ccggagtggc    420

aaagaccccg accgcttcag acctgacggc ctgcctaaga aatactgagc ttcctgctcc    480

tctgctctca gggaaactgg gctgtgagcc acacacttct ccccccagac agggacacag    540

ggtcactgag ctttgtgtcc ccaggaactg gtatagggca cctagaggtg ttcaataaat    600

gtttgtcaaa ttga                                                      614
```

```
<210> SEQ ID NO 97
<211> LENGTH: 1645
<212> TYPE: DNA
<213> ORGANISM: Homo sapiens
<220> FEATURE:
<223> OTHER INFORMATION: hmft-1599

<400> SEQUENCE: 97

ggacttctag cccctgaact ttcagccgaa tacatctttt ccaaaggagt gaattcaggc     60

ccttgtatca ctggcagcag gacgtgacca tggagaagct gttgtgtttc ttggtcttga    120

ccagcctctc tcatgctttt ggccagacag acatgtcgag gaaggctttt gtgtttccca    180

aagagtcgga tacttcctat gtatccctca aagcaccgtt aacgaagcct ctcaaagcct    240

tcactgtgtg cctccacttc tacacggaac tgtcctcgac ccgtgggtac agtattttct    300

cgtatgccac caagagacaa gacaatgaga ttctcatatt ttggtctaag gatataggat    360

acagttttac agtgggtggg tctgaaatat tattcgaggt tcctgaagtc acagtagctc    420

cagtacacat ttgtacaagc tgggagtccg cctcagggat cgtggagttc tgggtagatg    480

ggaagcccag ggtgaggaag agtctgaaga agggatacac tgtgggggca gaagcaagca    540

tcatcttggg gcaggagcag gattccttcg gtgggaactt tgaaggaagc cagtccctgg    600

tgggagacat tggaaatgtg aacatgtggg actttgtgct gtcaccagat gagattaaca    660

ccatctatct tggcgggccc ttcagtccta atgtcctgaa ctggcgggca ctgaagtatg    720

aagtgcaagg cgaagtgttc accaaacccc agctgtggcc ctgaggccca gctgtgggtc    780

ctgaaggtac ctcccggttt tttacaccgc atgggcccca cgtctctgtc tctggtacct    840

cccgcttttt tacactgcat ggttcccacg tctctgtctc tgggcctttg ttcccctata    900

tgcattgcag gcctgctcca ccctcctcag cgcctgagaa tggaggtaaa gtgtctggtc    960

tgggagctcg ttaactatgc tgggaaacgg tccaaaagaa tcagaatttg aggtgttttg   1020

ttttcatttt tatttcaagt tggacagatc ttggagataa tttcttacct cacatagatg   1080

agaaaactaa cacccagaaa ggagaaatga tgttataaaa aactcataag gcaagagctg   1140

agaaggaagc gctcatcttc tatttaattc cccacccatg acccccagaa agcaggaggg   1200

cattgcccac attcacaggg ctcttcagtc tcagaatcag gacactggcc aggtgtctgg   1260

tttgggtcca gagtgctcat catcatgtca tagaactgct gggcccaggt ctcctgaaat   1320

gggaagccca gcaataccac gcagtccctc cactttctca aagcacactg gaaaggccat   1380

tagaattgcc ccagcagagc agatctgctt tttttccaga gcaaaatgaa gcactaggta   1440

taaatatgtt gttactgcca agaacttaaa tgactggttt ttgtttgctt gcagtgcttt   1500
```

-continued

```
cttaatttta tggctcttct gggaaactcc tccccttttc cacacgaacc ttgtggggct   1560

gtgaattctt tcttcatccc cgcattccca atatacccag gccacaagag tggacgtgaa   1620

ccacagggtg gccgtgcggc acgag                                         1645
```

<210> SEQ ID NO 98
<211> LENGTH: 1580
<212> TYPE: DNA
<213> ORGANISM: Homo sapiens
<220> FEATURE:
<223> OTHER INFORMATION: hmft-1603

<400> SEQUENCE: 98

```
aaagaaggca tccagcaaga actgcacaag aaacggagtc agccggagaa caaggagtgg     60

tcttccactg cctcacagga ggatggaggc ccacaacgcg tctgccccat tcaacttcac    120

cctgccaccc aactttggca agcgccccac agacctggca ctgagcgtca tcctggtgtt    180

catgttgttc ttcatcatgc tctcgctggg ctgcaccatg gagttcagca agatcaaggc    240

tcacttatgg aagcctaaag ggctggccat cgccctggtg gcacagtatg gcatcatgcc    300

cctcacggcc tttgtgctgg gcaaggtctt ccggctgaag aacattgagg cactggccat    360

cttggtctgt ggctgctcac ctggagggaa cctgtccaat gtcttcagtc tggccatgaa    420

gggggacatg aacctcagca ttgtgatgac cacctgctcc accttctgtg cccttggcat    480

gatgcctctc ctcctgtaca tctactccag gggggatctat gatggggacc tgaaggacaa    540

ggtgccctat aaaggcatcg tgatatcact ggtcctggtt ctcattcctt gcaccatagg    600

gatcgtcctc aaatccaaac ggccacaata catgcgctat gtcatcaagg gagggatgat    660

catcattctc ttgtgcagtg tggccgtcac agttctctct gccatcaatg tggggaagag    720

catcatgttt gccatgacac cactcttgat tgccacctcc tccctgatgc cttttattgg    780

ctttctgctg ggttatgttc tctctgctct cttctgcctc aatggacggt gcagacgcac    840

tgtcagcatg gagactggat gccaaaatgt ccaactctgt tccaccatcc tcaatgtggc    900

ctttccacct gaagtcattg gaccactttt cttctttccc ctcctctaca tgattttcca    960

gcttggagaa gggcttctcc tcattgccat attttggtgc tatgagaaat tcaagactcc   1020

caaggataaa acaaaaatga tctacacagc tgccacaact gaagaaacaa ttccaggagc   1080

tctgggaaat ggcacctaca aaggggagga ctgctcccct tgcacagcct agcccttccc   1140

ctggtggcct ggattctggt cccaaagcaa ttctgaaagc cagtgtggta aactagagag   1200

agcagcaaaa acaccagtct tgcctgagtc tttctccagc atttccagta catctatcag   1260

aatcatcaag tcttggccgg gaacacagac agggtgtcta cccaagaagc ctcacctatc   1320

cccaacttag aatttgctac ttattttaaa gacttgttca gtgactgtaa actctatgaa   1380

accagaaacc gaatctgcct cttgctggga tctctaaaag tgtctgataa gcatcttaaa   1440

gtcactcaat tcctgaacta atcaatatat atgtttaacc cattactcaa atacccaaat   1500

cccattccaa gttttgtgac ccaaaagaga aataaatgct cacaagtgct gtagaattaa   1560

acttcagaag ttctaacctt                                               1580
```

<210> SEQ ID NO 99
<211> LENGTH: 1599
<212> TYPE: DNA
<213> ORGANISM: Homo sapiens
<220> FEATURE:
<223> OTHER INFORMATION: hyst-0078

<400> SEQUENCE: 99

-continued

```
cactgcttat taaagtacac tattcaggca tatcatgtag gtttactttc tgtgtttcta     60
gagaccaaga agcgggacgt tcaccatggg aagaaaatcg ctgtaccttc tgattgtggg    120
gatcctcata gcatattata tttatacgcc tctcccagat aacgttgagg agccatggag    180
aatgatgtgg ataaacgcac atctgaaaac tatacaaaat ttggctacat ttgtggagct    240
ccatgggagt tccattttta tggattcctt taaggttgtc gggagctttg atgaagtccc    300
accaacctca gatgaaaatg tcactgtgac tgagacaaaa ttcaacaaca ttcttgttcg    360
ggtatatgtg ccaaagagaa agtctgaagc actaagaagg gggttgtttt acatccatgg    420
tggaggctgg tgcgtgggaa gtgctgctct aagtggttat gacttgctgt caagatggac    480
agcagacaga cttgatgctg tcgtcgtatc aaccaactac agattagcac ctaagtatca    540
tttcccaatt caatttgaag atgtatataa tgccttaagg tggttcttac gtaaaaaagt    600
tcttgcaaaa tatggtgtga accctgagag aatcggtatt tctggagata gtgcaggagg    660
gaatttagct gcagcagtga ctcaacagct ccttgatgac ccagatgtca agatcaaact    720
caagatccag tctttaattt atcctgccct tcagcctctt gatgtagatt taccgtcata    780
tcaagaaaat tcaaattttc tatttctatc caaatcactc atggtcagat tctggagtga    840
atattttacc actgatagat cacttgaaaa agccatgctt tccagacaac atgtacctgt    900
ggaatcaagt catctcttca aatttattaa ttggagttcc ctgctccctg agaggtttat    960
aaaaggacat gtttataaca atccaaatta tggcagttct gagctggcta aaaaatatcc   1020
agggttccta gatgtgaggg cagccccttt gttggctgat gacaacaaat tacgtggctt   1080
acccctgacc tatgtcatca cctgtcaata tgatctctta agagatgatg gactcatgta   1140
tgtcacccga cttcgcaaca ctggggttca ggtgactcat aaccatgttg aggatggatt   1200
ccatggagca ttttcatttc tgggacttaa aattagtcac agacttataa atcagtatat   1260
tgagtggcta aaggaaaatc tatagtaaaa catgtagcta taacatattt taaaaataaa   1320
atctgaaaac ctcagaaaat ttcgattaga aattggtctt tcttagaatg gtctagttaa   1380
gttccacatg tagcataatt cttaaatagg cacttttctg tttttttttt cttactgtgg   1440
gatttcattt caattttcta cattgtctat ctgcttttc ggagatttc cttcttacac     1500
tgttaatctt attttaaaaa atattacatt cttgtatact ttatttttgt gagttggcta   1560
ctatttacga tgcaagagaa taaatgtgag caaagattg                           1599
```

<210> SEQ ID NO 100
<211> LENGTH: 1582
<212> TYPE: DNA
<213> ORGANISM: Homo sapiens
<220> FEATURE:
<223> OTHER INFORMATION: hyst-2010

<400> SEQUENCE: 100

```
cagagcggag acttcaggga gaccagagcc cagttgcagg cactcagcta gaagccctgc     60
catggcaccc ctgagacccc ttctcatact ggccctgctg gcatgggttg ctctggctga    120
ccaagagtca tgcaagggcc gctgcactga gggcttcaac gtggacaaga agtgccagtg    180
tgacgagctc tgctcttact accagagctg ctgcacagac tatacggctg agtgcaagcc    240
ccaagtgact cgcggggatg tgttcactat gccggaggat gagtacacgg tctatgacga    300
tggcgaggag aaaaacaatg ccactgtcca tgaacaggtg gggggcccct ccctgacctc    360
tgacctccag gcccagtcca aagggaatcc tgagcagaca cctgttctga aacctgagga    420
```

```
agaggcccct gcgcctgagg tgggcgcctc taagcctgag gggatagact caaggcctga    480

gacccttcat ccagggagac ctcagccccc agcagaggag gagctgtgca gtgggaagcc    540

cttcgacgcc ttcaccgacc tcaagaacgg ttccctcttt gccttccgag ggcagtactg    600

ctatgaactg gacgaaaagg cagtgaggcc tgggtacccc aagctcatcc gagatgtctg    660

gggcatcgag ggccccatcg atgccgcctt cacccgcatc aactgtcagg ggaagaccta    720

cctcttcaag ggtaatcagt actggcgctt tgaggatggt gtcctggacc ctgattaccc    780

ccgaaatatc tctgacggct tcgatggcat cccggacaac gtggatgcag ccttggccct    840

ccctgcccat agctacagtg gccgggagcg ggtctacttc ttcaagggga aacagtactg    900

ggagtaccag ttccagcacc agcccagtca ggaggagtgt gaaggcagct ccctgtcggc    960

tgtgtttgaa cactttgcca tgatgcagcg ggacagctgg gaggacatct tcgagcttct   1020

cttctggggc agaacctctg ctggtaccag acagccccag ttcattagcc gggactggca   1080

cggtgtgcca gggcaagtgg acgcagccat ggctggccgc atctacatct caggcatggc   1140

accccgcccc tccttgacca agaaacaaag gtttaggcat cgcaaccgca aaggctaccg   1200

ttcacaacga ggccacagcc gtggccgcaa ccagaactcc cgccggccat cccgcgccat   1260

gtggctgtcc ttgttctcca gtgaggagag caacttggga gccaacaact atgatgacta   1320

caggatggac tggcttgtgc ctgccacctg tgaacccatc cagagtgtct tcttcttctc   1380

tggagacaag tactaccgag tcaatcttcg cacacggcga gtggacactg tggaccctcc   1440

ctacccacgc tccatcgctc actactggct gggctgccca gctcctggcc atctgtagga   1500

gtcagagccc acatggccgg gccctctgta gctccctcct cccatctcct tcccccagcc   1560

caataaaggt cccttagccc cg                                            1582
```

```
<210> SEQ ID NO 101
<211> LENGTH: 2952
<212> TYPE: DNA
<213> ORGANISM: Homo sapiens
<220> FEATURE:
<223> OTHER INFORMATION: hyst-2465

<400> SEQUENCE: 101
```

```
gccaaaatga agaccctctc ccctactggc tacggccttc tgctggtcct gcccttgctg     60

ctggctgtcc ttcagagcac cacggcccac aagaatgaca tcaacatcta cagtctcacc    120

gtggactcca aggtctcgtc ccgatttgcc cacacagtcg ttaccagccg agtggtcaac    180

aagggcagtg ctgtgcagga ggccaccttc cagatggagc tgcccaagaa ggctttcatc    240

accaacttct ccatgatcat cgatggtgtg acctacccag gtaacatcaa ggagaaggct    300

gcagcccagg agcagtacag cgccgtggcc aggggagaga gtgctggcct tgtcagggcc    360

actgggagaa agacagagca gttccaggtg gcagtcagcg tggctcctgc tgccaaggtc    420

accttcgagc tggtgtatga ggagcttctg gcacggcatc tgggagttta tgagctgctg    480

ttgaaaatcc agccccagca gctggtcaag cacctgcaga tggacattca catcttcgag    540

cctcagggca tcagctttct ggagacagag agcaccttta tgaccaatga actggcagag    600

gccctcacca tatcacagaa caagactaag gctcacatcc gattcaagcc gacactctcc    660

cagcagcaga agtccccaga gcagcaggaa acagtcctgg atggcaactt catcgtccgc    720

tatgatgtga accggacagt cactgggggt tccattcaga tcgagaatgg ctactttgtg    780

cattactttg ccccggaggt ctggtctgca atacccaaga acgtgatctt tgtcattgac    840
```

-continued

```
acgagcggct ccatgagggg caggaaaatc cagcagaccc gggaagccct aattaagatc    900
ctgggtgacc tcggctcccg cgaccagttc aaccttgtca gcttcagtgg ggaagcaccc    960
aggagaaggg ctgttgcagc ctcagctgag aacgtggagg aagccaagag ctatgctgcc   1020
gaaatccatg cccagggagg gaccaatata aatgatgcga tgctgatggc cgtgcagctg   1080
ctggaaagag ccaaccggga ggagctgctg cccgcgagga gcgttacctt catcatcctc   1140
ctcaccgatg gcgaccctac tgtgggggag accaacccct cgaagatcca gaagaacgtt   1200
cgggaagcca tagacggcca gcacagcctc ttctgcctgg gcttcggctt tgacgtcccc   1260
tacgccttcc tggagaagat ggcactggag aatggcggtc tggcccggcg catctatgag   1320
gactctgact ctgccctgca gctcgaggac ttctaccagg aggtggccaa cccactgctg   1380
aggttggtgg cctttgagta cccaagcaat gccgtggagg aggtcacgca ggacaacttc   1440
cggctgttct tcaaaggctc tgagttggtg gtggccggga agctccggga ccagagcccc   1500
gatgtgctct ccgccaaagt caggggggcaa ctgcacatgg agaatgtcac cttcgtaatg   1560
gagtccaggg tagcagagca ggaggcggag ttcctgagcc ccaagtacat cttccacagc   1620
ttcatggaga gactctgggc atacctgacc atccagcaac tgttggcgca aacagtctct   1680
gcgtcagatg ctgagaagaa ggcccttgaa gcccgagccc tgagcttgtc actcaactac   1740
agctttgtca cccctctcac atctatggtg atcaccaaac ctgaaggcca agaacagtct   1800
caggttgctg agaagcccgt ggaaaatgga aaccgacagg ggaacaccca ctcaggtcac   1860
tcttcctttc aatttcattc tgtgggagac agaacatcca gactaacagg aggcagcagt   1920
gtagaccctg ttttttctca cagaagaggc tggaaaggac aagcccaagg ttttgagaaa   1980
atgtcctacc tcccaccgag attaggaccc cccggacctc ttcagcctac tcgtttttct   2040
catccgtttt cccgtataac cttggaccgg gtgctgccag aggtgctatc cgttcctgat   2100
gaaacgtcac atgacatgga ttcaagaatc ataggagcca cgatacctcc acccccctgcc   2160
cgcatccagg ctccttccgt catcttgcca ctgcctgggc agagcgtgga ccagctctgt   2220
gtggacctca agcactccca gggcccagtg aagctgctct cagaccctgg ccaaggggtt   2280
gaagtgactg gccactatga gagggagaag gcccgcttct catggattga agtgaccttc   2340
aagcacccgc cactgcaggt tcgtgcatcc ctggagcaca tagtagtgat tcggaaccgc   2400
caaagctctg cgtacaagtg gaaggaaaca ctctactcag tgatgcccgg cctcaagata   2460
accatggaca aggcgggact tcttctgctc agcagcccaa acagagtgac catcggcctg   2520
ctgtcctggg atggccctgg gaaggggctc cgactccttc tgcgggacac tgaccacttc   2580
tccagccaga tcagtgggac ctttggccag ttttaccagg acgtggtctg ggaccccca   2640
gcagcagcag atgacagcaa gcgaacagtg acagtccagg gacatgacca ctctgccacc   2700
agagagctca agctggatta ccaagaggga tccccgggaa aagagatttc ctgctggact   2760
gtggtgctgt agttctgatg ggaggagtta cacccgcccc ccatgctgcc cccttttttgc   2820
agatggctgc cacactgtaa cacaggtcag cctgtgggcc ctggaacatc atggggagat   2880
gtattttcac tcattaaaat aaagagaggt gatgtgaaaa aaaaaaaaaa aaaaaaaaaa   2940
aaaaaaaaaa aa                                                       2952
```

<210> SEQ ID NO 102
<211> LENGTH: 2137
<212> TYPE: DNA

<213> ORGANISM: Homo sapiens
<220> FEATURE:
<223> OTHER INFORMATION: Plk-1

<400> SEQUENCE: 102

```
ctcgagagtt gccggggagg agcggagcgg tgcggaggct ctgctcggat cgaggtctgc      60
agcgcagctt cgggagcatg agtgctgcag tgactgcagg gaagctggca cgggcaccgg     120
ccgaccctgg gaaagccggg gtccccggag ttgcagctcc cggagctccg gcggcggctc     180
caccggcgaa agagatcccg gaggtcctag tggacccacg cagccggcgg cgctatgtgc     240
ggggccgctt tttgggcaag ggcggctttg ccaagtgctt cgagatctcg gacgcggaca     300
ccaaggaggt gttcgcgggc aagattgtgc ctaagtctct gctgctcaag ccgcaccaga     360
gggagaagat gtccatggaa atatccattc accgcagcct cgcccaccag cacgtcgtag     420
gattccacgg ctttttcgag gacaacgact tcgtgttcgt ggtgttggag ctctgccgcc     480
ggaggtctct cctggagctg cacaagagga ggaaagccct gactgagcct gaggcccgat     540
actacctacg gcaaattgtg cttggctgcc agtacctgca ccgaaaccga gttattcatc     600
gagacctcaa gctgggcaac cttttcctga atgaagatct ggaggtgaaa ataggggatt     660
ttggactggc aaccaaagtc gaatatgacg gggagaggaa gaagaccctg tgtgggactc     720
ctaattacat agctcccgag gtgctgagca agaaagggca cagtttcgag gtggatgtgt     780
ggtccattgg gtgtatcatg tataccttgt tagtgggcaa accacctttt gagacttctt     840
gcctaaaaga gacctacctc cggatcaaga agaatgaata cagtattccc aagcacatca     900
accccgtggc cgcctccctc atccagaaga tgcttcagac agatcccact gcccgcccaa     960
ccattaacga gctgcttaat gacgagttct ttacttctgg ctatatccct gcccgtctcc    1020
ccatcacctg cctgaccatt ccaccaaggt tttcgattgc tcccagcagc ctggacccca    1080
gcaaccggaa gcccctcaca gtcctcaata aaggcttgga gaacccccctg cctgagcgtc    1140
cccgggaaaa agaagaacca gtggttcgag agacaggtga ggtggtcgac tgccacctca    1200
gtgacatgct gcagcagctg cacagtgtca atgcctccaa gccctcggag cgtgggctgg    1260
tcaggcaaga ggaggctgag gatcctgcct gcatccccat cttctgggtc agcaagtggg    1320
tggactattc ggacaagtac ggccttgggt atcagctctg tgataacagc gtgggggtgc    1380
tcttcaatga ctcaacacgc ctcatcctct acaatgatgg tgacagcctg cagtacatag    1440
agcgtgacgg cactgagtcc tacctcaccg tgagttccca tcccaactcc ttgatgaaga    1500
agatcaccct ccttaaatat ttccgcaatt acatgagcga gcacttgctg aaggcaggtg    1560
ccaacatcac gccgcgcgaa ggtgatgagc tcgcccggct gccctaccta cggacctggt    1620
tccgcacccg cagcgccatc atcctgcacc tcagcaacgg cagcgtgcag atcaacttct    1680
tccaggatca caccaagctc atcttgtgcc cactgatggc agccgtgacc tacatcgacg    1740
agaagcggga cttccgcaca taccgcctga gtctcctgga ggagtacggc tgctgcaagg    1800
agctggccag ccggctccgc tacgcccgca ctatggtgga caagctgctg agctcacgct    1860
cggccagcaa ccgtctcaag gcctcctaat agctgccctc cctccggac tggtgccctc    1920
ctcactccca cctgcatctg gggcccatac tggttggctc ccgcggtgcc atgtctgcag    1980
tgtgcccccc agccccggtg gctgggcaga gctgcatcat ccttgcaggt gggggttgct    2040
```

gtataagtta tttttgtaca tgttcgggtg tgggttctac agccttgtcc ccctcccccct 2100 caaccccacc atatgaattg tacagaatat ttctatt 2137

<210> SEQ ID NO 103
<211> LENGTH: 531
<212> TYPE: DNA
<213> ORGANISM: Homo sapiens
<220> FEATURE:
<223> OTHER INFORMATION: hmfn-0839-f

<400> SEQUENCE: 103
ttgggatcag tttgctggtt ataggaacta cactggttgg gcagctgcca gacagcagcc 60
tcaaaaactg gctgagtgaa ctggtccatc tgacttgctg ccggatctgt gtgcgagccc 120
tctctggtac cattcattat cataacaagc agtacagacc ccagaaggga ggcatttgtg 180
ttgccaacca tacttccccc attgatgttt taatcttgac aacggatgga tgttatgcta 240
tggttggcca ggttcatggc ggcttgatgg gaattattca gagagctatg gtcaaggctt 300
gtcctcatgt ctggtttgaa cgctcagaaa tgaaggatcg acacctggtt actaagagac 360
taaaagaaca tattgctgat aagaagaaac tacccatact aatttttcct gaaggaactt 420
gcatcaacaa tacttcagtc atgatgttta aaaaggggag ctttgaaatt ggaggaacca 480
tacatccagt tgcaattaag tataaccctc agttcggtga tgcattttgg a 531

<210> SEQ ID NO 104

<211> LENGTH: 607
<212> TYPE: DNA
<213> ORGANISM: Homo sapiens
<220> FEATURE:
<223> OTHER INFORMATION: hmfn-0839-r

<400> SEQUENCE: 104
tgtggccttt tttttttttt ttttagaaat atagaattta tttatattca taagacagtt 60
tcacattctg tacatggtta ccagaacaga tacaatactc tcagtagttt acaacggcat 120
tatattgctg tcaaacattg cttatgctgt gtgagttggg gaaaacttat ttcccccctct 180 aaaaaaaatt aaggctcagt ttccaaaaga taattatatc agtcattttt ctgtttaaga 240
gactgggaaa attcgggaat aaaaagcaca aaggggtgga gggtgagggg tagctccaca 300
cactctcatt cattcatact gaagttactc aatgtgattt ttttttttaa ggctccttct 360
atctgaaaat gtgtttggtt acaaaaacaa acaaatcagt agatgggagg ggtactaggt 420
acagatctac agcattcaaa caaggaaaac taagctcttt gttaccagtt gctggttaaa 480
atgtggtcta cgagctgcct acatataaat gcgcacacac attaactttg actcactttt 540
ctttggcgaa gcttactgaa tagtatttct cttccaacac actaatgaca ctaatttaca 600
tttcctt 607

<210> SEQ ID NO 105

<211> LENGTH: 22
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 105
aaaaatccag cgtggacaat gg 22

-continued

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 106
tgtggcaagt tctgcatcat c 21

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 107
gaaaatccag cgtggacaat 20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 108
catctgagga gaacgcatga 20

<210> SEQ ID NO 109
<211> LENGTH: 21
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 109
tgcaatccct gaaactgaca a 21

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 110
tcagcactct gcttgtggtc 20

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 111
tactggctag tggtggaccc 20

<210> SEQ ID NO 112

```
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 112

agtgggatgg tgggtgtaag                                                20


<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 113

tgcagttcgc cttcactatg                                                20


<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 114

gcagtctcat tccaagccat                                                20


<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 115

gaaacggctt tcagttgagc                                                20


<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 116

ctcgaccaaa aaggaccaga                                                20


<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 117

acctgacctg ccgtctagaa                                                20


<210> SEQ ID NO 118
<211> LENGTH: 20
```

-continued

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 118

tccaccaccc tgttgctgta                                                20
```